US010538812B2

(12) United States Patent
Katsuragi et al.

(10) Patent No.: US 10,538,812 B2
(45) Date of Patent: Jan. 21, 2020

(54) PRIMER SET AND METHOD FOR AMPLIFYING EXONS OF PKD1 GENE AND PKD2 GENE

(71) Applicant: OTSUKA PHARMACEUTICAL CO., LTD., Tokyo (JP)

(72) Inventors: Kiyonori Katsuragi, Osaka (JP); Moritoshi Kinoshita, Osaka (JP); Daisuke Koga, Osaka (JP); Ryo Higashiyama, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/534,853

(22) PCT Filed: Nov. 13, 2015

(86) PCT No.: PCT/JP2015/081941

§ 371 (c)(1),
(2) Date: Aug. 22, 2017

(87) PCT Pub. No.: WO2016/080299

PCT Pub. Date: May 26, 2016

(65) Prior Publication Data

US 2018/0037955 A1 Feb. 8, 2018

(30) Foreign Application Priority Data

Nov. 19, 2014 (JP) ................................ 2014-235066

(51) Int. Cl.

| | |
|---|---|
| ***C12Q 1/68*** | (2018.01) |
| ***C12N 15/10*** | (2006.01) |
| ***C12Q 1/6883*** | (2018.01) |

(52) U.S. Cl.

CPC ....... *C12Q 1/6883* (2013.01); *C12N 15/1093* (2013.01); *C12Q 2600/118* (2013.01); *C12Q 2600/156* (2013.01); *C12Q 2600/16* (2013.01)

(58) Field of Classification Search

None

See application file for complete search history.

(56) References Cited

U.S. PATENT DOCUMENTS

| | | | | |
|---|---|---|---|---|
| 2003/0152936 | A1 | 8/2003 | Jones et al. | |
| 2005/0100898 | A1 | 5/2005 | Jones et al. | |
| 2012/0295819 | A1* | 11/2012 | Leamon ............... | C12Q 1/6806 506/26 |

FOREIGN PATENT DOCUMENTS

| | | | |
|---|---|---|---|
| JP | 2002-503952 | A | 2/2002 |
| JP | 2004-504038 | A | 2/2004 |
| JP | 2009-065988 | A | 4/2009 |
| JP | 2009-544314 | A | 12/2009 |
| JP | 2010-528599 | A | 8/2010 |
| JP | 2011-518568 | A | 6/2011 |
| JP | 2014-212711 | A | 11/2014 |
| WO | 97/44457 | A1 | 11/1997 |
| WO | 02/06529 | A2 | 1/2002 |
| WO | 2008/094194 | A2 | 8/2008 |
| WO | 2008/146306 | A2 | 12/2008 |
| WO | 2009/132860 | A1 | 11/2009 |

OTHER PUBLICATIONS

Trujillano D, Bullich G, Ossowski S, Ballarin J, Torra R, Estivill X, Ars E. Diagnosis of autosomal dominant polycystic kidney disease using efficient PKD1 and PKD2 targeted next-generation sequencing. Mol Genet Genomic Med. Sep. 2014; 2(5):412-21. Epub May 23, 2014. (Year: 2014).*

Tarn et al. Analysis of KIT mutations in sporadic and familial gastrointestinal stromal tumors: therapeutic implications through protein modeling. Clin Cancer Res. May 15, 2005; 11(10):3668-77 (Year: 2005).*

Hayashi T, Mochizuki T, Reynolds DM, Wu G, Cai Y, Somlo S. Characterization of the exon structure of the polycystic kidney disease 2 gene (PKD2). Genomics. Aug. 15, 1997; 44(1):131-6. (Year: 1997).*

Rossetti S, Strmecki L, Gamble V, Burton S, Sneddon V, Peral B, Roy S, Bakkaloglu A, Komel R, Winearls CG, Harris PC. Mutation analysis of the entire PKD1 gene: genetic and diagnostic implications. Am J Hum Genet. Jan. 2001; 68(1):46-63. Epub Dec. 12, 2000. (Year: 2001).*

Rossetti S, Chauveau D, Walker D, Saggar-Malik A, Winearls CG, Torres VE, Harris PC. A complete mutation screen of the ADPKD genes by DHPLC. Kidney Int. May 2002; 61(5):1588-99. (Year: 2002).*

Lee KR, Park E, Moon SH, Kim JM, Kwon OJ, Kim MH, Sohn YH, Ko SY, Oh HB. Development and clinical evaluation of a microarray for HLA-A and -DRB1 genotyping. Tissue Antigens. Dec. 2008; 72(6):568-77. Epub Oct. 18, 2008. (Year: 2008).*

Yoo BH, Bochkareva E, Bochkarev A, Mou TC, Gray DM. 2'-O-methyl-modified phosphorothioate antisense oligonucleotides have reduced non-specific effects in vitro. Nucleic Acids Res. Apr. 2, 2004; 32(6):2008-16. (Year: 2004).*

Fredriksson S, Baner J, Dahl F, Chu A, Ji H, Welch K, Davis RW. Multiplex amplification of all coding sequences within 10 cancer genes by Gene-Collector. Nucleic Acids Res. 2007; 35(7):e47. Epub Feb. 22, 2007. (Year: 2007).*

Korbie DJ, Mattick JS. Touchdown PCR for increased specificity and sensitivity in PCR amplification. Nat Protoc. 2008; 3(9):1452-6. (Year: 2008).*

Barker DL, Hansen MS, Faruqi AF, Giannola D, Irsula OR, Lasken RS, Latterich M, Makarov V, Oliphant A, Pinter JH, Shen R, Sleptsova I, Ziehler W, Lai E. Two methods of whole-genome amplification enable accurate genotyping across a 2320-SNP linkage panel. Genome Res. May 2004; 14(5):901-7. (Year: 2004).*

(Continued)

*Primary Examiner* — Gary Benzion
*Assistant Examiner* — Olayinka A Oyeyemi
(74) *Attorney, Agent, or Firm* — Sughrue Mion, PLLC

(57) ABSTRACT

The present invention provides a means for efficiently amplifying the exons of PKD1 and PKD2 genes, and a primer set that can amplify all the exons of PKD1 and PKD2 genes under a single set of PCR conditions.

9 Claims, 4 Drawing Sheets

Specification includes a Sequence Listing.

(56) References Cited

OTHER PUBLICATIONS

Communication, dated May 18, 2018, issued by the European Patent Office in counterpart European Application No. 15861187.1.
Buset Rios et al.: "Genetic diagnosis of autosomal dominant polycystic kidney disease using multiplex-PCR", Nefrologia, Jan. 1, 2009, vol. 29 Issue 4, pp. 327-330; XP055473822, Retrieved from the Internet: URL: http:// www.revistanefrologia.com/en-publicacion-nefrologia-articulo-geneticdiagnosis-autosomal-dominant-polycystic-kidney-disease-using-multiplexpcr-X2013251409003515 (4 pages total).
K Vouk et al: "Fluorescent multiplex PCR and capillary electrophoresis for analysis of PKD1 and PKD2 associated microsatellite markers", BioTechniques, Dec. 1, 2000, p. 1186-1190, vol. 29, No. 6, XP055473522, Retrieved from the Internet: URL: https://www.researchgate.net/profile/Radovan_Komel/publication/12203016_Fluorescent_multiplex_PCR_and_capillary_electrophoresis_for_analysis_of_PKD1_and_PKD2_associated_microsatellite_markers/links/00463526e6019364e9000000/Fluorescent-multiplex-PCR-and-capillaryelectrophoresis-for-analysis-of-PKD1- (4 pages total).
Marie-Pierre Audrezet et al: "Autosomal dominant polycystic kidney disease: Comprehensive mutation analysis of PKD1 and PKD2 in 700 unrelated patients", Human Mutation, Aug. 1, 2012, pp. 1239-1250, vol. 33, No. 8, XP055473832, ISSN: 1059-7794 (12 pages total).
Ming-Yang et al: "Novel PKD1 and PKD2 mutations in Taiwanese patients with autosomal dominant polycystic kidney disease", Journal of Human Genetics, Aug. 29, 2013, pp. 720-727, vol. 58, No. 11, XP055473845, GB; JP ISSN: 1434-5161, DOI: 10.1038/jhg.2013.91 (8 pages total).
Sandro Rossetti et al., "Mutation Analysis of the Entire PKD1 Gene: Genetic and Diagnostic Implications", The American Journal of Human Genetics., 2001, pp. 46-63, vol. 68, No. 1.
Kwok W. Chan, "Adult Polycystic Kidney Disease in Hong Kong Chinese: An Autopsy Study", Pathology, 1993, pp. 229-232, vol. 25.
F Davies et al., "Polycystic Kidney Disease Re-evaluated: A Population-based Study", Quarterly Journal of Medicine, New Series, Jun. 1991, pp. 477-485, vol. 79, No. 290.
Eiji Higashihara et al., "Prevalence and Renal Prognosis of Diagnosed Autosomal Dominant Polycystic Kidney Disease in Japan", Nephron, 1998, pp. 421-427, vol. 80.
Christopher J. Ward et al., "The Polycystic Kidney Disease 1 Gene Encodes a 14 kb Transcript and Lies within a Duplicated Region on Chromosome 16", The European Polycystic Kidney Disease Consortium, Cell, Jun. 17, 1994, pp. 881-894, vol. 77.
Toshio Mochizuki et al., "PKD2, a Gene for Polycystic Kidney Disease That Encodes an Integral Membrane Protein", Science, May 31, 1996, pp. 1339-1342, vol. 272.
Jim Hughes et al., "The polycystic kidney disease 1 (PKD1) gene encodes a novel protein with multiple cell recognition domains", Nature Genetics, Jun. 1995, pp. 151-160, vol. 10.
Roser Torra et al., "Linkage, Clinical Features, and Prognosis of Autosomal Dominant Polycystic Kidney Disease Type 1 and 2", Journal of the American Society of Nephrology, 1996, pp. 2142-2151, vol. 7, No. 10.
Sandro Rossetti et al., "A complete mutation screen of the ADPKD genes by DHPLC", Kidney International, 2002, pp. 1588-1599, vol. 61.
Ying-Cai Tan et al., "Novel Method for Genomic Analysis of PKD1 and PKD2 Mutations in Autosomal Dominant polycystic Kidney Disease", Human Mutation, 2009, pp. 264-273, vol. 30, No. 2.
Sandro Rossetti et al., "Identification of Gene Mutations in Autosomal Dominant Polycystic Kidney Disease through Targeted Resequencing", Journal of the American Society of Nephrology, 2012, pp. 915-933, vol. 23.
Barbera Veldhuisen et al., Genes homologous to the autosomal dominant polycystic kidney disease genes (PKD1 and PKD2), European Journal of Human Genetics, 1999, pp. 860-872, vol. 7.
Ying-Cai Tan et al., "A Novel Long-Range PCR Sequencing Method for Genetic Analysis of the Entire PKD1 Gene", The Journal of Molecular Diagnostics, Jul. 2012, pp. 305-313, vol. 14, No. 4.
Moritoshi Kinoshita et al., "Technical Evaluation: Identification of Pathogenic Mutations in PKD1 and PKD2 in Patients with Autosomal Dominant Polycystic Kidney Disease by Next-Generation Sequencing and Use of a Comprehensive New Classification System", POLS ONE, Nov. 11, 2016, pp. 1-15, vol. 11.
International Search Report for PCT/JP2015/081941, dated Feb. 16, 2016.

* cited by examiner

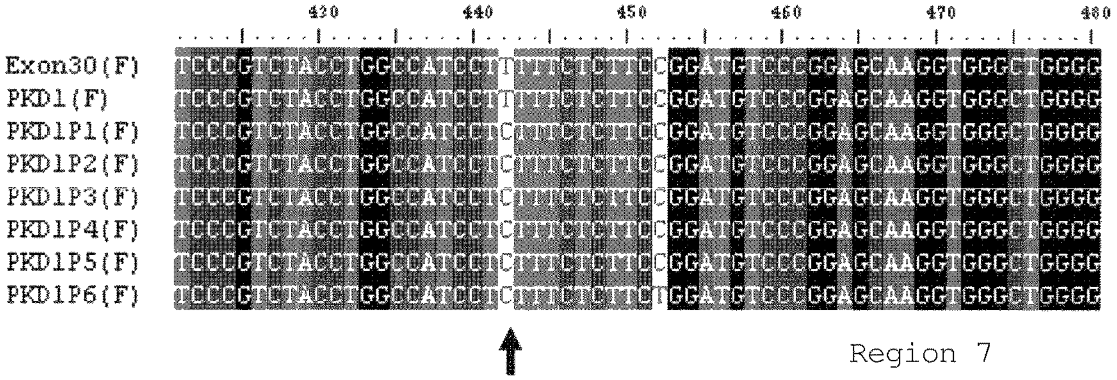

Fig. 3-7

```
              430         440         450         460         470         480
         ....|....|....|....|....|....|....|....|....|....|....|....|
Exon30(F) TCCCGTCTACCTGGCCATCCTTTTTCTCTTCGGATGTCCCGGAGCAAGGTGGGCTGGGG
PKD1(F)   TCCCGTCTACCTGGCCATCCTTTTTCTCTTCGGATGTCCCGGAGCAAGGTGGGCTGGGG
PKD1P1(F) TCCCGTCTACCTGGCCATCCTCTTTCTCTTCCGGATGTCCCGGAGCAAGGTGGGCTGGGG
PKD1P2(F) TCCCGTCTACCTGGCCATCCTCTTTCTCTTCCGGATGTCCCGGAGCAAGGTGGGCTGGGG
PKD1P3(F) TCCCGTCTACCTGGCCATCCTCTTTCTCTTCCGGATGTCCCGGAGCAAGGTGGGCTGGGG
PKD1P4(F) TCCCGTCTACCTGGCCATCCTCTTTCTCTTCCGGATGTCCCGGAGCAAGGTGGGCTGGGG
PKD1P5(F) TCCCGTCTACCTGGCCATCCTCTTTCTCTTCCGGATGTCCCGGAGCAAGGTGGGCTGGGG
PKD1P6(F) TCCCGTCTACCTGGCCATCCTCTTTCTCTTCTGGATGTCCCGGAGCAAGGTGGGCTGGGG
                               ↑                          Region 7
```

PRIMER SET AND METHOD FOR AMPLIFYING EXONS OF PKD1 GENE AND PKD2 GENE

This application is a National Stage of International Application No. PCT/JP2015/081941 filed Nov. 13, 2015, claiming priority based on Japanese Patent Application No. 2014-235066 filed Nov. 19, 2014, the contents of all of which are incorporated herein by reference in their entirety.

TECHNICAL FIELD

The present invention relates to a primer set and a method for amplifying the exons of PKD1 and PKD2 genes, etc.

BACKGROUND ART

Polycystic kidney disease (PKD) is a disease in which the formation of many cysts in the kidney causes an increase of kidney volume and a reduction of renal function and ultimately causes renal failure requiring dialysis. PKD is frequently an inherited disease and can be classified into autosomal dominant PKD (ADPKD) and autosomal recessive PKD (ARPKD). ARPKD is very rare. The ADPKD 1 incidence rate is said to be one per 300 to 500 persons (Non-patent Literature (NPL) 1). A report also says that the number of ADPKD patients treated in medical institutions is only 1 out of 2,000 to 4,000 persons (Non-patent Literature (NPL) 2 and NPL 3). Many patients do not recognize for their entire life that they themselves suffer from ADPKD and thus do not receive appropriate medical treatment (Non-patent Literature (NPL) 3). Therefore, the spread of a more appropriate diagnosis has been desired.

Two kinds of genes, the PKD1 gene (Non-patent Literature (NPL) 4) and the PKD2 gene (Non-patent Literature (NPL) 5), have been identified as ADPKD-causing genes. It has been reported that the patients resulting from a mutation in the PKD1 gene account for 85% to 90%, whereas the patients resulting from a mutation in the PKD2 gene account for 10% to 15% (Non-patent Literature (NPL) 6). When patients have an abnormality in the PKD1 gene, the average age of shifting to dialysis is 53. Compared with 63, which is the age at which patients with an abnormality in the PKD2 gene shift to dialysis, the progression of the disease in patients having an abnormality in the PKD1 gene is fast (Non-patent Literature (NPL) 7). There are various types and positions of disease-causing mutations in PKD1 and PKD2 genes. Disease-causing mutations characteristic of particular pedigrees exist (Non-patent Literature (NPL) 8).

At present, for definitive diagnosis of ADPKD, diagnostic imaging using CT, MRI, and ultrasonic tomograms is performed and diagnosis is made based on the number of cysts that can be confirmed in the kidneys. However, this diagnostic method cannot be used until cysts are formed. Therefore, it is impossible to know whether the patient is a PKD gene mutation carrier before the formation of many cysts. If technical innovations provide an environment in which PKD gene diagnosis can be more easily utilized, it is expected to assist definitive diagnosis of PKD mutation carriers who have not yet developed the disease and also become possible to grasp the difference in disease progression rate by identifying the gene and region in which a mutation exists.

As methods for detecting mutations in PKD1 and PKD2 genes, (1) mutation detection using the Sanger method (Non-patent Literature (NPL) 9), (2) mutation detection using DHPLC (denaturing high-pressure chromatography) (Non-patent Literature (NPL) 10), (3) mutation detection using endonuclease and DHPLC (Non-patent Literature (NPL) 11), (4) mutation detection using a next-generation sequencer (Non-patent Literature (NPL) 12), and like methods have been reported.

CITATION LIST

Non-Patent Literature

NPL 1: Adult polycystic kidney disease in Hong Kong Chinese: an autopsy study. Chan K W. Pathology., Vol. 25, pp. 229-232, 1993.

NPL 2: Polycystic kidney disease re-evaluated: a population-based study. Davies F et al. Q J Med. Vol. 79. pp. 477-485. 1991.

NPL 3: Prevalence and renal prognosis of diagnosed autosomal dominant polycystic kidney disease in Japan. Higashihara E et al. Nephron. Vol. 80, pp. 421-427, 1998.

NPL 4: The polycystic kidney disease 1 gene encodes a 14 kb transcript and lies within a duplicated region on chromosome 16. The European Polycystic Kidney Disease Consortium. Cell. Vol. 77, pp. 881-94, 1994.

NPL 5: PKD2, a gene for polycystic kidney disease that encodes an integral membrane protein. Mochizuki T et al. Science. Vol. 272, pp. 1339-42, 1996.

NPL 6: The polycystic kidney disease 1 (PKD1) gene encodes a novel protein with multiple cell recognition domains. Hughes J et al. Nat Genet. Vol. 10. pp. 151-160. 1995.

NPL 7: Linkage, clinical features, and prognosis of autosomal dominant polycystic kidney disease types 1 and 2. Torra R et al. J Am Soc Nephrol. Vol. 7. pp. 2142-2151. 1996.

NPL 8: A Complete mutation screen of the ADPKD genes by DHPLC. Rossetti S et al. Kidney International. Vol. 61, pp. 1588-1599, 2002.

NPL 9: Mutation analysis of the entire PKD1 gene: Genetic and diagnostic implications. Rossetti S et al. The American Journal of Human Genetics. Vol. 68, pp. 46-63, 2001.

NPL 10: Novel method for genomic analysis of PKD1 and PKD2 mutations in autosomal dominant polycystic kidney disease. Y C Tan et al. Human Mutation. Vol. 30, pp. 264-273, 2009.

NPL 11: Identification of gene mutations in autosomal dominant polycystic kidney disease through targeted resequencing. Rossetti S et al. J Am Soc Nephrol 23: 915-933, 2012.

"NPL 12: Genes homologous to the autosomal dominant polycystic kidney disease genes (PKD1 and PKD2). Barbera Veldhuisen et al. European Journal of Human Genetics. Vol. 7, pp. 860-872, June 1999.

NPL 13: A novel long-range PCR sequencing method for genetic analysis of the entire PKD1 gene. Ying-Cai Tan et al. Journal of Molecular Diagnostics. Vol. 14, No. 4, July 2012.

SUMMARY OF INVENTION

Technical Problem

PKD1 and PKD2 genes are both very long; 46 exons exist in the PKD1 gene and 15 exons exist in the PKD2 gene. Since there are 6 kinds of pseudogenes that are highly homologous to the sequence of the PKD1, amplifying the exons of PKD1 and PKD2 genes necessitates avoiding pseudogenes. Further, a region having a very high GC content exists in the PKD1 gene. For these reasons, all the methods reported so far for amplifying all the exons of the PKD1 and PKD2 genes require performing many (e.g., 9) different PCRs under different PCR conditions (Non-patent Literature (NPL) 13). Therefore, it took a great amount of time to obtain amplification products of all the exons. Accordingly, a main object of the present invention is to provide a means for more efficiently amplifying the exons of PKD1 and PKD2 genes.

Solution to Problem

The present inventors conducted extensive research to achieve the above object. As a result, the present inventors found that when primers targeting specific regions in PKD1 and PKD2 genes are designed and used in a combination, amplification products of all the exons of PKD1 and PKD2 genes can be obtained with significantly increased efficiency. Based on this finding and further research and improvements, for example, the following representative inventions are provided.

Item 1.

A primer set for amplifying all the exons of PKD1 and PDK2 genes under a single set of PCR conditions.

Item 2.

The primer set according to Item 1 comprising primer pairs 1 to 18 shown in Table 1 below.

TABLE 1

| Primer pair | Primer | Specific recognition region |
|---|---|---|
| 1 | 1F | Region of positions 48916 to 48930 of SEQ ID NO: 37 |
| | 1R | Complementary region of positions 46427 to 46413 of SEQ ID NO: 37 |
| 2 | 2F | Region of positions 31431 to 31445 of SEQ ID NO: 37 |
| | 2R | Complementary region of positions 27875 to 27861 of SEQ ID NO: 37 |
| 3 | 3F | Region of positions 27875 to 27889 of SEQ ID NO: 37 |
| | 3R | Complementary region of positions 24227 to 24213 of SEQ ID NO: 37 |
| 4 | 4F | Region of positions 24247 to 24261 of SEQ ID NO: 37 |
| | 4R | Complementary region of positions 18933 to 18919 of SEQ ID NO: 37 |
| 5 | 5F | Region of positions 19226 to 19240 of SEQ ID NO: 37 |
| | 5R | Complementary region of positions 16698 to 16684 of SEQ ID NO: 37 |
| 6 | 6F | Region of positions 16393 to 16407 of SEQ ID NO: 37 |
| | 6R | Complementary region of positions 12889 to 12875 of SEQ ID NO: 37 |
| 7 | 7F | Region of positions 12193 to 12207 of SEQ ID NO: 37 |
| | 7R | Complementary region of positions 8534 to 8520 of SEQ ID NO: 37 |
| 8 | 8F | Region of positions 6284 to 6298 of SEQ ID NO: 37 |
| | 8R | Complementary region of positions 3261 to 3247 of SEQ ID NO: 37 |
| 9 | 9F | Region of positions 3525 to 3539 of SEQ ID NO: 37 |
| | 9R | Complementary region of positions 28 to 14 of SEQ ID NO: 37 |
| 10 | 10F | Complementary region of positions 25 to 11 of SEQ ID NO: 38 |
| | 10R | Region of positions 1537 to 1551 of SEQ ID NO: 38 |
| 11 | 11F | Complementary region of positions 11432 to 11418 of SEQ ID NO: 38 |
| | 11R | Region of positions 12623 to 12637 of SEQ ID NO: 38 |
| 12 | 12F | Complementary region of positions 28901 to 28887 of SEQ ID NO: 38 |
| | 12R | Region of positions 31264 to 31278 of SEQ ID NO: 38 |
| 13 | 13F | Complementary region of positions 35718 to 35704 of SEQ ID NO: 38 |
| | 13R | Region of positions 39836 to 39850 of SEQ ID NO: 38 |
| 14 | 14F | Complementary region of positions 44259 to 44245 of SEQ ID NO: 38 |
| | 14R | Region of positions 45415 to 45429 of SEQ ID NO: 38 |
| 15 | 15F | Complementary region of positions 47754 to 47740 of SEQ ID NO: 38 |
| | 15R | Region of positions 52221 to 52235 of SEQ ID NO: 38 |
| 16 | 16F | Complementary region of positions 53806 to 53792 of SEQ ID NO: 38 |
| | 16R | Region of positions 55288 to 55302 of SEQ ID NO: 38 |
| 17 | 17F | Complementary region of positions 57914 to 57900 of SEQ ID NO: 38 |
| | 17R | Region of positions 60808 to 60822 of SEQ ID NO: 38 |
| 18 | 18F | Complementary region of positions 67328 to 67314 of SEQ ID NO: 38 |
| | 18R | Region of positions 68792 to 68806 of SEQ ID NO: 38 |

Item 3.

The primer set according to Item 1 or 2, wherein each of the primers has a length of 15 to 40 bases.

Item 4.

The primer set according to Item 2 or 3, wherein the 1F primer comprises a base sequence of at least positions 15 to 29 of the base sequence shown in SEQ ID NO: 1, the 1R primer comprises a base sequence of at least positions 16 to 30 of the base sequence shown in SEQ ID NO: 2, the 2F primer comprises a base sequence of at least positions 14 to 28 of the base sequence shown in SEQ ID NO: 3, the 2R primer comprises a base sequence of at least positions 13 to 27 of the base sequence shown in SEQ ID NO: 4, the 3F primer comprises a base sequence of at least positions 14 to 28 of the base sequence shown in SEQ ID NO: 5, the 3R primer comprises a base sequence of at least positions 14 to 28 of the base sequence shown in SEQ ID NO: 6, the 4F primer comprises a base sequence of at least positions 6 to 20 of the base sequence shown in SEQ ID NO: 7, the 4R primer comprises a base sequence of at least positions 8 to 22 of the base sequence shown in SEQ ID NO: 8, the 5F primer comprises a base sequence of at least positions 14 to 28 of the base sequence shown in SEQ ID NO: 9, the 5R primer comprises a base sequence of at least positions 10 to 24 of the base sequence shown in SEQ ID NO: 10, the 6F primer comprises a base sequence of at least positions 12 to 26 of the base sequence shown in SEQ ID NO: 11,
the 6R primer comprises a base sequence of at least positions 12 to 26 of the base sequence shown in SEQ ID NO: 12,
the 7F primer comprises a base sequence of at least positions 21 to 35 of the base sequence shown in SEQ ID NO: 13,
the 7R primer comprises a base sequence of at least positions 20 to 34 of the base sequence shown in SEQ ID NO: 14,
the 8F primer comprises a base sequence of at least positions 16 to 30 of the base sequence shown in SEQ ID NO: 15,
the 8R primer comprises a base sequence of at least positions 13 to 27 of the base sequence shown in SEQ ID NO: 16,
the 9F primer comprises a base sequence of at least positions 21 to 35 of the base sequence shown in SEQ ID NO: 17,
the 9R primer comprises a base sequence of at least positions 14 to 28 of the base sequence shown in SEQ ID NO: 18,
the 10F primer comprises a base sequence of at least positions 11 to 25 of the base sequence shown in SEQ ID NO: 19,
the 10R primer comprises a base sequence of at least positions 11 to 25 of the base sequence shown in SEQ ID NO: 20,
the 11F primer comprises a base sequence of at least positions 11 to 25 of the base sequence shown in SEQ ID NO: 21,
the 11R primer comprises a base sequence of at least positions 11 to 25 of the base sequence shown in SEQ ID NO: 22,
the 12F primer comprises a base sequence of at least positions 11 to 25 of the base sequence shown in SEQ ID NO: 23,
the 12R primer comprises a base sequence of at least positions 17 to 31 of the base sequence shown in SEQ ID NO: 24,
the 13F primer comprises a base sequence of at least positions 11 to 25 of the base sequence shown in SEQ ID NO: 25,
the 13R primer comprises a base sequence of at least positions 16 to 30 of the base sequence shown in SEQ ID NO: 26,
the 14F primer comprises a base sequence of at least positions 11 to 25 of the base sequence shown in SEQ ID NO: 27,
the 14R primer comprises a base sequence of at least positions 12 to 26 of the base sequence shown in SEQ ID NO: 28,
the 15F primer comprises a base sequence of at least positions 11 to 25 of the base sequence shown in SEQ ID NO: 29,
the 15R primer comprises a base sequence of at least positions 11 to 25 of the base sequence shown in SEQ ID NO: 30,
the 16F primer comprises a base sequence of at least positions 14 to 28 of the base sequence shown in SEQ ID NO: 31,
the 16R primer comprises a base sequence of at least positions 11 to 25 of the base sequence shown in SEQ ID NO: 32,
the 17F primer comprises a base sequence of at least positions 16 to 30 of the base sequence shown in SEQ ID NO: 33,
the 17R primer comprises a base sequence of at least positions 12 to 26 of the base sequence shown in SEQ ID NO: 34,
the 18F primer comprises a base sequence of at least positions 12 to 26 of the base sequence shown in SEQ ID NO: 35, and/or
the 18R primer comprises a base sequence of at least positions 13 to 27 of the base sequence shown in SEQ ID NO: 36.

Item 5.

The primer set according to any one of Items 1 to 4, wherein each of the primers is a lyophilized primer.

Item 6.

The primer set according to any one of Items 1 to 4, wherein each of the primers is in a solution suitable for use in PCR.

Item 7.

The primer set according to any one of Items 1 to 6, wherein the single set of PCR conditions include a single temperature of 62 to 80° C. that is used for both annealing and extension reactions.

Item 8.

A kit for amplifying all the exons of PKD1 and PKD2 genes under a single set of PCR conditions, the kit comprising the primer set according to any one of Items 1 to 6.

Item 9.

A method for amplifying all the exons of PKD1 and PKD2 genes under a single set of PCR conditions, the method comprising performing PCR using the primer set according to any one of items 1 to 7 and using, as a template, genomic DNA obtained from a subject.

Item 10.

The method according to Item 9, wherein the PCR includes multiple different PCRs.

Item 11.

The method according to Item 10, wherein the multiple different PCRs are all performed simultaneously.

Item 12.

A method for determining the presence or absence of a mutation in the PKD1 gene and/or PKD2 gene of a subject, comprising determining at least one of the base sequences of amplification products obtained by the method according to any one of Items 9 to 11.

Item 13.

A method for determining whether a subject has a risk of developing polycystic kidney disease or has developed polycystic kidney disease, based on the presence or absence of a mutation in the PKD1 gene and/or PKD2 gene determined by the method according to Item 12.

Item E1.

Use of the primer set according to any one of Items 1 to 6 for amplifying all the exons of PKD1 and PKD2 genes under a single set of PCR conditions.

Item E2.

Use of a kit comprising the primer set according to any one of Items 1 to 6 for amplifying all the exons of PKD1 and PKD2 genes under a single set of PCR conditions.

Advantageous Effects of Invention

According to the present invention, all the exons of PKD1 and PKD2 genes can be efficiently amplified. Preferably, all the exons of PKD1 and PKD2 genes can be efficiently amplified under single (or a small number of variations of) PCR cycling conditions. For example, according to the present invention, all the exons of PKD1 and PKD2 genes can be simultaneously amplified using one PCR device (a thermal cycler). According to a preferable embodiment of the present invention, PCRs using multiple pairs of primers can be simultaneously performed in a single reaction vessel. Therefore, necessary exons among the exons of PKD1 and PKD2 genes can be amplified more efficiently and economically. Further, according to the present invention, amplification of the exons of PKD1 and PKD2 genes can be performed, while avoiding the amplification of pseudogenes. Therefore, the present invention allows for efficiently detecting the presence of a mutation in the PKD1 and PKD2 genes of a subject and/or determining the onset of polycystic kidney disease or predicting the risk of developing the disease, based on the detection.

BRIEF DESCRIPTION OF DRAWINGS

FIG. 3-1 shows alignment of a partial sequence in region 1 determined using the Sanger method with pseudogene sequences corresponding to the partial sequence. Region 1 means the region amplified with primer pair 1 shown in Table 3. The sequences are, in descending order, the sequence of the Multiplex PCR amplification product determined by the Sanger method (Exon 1(R); (SEQ ID NO: 39)), a reference sequence of the PKD1 gene (PKD1(R); (SEQ ID NO: 39)), and sequences of three kinds of PKD1 pseudogenes (PKD1P3(R), PKD1P5(R), and PKD1P6(R); (SEQ ID NO: 40)). (R) indicates that the sequence is shown in reverse orientation. The black arrow indicates the location where a base specific to PKD1 exists.

FIG. 3-2 shows the alignment of a partial sequence in region 2 determined using the Sanger method with pseudogene sequences corresponding to the partial sequence. Region 2 means the region amplified with primer pair 2 shown in Table 3. The sequences are, in descending order, the sequence of the Multiplex PCR amplification product determined by the Sanger method (Exon 6(R) (SEQ ID NO: 41)), a reference sequence of the PKD1 gene (PKD1(R) (SEQ ID NO: 41)), and sequences of six kinds of PKD1 pseudogenes (PKD1P1(R) to PKD1P6(R); (SEQ ID NO: 42)). (R) indicates that the sequence is shown in reverse orientation. The black arrow indicates the location where a base specific to PKD1 exists.

FIG. 3-3 shows alignment of a partial sequence in region 3 determined using the Sanger method with pseudogene sequences corresponding to the partial sequence. Region 3 means the region amplified with primer pair 3 shown in Table 3. The sequences are, in descending order, the sequence of the Multiplex PCR amplification product determined by the Sanger method (Exon 11A(R) (SEQ ID NO: 43)), a reference sequence of the PKD1 gene (PKD1(R) (SEQ ID NO: 43)), and sequences of five kinds of PKD1 pseudogenes (PKD1P1(R) to PKD1P5(R); (SEQ ID NO: 44)). (R) indicates that the sequence is shown in reverse orientation. The black arrow indicates the location where a base specific to PKD1 exists.

FIG. 3-4 shows alignment of a partial sequence in region 4 determined using the Sanger method with pseudogene sequences corresponding to the partial sequence. Region 4 means the region amplified with primer pair 4 shown in Table 3. The sequences are, in descending order, the sequence of the Multiplex PCR amplification product determined by the Sanger method (Exon 15A(F) (SEQ ID NO: 45)), a reference sequence of the PKD1 gene (PKD1(F) (SEQ ID NO: 45)), and sequences of five kinds of PKD1 pseudogenes (PKD1P1(F) (SEQ ID NO: 46); PKD1P2(F) (SEQ ID NO: 47); PKD1P3(F) (SEQ ID NO: 46); PKD1P4 (F) (SEQ ID NO: 46) to and PKD1P5(F) (SEQ ID NO: 48)). (F) indicates that the sequence is shown in forward orientation. The black arrow indicates the location where a base specific to PKD1 exists.

FIG. 3-5 shows alignment of a partial sequence in region 5 determined using the Sanger method with pseudogene sequences corresponding to the partial sequence. Region 5 means the region amplified with primer pair 5 shown in Table 3. The sequences are, in descending order, a sequence of the Multiplex PCR amplification product determined by the Sanger method (Exon 21(F); (SEQ ID NO: 49)), a reference sequence of the PKD1 gene (PKD1(F); (SEQ ID NO: 49)), and sequences of six kinds of PKD1 pseudogenes (PKD1P1(F) to PKD1P6(F); (SEQ ID NO: 50)). (F) indicates that the sequence is shown in forward orientation. The black arrow indicates the location where a base specific to PKD1 exists.

FIG. 3-6 shows alignment of a partial sequence in region 6 determined using the Sanger method with pseudogene sequences corresponding to the partial sequence. Region 6 means the region amplified with primer pair 6 shown in Table 3. The sequences are, in descending order, the sequence of the Multiplex PCR amplification product determined by the Sanger method (Exon 26(R); (SEQ ID NO: 51)), a reference sequence of the PKD1 gene (PKD1(R); (SEQ ID NO: 51)), and sequences of six kinds of PKD1 pseudogenes (PKD1P1(R) (SEQ ID NO: 52); PKD1P2(R) (SEQ ID NO: 52); PKD1P3(R) (SEQ ID NO: 53); PKD1P4 (R) (SEQ ID NO: 52); PKD1P5(R) (SEQ ID NO: 52) and PKD1P6(R) (SEQ ID NO: 53)). (R) indicates that the sequence is shown in reverse direction. The black arrow indicates the location where a base specific to PKD1 exists.

FIG. 3-7 shows alignment of a partial sequence in region 7 determined using the Sanger method with pseudogene sequences corresponding to the partial sequence. Region 7 means the region amplified with primer pair 7 shown in Table 3. The sequences are, in descending order, the sequence of the Multiplex PCR amplification product determined by the Sanger method (Exon 30(F); (SEQ ID NO: 54)), a reference sequence of the PKD1 gene (PKD1(F); (SEQ ID NO: 54)), and sequences of six kinds of PKD1 pseudogenes (PKD1P1(F) (SEQ ID NO: 55); PKD1P2(F) (SEQ ID NO: 55); PKD1P3(F) (SEQ ID NO: 55); PKD1P4 (F) (SEQ ID NO: 55); PKD1P5(F) (SEQ ID NO: 55); and PKD1P6(F) (SEQ ID NO: 56);). (F) indicates that the sequence is shown in forward orientation. The black arrow indicates the location where a base specific to PKD1 exists.

DESCRIPTION OF EMBODIMENTS

Figure 1:
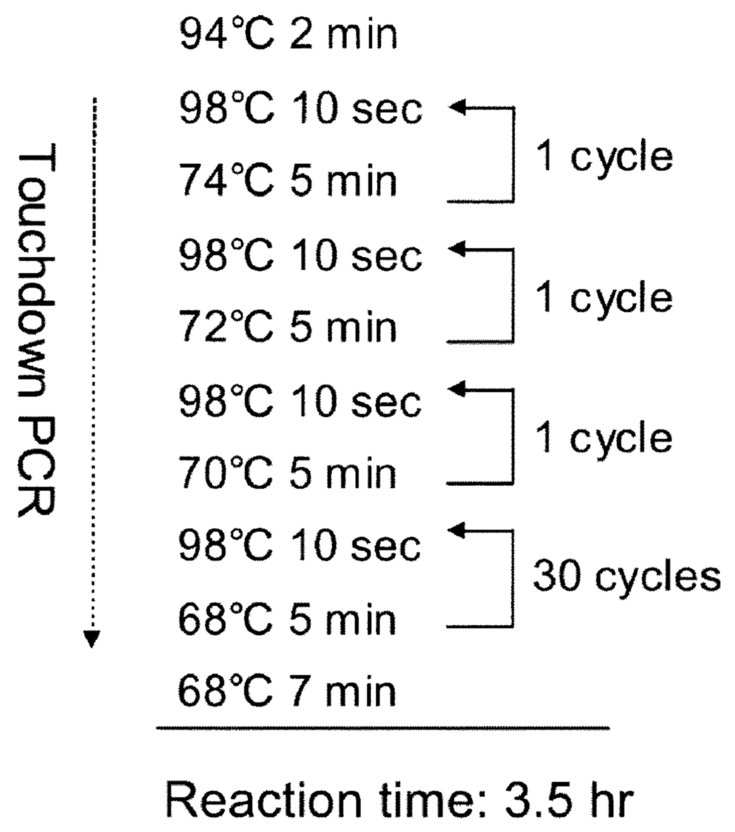
FIG. 1 shows PCR cycling conditions used in the "Multiplex PCR" section in the Examples.

1. Primer, Primer Pair, and Primer Set

The present invention provides a primer set that enables amplifying all the exons of PKD1 and PKD2 genes under a single set of PCR conditions. The regions in which all the exons of PKD1 and PKD2 genes are contained can be amplified without amplifying pseudogenes of the PKD1 gene by using a set of 18 pairs of primers shown in Table 1 above. According to a preferable embodiment of the invention, the regions in which all the exons of PKD1 and PKD2 genes are contained can be amplified under a single set of PCR conditions by using a set of 18 primer pairs.

Table 1 shows that each primer pair shown in the "Primer pair" column on the left side contains 2 kinds of primers (forward and reverse) shown in the "Primer" column at the center. Table 1 further shows that each primer shown in the "Primer" column specifically binds to the region shown in the "Specific recognition region" column on the right side. The numerical range indicated herein with "to" means a range including the numerical value before "to" as the minimum value and the numerical value after "to" as the maximum value, unless otherwise specified.

The base sequence of SEQ ID NO: 37 is a base sequence of the PKD1 gene that exists on human chromosome 16 and registered under Accession No. NC_000016 (version: NC_000016.9) at the National Center for Biotechnology Information (NCBI). The base sequence set forth in SEQ ID NO: 38 is a base sequence of the PKD2 gene that exists on chromosome 4 and registered under Accession No. NC_000004 (version: NC_000004.11) at the NCBI.

The phrase "specifically recognizing" means that when PCR is performed using human genomic DNA as a template, primers substantially bind only specific recognition regions without binding to any other region than the specific recognition regions. More preferably, specifically recognizing means that when PCR is performed using human genomic DNA as a template under PCR conditions described below, primers bind only to specific recognition regions.

The base sequence specifically recognized by forward primer (1F) of primer pair 1 is preferably a region of positions 48916 to 48930 of SEQ ID NO: 37, more preferably a region of positions 48916 to 48931, more preferably a region of positions 48916 to 48932, more preferably a region of positions 48916 to 48933, more preferably a region of positions 48916 to 48934, more preferably a region of positions 48916 to 48935, more preferably a region of positions 48916 to 48936, more preferably a region of positions 48916 to 48937, more preferably a region of positions 48916 to 48938, more preferably a region of positions 48916 to 48939, more preferably a region of positions 48916 to 48940, more preferably a region of positions 48916 to 48941, more preferably a region of positions 48916 to 48942, more preferably a region of positions 48916 to 48943, and more preferably a region of positions 48916 to 48944.

Specific examples of the 1F primer include oligonucleotides having a base sequence of positions 15 to 29 of SEQ ID NO: 1, preferably a base sequence of positions 14 to 29, more preferably a base sequence of positions 13 to 29, more preferably a base sequence of positions 12 to 29, more preferably a base sequence of positions 11 to 29, more preferably a base sequence of positions 10 to 29, preferably a base sequence of positions 9 to 29, more preferably a base sequence of positions 8 to 29, more preferably a base sequence of positions 7 to 29, more preferably a base sequence of positions 6 to 29, more preferably a base sequence of positions 5 to 29, more preferably a base sequence of positions 4 to 29, more preferably a base sequence of positions 3 to 29, more preferably a base sequence of positions 2 to 29, and more preferably a base sequence of positions 1 to 29. The base at the 5'-end corresponds to a base in the first position of each base sequence in the Sequence Listing.

The base sequence specifically recognized by the reverse primer (1R) of primer pair 1 is preferably a complementary region of positions 46427 to 46413 of SEQ ID NO: 37, more preferably a complementary region of positions 46427 to 46412, more preferably a complementary region of positions 46427 to 46411, more preferably a complementary region of positions 46427 to 46410, more preferably a complementary region of positions 46427 to 46409, more preferably a complementary region of positions 46427 to 46408, more preferably a complementary region of positions 46427 to 46407, more preferably a complementary region of positions 46427 to 46406, more preferably a complementary region of positions 46427 to 46405, more preferably a complementary region of positions 46427 to 46404, more preferably a complementary region of positions 46427 to 46403, more preferably a complementary region of positions 46427 to 46402, more preferably a complementary region of positions 46427 to 46401, more preferably a complementary region of positions 46427 to 46400, more preferably a complementary region of positions 46427 to 46399, and more preferably a complementary region of positions 46427 to 46398.

Specific examples of the 1R primer include oligonucleotides having a base sequence of positions 16 to 30 of SEQ ID NO: 2, preferably a base sequence of positions 15 to 30, more preferably a base sequence of positions 14 to 30, more preferably a base sequence of positions 13 to 30, more preferably a base sequence of positions 12 to 30, more preferably a base sequence of positions 11 to 30, more preferably a base sequence of positions 10 to 30, more preferably a base sequence of positions 9 to 30, more preferably a base sequence of positions 8 to 30, more preferably a base sequence of positions 7 to 30, more preferably a base sequence of positions 6 to 30, more preferably a base sequence of positions 5 to 30, more preferably a base sequence of positions 4 to 30, more preferably a base sequence of positions 3 to 30, more preferably a base sequence of positions 2 to 30, and more preferably a base sequence of positions 1 to 30.

The base sequence specifically recognized by the forward (2F) primer of primer pair 2 is preferably a region of positions 31431 to 31445 of SEQ ID NO: 37, more preferably a region of positions 31431 to 31446, more preferably a region of positions 31431 to 31447, more preferably a region of positions 31431 to 31448, more preferably a region of positions 31431 to 31449, more preferably a region of positions 31431 to 31450, more preferably a region of positions 31431 to 31451, more preferably a region of positions 31431 to 31452, more preferably a region of positions 31431 to 31453, more preferably a region of positions 31431 to 31454, more preferably a region of positions 31431 to 31455, more preferably a region of positions 31431 to 31456, more preferably a region of positions 31431 to 31457, and more preferably a region of positions 31431 to 31458.

Specific examples of the 2F primer include oligonucleotides having a base sequence of positions 14 to 28 of SEQ ID NO: 3, preferably a base sequence of positions 13 to 28, more preferably a base sequence of positions 12 to 28, more preferably a base sequence of positions 11 to 28, more preferably a base sequence of positions 10 to 28, more preferably a base sequence of positions 9 to 28, more preferably a base sequence of positions 8 to 28, more preferably a base sequence of positions 7 to 28, more preferably a base sequence of positions 6 to 28, more preferably a base sequence of positions 5 to 28, more preferably a base sequence of positions 4 to 28, more preferably a base sequence of positions 3 to 28, more preferably a base sequence of positions 2 to 28, and more preferably a base sequence of positions 1 to 28.

The base sequence specifically recognized by the reverse primer (2R) of primer pair 2 is preferably a complementary region of positions 27875 to 27861 in SEQ ID NO: 37, more preferably a complementary region of positions 27875 to 27860, more preferably a complementary region of positions 27875 to 27859, more preferably a complementary region of positions 27875 to 27858, more preferably a complementary region of positions 27875 to 27857, more preferably a complementary region of positions 27875 to 27856, more preferably a complementary region of positions 27875 to 27855, more preferably a complementary region of positions 27875 to 27854, more preferably a complementary region of positions 27875 to 27853, more preferably a complementary region of positions 27875 to 27852, more preferably a complementary region of positions 27875 to 27851, more preferably a complementary region of positions 27875 to 27850, and more preferably a complementary region of positions 27875 to 27849.

Specific examples of the 2R primer include oligonucleotides having a base sequence of positions 13 to 27 of SEQ ID NO: 4, preferably a base sequence of positions 12 to 27, more preferably a base sequence of positions 11 to 27, more preferably a base sequence of positions 10 to 27, more preferably a base sequence of positions 9 to 27, more preferably a base sequence of positions 8 to 27, more preferably a base sequence of positions 7 to 27, more preferably a base sequence of positions 6 to 27, more preferably a base sequence of positions 5 to 27, more preferably a base sequence of positions 4 to 27, more preferably a base sequence of positions 3 to 27, more preferably a base sequence of positions 2 to 27, and more preferably a base sequence of positions 1 to 27.

The base sequence specifically recognized by the forward primer (3F) of primer pair 3 is preferably a region of positions 27875 to 27889 of SEQ ID NO: 37, more preferably a region of positions 27875 to 27890, more preferably a region of positions 27875 to 27891, more preferably a region of positions 27875 to 27892, more preferably a region of positions 27875 to 27893, more preferably a region of positions 27875 to 27894, more preferably a region of positions 27875 to 27895, more preferably a region of positions 27875 to 27896, more preferably a region of positions 27875 to 27897, more preferably a region of positions 27875 to 27898, more preferably a region of positions 27875 to 27899, more preferably a region of positions 27875 to 27900, more preferably a region of positions 27875 to 27901, and more preferably a region of positions 27875 to 27902.

Specific examples of the 3F primer include oligonucleotides having a base sequence of positions 14 to 28 of SEQ ID NO: 5, preferably a base sequence of positions 13 to 28, more preferably a base sequence of positions 12 to 28, more preferably a base sequence of positions 11 to 28, more preferably a base sequence of positions 10 to 28, more preferably a base sequence of positions 9 to 28, more preferably a base sequence of positions 8 to 28, more preferably a base sequence of positions 7 to 28, more preferably a base sequence of positions 6 to 28, more preferably a base sequence of positions 5 to 28, more preferably a base sequence of positions 4 to 28, more preferably a base sequence of positions 3 to 28, more preferably a base sequence of positions 2 to 28, and more preferably a base sequence of positions 1 to 28.

The base sequence specifically recognized by the reverse primer (3R) of primer pair 3 is preferably a complementary region of positions 24227 to 24213 of SEQ ID NO: 37, more preferably a complementary region of positions 24227 to 24212, more preferably a complementary region of positions 24227 to 24211, more preferably a complementary region of positions 24227 to 24210, more preferably a complementary region of positions 24227 to 24209, more preferably a complementary region of positions 24227 to 24208, more preferably a complementary region of positions 24227 to 24207, more preferably a complementary region of positions 24227 to 24206, more preferably a complementary region of positions 24227 to 24205, more preferably a complementary region of positions 24227 to 24204, more preferably a complementary region of positions 24227 to 24203, more preferably a complementary region of positions 24227 to 24202, more preferably a complementary region of positions 24227 to 24201, and more preferably a complementary region of positions 24227 to 24200.

Specific examples of the 3R primer include oligonucleotides having a base sequence of positions 14 to 28 of SEQ ID NO: 6, preferably a base sequence of positions 13 to 28, more preferably a base sequence of positions 12 to 28, more preferably a base sequence of positions 11 to 28, more preferably a base sequence of positions 10 to 28, more preferably a base sequence of positions 9 to 28, more preferably a base sequence of positions 8 to 28, more preferably a base sequence of positions 7 to 28, more preferably a base sequence of positions 6 to 28, more preferably a base sequence of positions 5 to 28, more preferably a base sequence of positions 4 to 28, more preferably a base sequence of positions 3 to 28, more preferably a base sequence of positions 2 to 28, and more preferably a base sequence of positions 1 to 28.

The base sequence specifically recognized by the forward primer (4F) of primer pair 4 is preferably a region of positions 24247 to 24261 of SEQ ID NO: 37, more preferably a region of positions 24247 to 24262, more preferably a region of positions 24247 to 24263, more preferably a region of positions 24247 to 24264, more preferably a region of positions 24247 to 24265, and more preferably a region of positions 24247 to 24266.

Specific examples of the 4F primer include oligonucleotides having a base sequence of positions 6 to 20 of SEQ ID NO: 7, preferably a base sequence of positions 5 to 20, more preferably a base sequence of positions 4 to 20, more preferably a base sequence of positions 3 to 20, more preferably a base sequence of positions 2 to 20, and more preferably a base sequence of positions 1 to 20.

The base sequence specifically recognized by the reverse primer (4R) of primer pair 4 is preferably a complementary region of positions 18933 to 18919 of SEQ ID NO: 37, more preferably a complementary region of positions 18933 to 18918, more preferably a complementary region of positions 18933 to 18917, more preferably a complementary region of positions 18933 to 18916, more preferably a complementary region of positions 18933 to 18915, more preferably a complementary region of positions 18933 to 18914, more preferably a complementary region of positions 18933 to 18913, and more preferably a complementary region of positions 18933 to 18912.

Specific examples of the 4R primer include oligonucleotides having a base sequence of positions 8 to 22 of SEQ ID NO: 8, preferably a base sequence of positions 7 to 22, more preferably a base sequence of positions 6 to 22, more preferably a base sequence of positions 5 to 22, more preferably a base sequence of positions 4 to 22, more preferably a base sequence of positions 3 to 22, more preferably a base sequence of positions 2 to 22, and more preferably a base sequence of positions 1 to 22.

The base sequence specifically recognized by the forward primer (5F) of primer pair 5 is preferably a region of positions 19226 to 19240 of SEQ ID NO: 37, more preferably a region of positions 19226 to 19241, more preferably a region of positions 19226 to 19242, more preferably a region of positions 19226 to 19243, more preferably a region of positions 19226 to 19244, more preferably a region of positions 19226 to 19245, more preferably a region of positions 19226 to 19246, more preferably a region of positions 19226 to 19247, more preferably a region of positions 19226 to 19248, more preferably a region of positions 19226 to 19249, more preferably a region of positions 19226 to 19250, more preferably a region of positions 19226 to 19251, more preferably a region of positions 19226 to 19252, and more preferably a region of positions 19226 to 19253.

Specific examples of the 5F primer include oligonucleotides having a base sequence of positions 14 to 28 of SEQ ID NO: 9, preferably a base sequence of positions 13 to 28, more preferably a base sequence of positions 12 to 28, more preferably a base sequence of positions 11 to 28, more preferably a base sequence of positions 10 to 28, more preferably a base sequence of positions 9 to 28, more preferably a base sequence of positions 8 to 28, more preferably a base sequence of positions 7 to 28, more preferably a base sequence of positions 6 to 28, more preferably a base sequence of positions 5 to 28, more preferably a base sequence of positions 4 to 28, more preferably a base sequence of positions 3 to 28, more preferably a base sequence of positions 2 to 28, and more preferably a base sequence of positions 1 to 28.

The base sequence specifically recognized by the reverse primer (5R) of primer pair 5 is preferably a complementary region of positions 16698 to 16684 of SEQ ID NO: 37, more preferably a complementary region of positions 16698 to 16683, more preferably a complementary region of positions 16698 to 16682, more preferably a complementary region of positions 16698 to 16681, more preferably a complementary region of positions 16698 to 16680, more preferably a complementary region of positions 16698 to 16679, more preferably a complementary region of positions 16698 to 16678, more preferably a complementary region of positions 16698 to 16677, more preferably a complementary region of positions 16698 to 16676, and more preferably a complementary region of positions 16698 to 16675.

Specific examples of the 5R primer include oligonucleotides having a base sequence of positions 10 to 24 of SEQ ID NO: 10, preferably a base sequence of positions 9 to 24, more preferably a base sequence of positions 8 to 24, more preferably a base sequence of positions 7 to 24, more preferably a base sequence of positions 6 to 24, more preferably a base sequence of positions 5 to 24, more preferably a base sequence of positions 4 to 24, more preferably a base sequence of positions 3 to 24, more preferably a base sequence of positions 2 to 24, and more preferably a base sequence of positions 1 to 24.

The base sequence specifically recognized by the forward primer (6F) of primer pair 6 is preferably a region of positions 16393 to 16407 of SEQ ID NO: 37, more preferably a region of positions 16393 to 16408, more preferably a region of positions 16393 to 16409, more preferably a region of positions 16393 to 16410, more preferably a region of positions 16393 to 16411, more preferably a region of positions 16393 to 16412, more preferably a region of positions 16393 to 16413, more preferably a region of positions 16393 to 16414, more preferably a region of positions 16393 to 16415, more preferably a region of positions 16393 to 16416, more preferably a region of positions 16393 to 16417, and more preferably a region of positions 16393 to 16418.

Specific examples of the 6F primer include oligonucleotides having a base sequence of positions 12 to 26 of SEQ ID NO: 11, preferably a base sequence of positions 11 to 26, more preferably a base sequence of positions 10 to 26, more preferably a base sequence of positions 9 to 26, more preferably a base sequence of positions 8 to 26, more preferably a base sequence of positions 7 to 26, more preferably a base sequence of positions 6 to 26, more preferably a base sequence of positions 5 to 26, more preferably a base sequence of positions 4 to 26, more preferably a base sequence of positions 3 to 26, more preferably a base sequence of positions 2 to 26, and more preferably a base sequence of positions 1 to 26.

The base sequence specifically recognized by the reverse primer (6R) of primer pair 6 is preferably a complementary region of positions 12889 to 12875 of SEQ ID NO: 37, more preferably a complementary region of positions 12889 to 12874, more preferably a complementary region of positions 12889 to 12873, more preferably a complementary region of positions 12889 to 12872, more preferably a complementary region of positions 12889 to 12871, more preferably a complementary region of positions 12889 to 12870, more preferably a complementary region of positions 12889 to 12869, more preferably a complementary region of positions 12889 to 12868, more preferably a complementary region of positions 12889 to 12867, more preferably a complementary region of positions 12889 to 12866, more preferably a complementary region of positions 12889 to 12865, and more preferably a complementary region of positions 12889 to 12864.

Specific examples of the 6R primer include oligonucleotides having a base sequence of positions 12 to 26 of SEQ ID NO: 12, preferably a base sequence of positions 11 to 26, more preferably a base sequence of positions 10 to 26, more preferably a base sequence of positions 9 to 26, more preferably a base sequence of positions 8 to 26, more preferably a base sequence of positions 7 to 26, more preferably a base sequence of positions 6 to 26, more preferably a base sequence of positions 5 to 26, more preferably a base sequence of positions 4 to 26, more preferably a base sequence of positions 3 to 26, more preferably a base sequence of positions 2 to 26, and more preferably a base sequence of positions 1 to 26.

The base sequence specifically recognized by the forward primer (7F) of primer pair 7 is preferably a region of positions 12193 to 12207 of SEQ ID NO: 37, more preferably a region of positions 12193 to 12208, more preferably a region of positions 12193 to 12209, more preferably a region of positions 12193 to 12210, more preferably a region of positions 12193 to 12211, more preferably a region of positions 12193 to 12212, more preferably a region of positions 12193 to 12213, more preferably a region of positions 12193 to 12214, more preferably a region of positions 12193 to 12215, more preferably a region of positions 12193 to 12216, more preferably a region of positions 12193 to 12217, more preferably a region of positions 12193 to 12218, more preferably a region of positions 12193 to 12219, more preferably a region of positions 12193 to 12220, more preferably a region of positions 12193 to 12221, more preferably a region of positions 12193 to 12222, more preferably a region of positions 12193 to 12223, more preferably a region of positions 12193 to 12224, more preferably a region of positions 12193 to 12225, more preferably a region of positions 12193 to 12226, and more preferably a region of positions 12193 to 12227.

Specific examples of the 7F primer include oligonucleotides having a base sequence of positions 21 to 35 of SEQ ID NO: 13, preferably a base sequence of positions 20 to 35, more preferably a base sequence of positions 19 to 35, more preferably a base sequence of positions 18 to 35, more preferably a base sequence of positions 17 to 35, more preferably a base sequence of positions 16 to 35, more preferably a base sequence of positions 15 to 35, more preferably a base sequence of positions 14 to 35, more preferably a base sequence of positions 13 to 35, more preferably a base sequence of positions 12 to 35, more preferably a base sequence of positions 11 to 35, more preferably a base sequence of positions 10 to 35, more preferably a base sequence of positions 9 to 35, more preferably a base sequence of positions 8 to 35, more preferably a base sequence of positions 7 to 35, more preferably a base sequence of positions 6 to 35, more preferably a base sequence of positions 5 to 35, more preferably a base sequence of positions 4 to 35, more preferably a base sequence of positions 3 to 35, more preferably a base sequence of positions 2 to 35, and more preferably a base sequence of positions 1 to 35.

The base sequence specifically recognized by the reverse primer (7R) of primer pair 7 is preferably a complementary region of positions 8534 to 8520 of SEQ ID NO: 37, more preferably a complementary region of positions 8534 to 8519, more preferably a complementary region of positions 8534 to 8518, more preferably a complementary region of positions 8534 to 8517, more preferably a complementary region of positions 8534 to 8516, more preferably a complementary region of positions 8534 to 8515, more preferably a complementary region of positions 8534 to 8514, more preferably a complementary region of positions 8534 to 8513, more preferably a complementary region of positions 8534 to 8512, more preferably a complementary region of positions 8534 to 8511, more preferably a complementary region of positions 8534 to 8510, more preferably a complementary region of positions 8534 to 8509, more preferably a complementary region of positions 8534 to 8508, more preferably a complementary region of positions 8534 to 8507, more preferably a complementary region of positions 8534 to 8506, more preferably a complementary region of positions 8534 to 8505, more preferably a complementary region of positions 8534 to 8504, more preferably a complementary region of positions 8534 to 8503, more preferably a complementary region of positions 8534 to 8502, and more preferably a complementary region of positions 8534 to 8501.

Specific examples of the 7R primer include oligonucleotides having a base sequence of positions 20 to 34 of SEQ ID NO: 14, preferably a base sequence of positions 19 to 34, more preferably a base sequence of positions 18 to 34, more preferably a base sequence of positions 17 to 34, more preferably a base sequence of positions 16 to 34, more preferably a base sequence of positions 15 to 34, more preferably a base sequence of positions 14 to 34, more preferably a base sequence of positions 13 to 34, more preferably a base sequence of positions 12 to 34, more preferably a base sequence of positions 11 to 34, more preferably a base sequence of positions 10 to 34, more preferably a base sequence of positions 9 to 34, more preferably a base sequence of positions 8 to 34, more preferably a base sequence of positions 7 to 34, more preferably a base sequence of positions 6 to 34, more preferably a base sequence of positions 5 to 34, more preferably a base sequence of positions 4 to 34, more preferably a base sequence of positions 3 to 34, more preferably a base sequence of positions 2 to 34, and more preferably a base sequence of positions 1 to 34.

The base sequence specifically recognized by the forward primer (8F) of primer pair 8 is preferably a region of positions 6284 to 6298 of SEQ ID NO: 37, more preferably a region of positions 6284 to 6299, more preferably a region of positions 6284 to 6300, more preferably a region of positions 6284 to 6301, more preferably a region of positions 6284 to 6302, more preferably a region of positions 6284 to 6303, more preferably a region of positions 6284 to 6304, more preferably a region of positions 6284 to 6305, more preferably a region of positions 6284 to 6306, more preferably a region of positions 6284 to 6307, more preferably a region of positions 6284 to 6308, more preferably a region of positions 6284 to 6309, more preferably a region of positions 6284 to 6310, more preferably a region of positions 6284 to 6311, more preferably a region of positions 6284 to 6312, and more preferably a region of positions 6284 to 6313.

Specific examples of the 8F primer include oligonucleotides having a base sequence of positions 16 to 30 of SEQ ID NO: 15, preferably a base sequence of positions 15 to 30, more preferably a base sequence of positions 14 to 30, more preferably a base sequence of positions 13 to 30, more preferably a base sequence of positions 12 to 30, more preferably a base sequence of positions 11 to 30, more preferably a base sequence of positions 10 to 30, more preferably a base sequence of positions 9 to 30, more preferably a base sequence of positions 8 to 30, more preferably a base sequence of positions 7 to 30, more preferably a base sequence of positions 6 to 30, more preferably a base sequence of positions 5 to 30, more preferably a base sequence of positions 4 to 30, more preferably a base sequence of positions 3 to 30, more preferably a base sequence of positions 2 to 30, and more preferably a base sequence of positions 1 to 30.

The base sequence specifically recognized by the reverse primer (8R) of primer pair 8 is preferably a complementary region of positions 3261 to 3247 of SEQ ID NO: 37, more preferably a complementary region of positions 3261 to 3246, more preferably a complementary region of positions 3261 to 3245, more preferably a complementary region of positions 3261 to 3244, more preferably a complementary region of positions 3261 to 3243, more preferably a complementary region of positions 3261 to 3242, more preferably a complementary region of positions 3261 to 3241, more preferably a complementary region of positions 3261 to 3240, more preferably a complementary region of positions 3261 to 3239, more preferably a complementary region of positions 3261 to 3238, more preferably a complementary region of positions 3261 to 3237, more preferably a complementary region of positions 3261 to 3236, and more preferably a complementary region of positions 3261 to 3235.

Specific examples of the 8R primer include oligonucleotides having a base sequence of positions 13 to 27 of SEQ ID NO: 16, preferably a base sequence of positions 12 to 27, more preferably a base sequence of positions 11 to 27, more preferably a base sequence of positions 10 to 27, more preferably a base sequence of positions 9 to 27, more preferably a base sequence of positions 8 to 27, more preferably a base sequence of positions 7 to 27, more preferably a base sequence of positions 6 to 27, more preferably a base sequence of positions 5 to 27, more preferably a base sequence of positions 4 to 27, more preferably a base sequence of positions 3 to 27, more preferably a base sequence of positions 2 to 27, and more preferably a base sequence of positions 1 to 27.

The base sequence specifically recognized by the forward primer (9F) of primer pair 9 is preferably a region of positions 3525 to 3539 of SEQ ID NO: 37, more preferably a region of positions 3525 to 3540, more preferably a region of positions 3525 to 3541, more preferably a region of positions 3525 to 3542, more preferably a region of positions 3525 to 3543, more preferably a region of positions 3525 to 3544, more preferably a region of positions 3525 to 3545, more preferably a region of positions 3525 to 3546, more preferably a region of positions 3525 to 3547, more preferably a region of positions 3525 to 3548, more preferably a region of positions 3525 to 3549, more preferably a region of positions 3525 to 3550, more preferably a region of positions 3525 to 3551, more preferably a region of positions 3525 to 3552, more preferably a region of positions 3525 to 3553, more preferably a region of positions 3525 to 3554, more preferably a region of positions 3525 to 3555, more preferably a region of positions 3525 to 3556, more preferably a region of positions 3525 to 3557, more preferably a region of positions 3525 to 3558, and more preferably a region of positions 3525 to 3559.

Specific examples of the 9F primer include oligonucleotides having a base sequence of positions 21 to 35 of SEQ ID NO: 17, preferably a base sequence of positions 20 to 35, more preferably a base sequence of positions 19 to 35, more preferably a base sequence of positions 18 to 35, more preferably a base sequence of positions 17 to 35, more preferably a base sequence of positions 16 to 35, more preferably a base sequence of positions 15 to 35, more preferably a base sequence of positions 14 to 35, more preferably a base sequence of positions 13 to 35, more preferably a base sequence of positions 12 to 35, more preferably a base sequence of positions 11 to 35, more preferably a base sequence of positions 10 to 35, more preferably a base sequence of positions 9 to 35, more preferably a base sequence of positions 8 to 35, more preferably a base sequence of positions 7 to 35, more preferably a base sequence of positions 6 to 35, more preferably a base sequence of positions 5 to 35, more preferably a base sequence of positions 4 to 35, more preferably a base sequence of positions 3 to 35, more preferably a base sequence of positions 2 to 35, and more preferably a base sequence of positions 1 to 35.

The base sequence specifically recognized by the reverse primer (9R) of primer pair 9 is preferably a complementary region of positions 28 to 14 of SEQ ID NO: 37, more preferably a complementary region of positions 28 to 13, more preferably a complementary region of positions 28 to 12, more preferably a complementary region of positions 28 to 11, more preferably a complementary region of positions 28 to 10, more preferably a complementary region of positions 28 to 9, more preferably a complementary region of positions 28 to 8, more preferably a complementary region of positions 28 to 7, more preferably a complementary region of positions 28 to 6, more preferably a complementary region of positions 28 to 5, more preferably a complementary region of positions 28 to 4, more preferably a complementary region of positions 28 to 3, more preferably a (complementary)? region of positions 28 to 2, and more preferably a complementary region of positions 28 to 1.

Specific examples of the 9R primer include oligonucleotides having a base sequence of positions 14 to 28 of SEQ ID NO: 18, preferably a base sequence of positions 13 to 28, more preferably a base sequence of positions 12 to 28, more preferably a base sequence of positions 11 to 28, more preferably a base sequence of positions 10 to 28, more preferably a base sequence of positions 9 to 28, more preferably a base sequence of positions 8 to 28, more preferably a base sequence of positions 7 to 28, more preferably a base sequence of positions 6 to 28, more preferably a base sequence of positions 5 to 28, more preferably a base sequence of positions 4 to 28, more preferably a base sequence of positions 3 to 28, more preferably a base sequence of positions 2 to 28, and more preferably a base sequence of positions 1 to 28.

The base sequence specifically recognized by the forward primer (10F) of primer pair 10 is preferably a complementary region of positions 25 to 11 of SEQ ID NO: 38, more preferably a complementary region of positions 25 to 10, more preferably a complementary region of positions 25 to 9, more preferably a complementary region of positions 25 to 8, more preferably a complementary region of positions 25 to 7, more preferably a complementary region of positions 25 to 6, more preferably a complementary region of positions 25 to 5, more preferably a complementary region of positions 25 to 4, more preferably a complementary region of positions 25 to 3, more preferably a complementary region of positions 25 to 2, and more preferably a complementary region of positions 25 to 1.

Specific examples of the 10F primer include oligonucleotides having a base sequence of positions 11 to 25 of SEQ ID NO: 19, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the reverse primer (10R) of primer pair 10 is preferably a region of positions 1537 to 1551 of SEQ ID NO: 38, more preferably a region of positions 1537 to 1552, more preferably a region of positions 1537 to 1553, more preferably a region of positions 1537 to 1554, more preferably a region of positions 1537 to 1555, more preferably a region of positions 1537 to 1556, more preferably a region of positions 1537 to 1557, more preferably a region of positions 1537 to 1558, more preferably a region of positions 1537 to 1559, more preferably a region of positions 1537 to 1560, and more preferably a region of positions 1537 to 1561.

Specific examples of the 10R primer include oligonucleotides having a base sequence of positions 11 to 25 of SEQ ID NO: 20, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the forward primer (11F) of primer pair 11 is preferably a complementary region of positions 11432 to 11418 of SEQ ID NO: 38, more preferably a complementary region of positions 11432 to 11417, more preferably a complementary region of positions 11432 to 11416, more preferably a complementary region of positions 11432 to 11415, more preferably a complementary region of positions 11432 to 11414, more preferably a complementary region of positions 11432 to 11413, more preferably a complementary region of positions 11432 to 11412, more preferably a complementary region of positions 11432 to 11411, more preferably a complementary region of positions 11432 to 11410, more preferably a complementary region of positions 11432 to 11409, and more preferably a complementary region of positions 11432 to 11408.

Specific examples of the 11F primer include oligonucleotides having a base sequence of positions 11 to 25 of SEQ ID NO: 21, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the reverse primer (11R) of primer pair 11 is preferably a region of positions 12623 to 12637 of SEQ ID NO: 38, more preferably a region of positions 12623 to 12638, more preferably a region of positions 12623 to 12639, more preferably a region of positions 12623 to 12640, more preferably a region of positions 12623 to 12641, more preferably a region of positions 12623 to 12642, more preferably a region of positions 12623 to 12643, more preferably a region of positions 12623 to 12644, more preferably a region of positions 12623 to 12645, more preferably a region of positions 12623 to 12646, and more preferably a region of positions 12623 to 12647.

Specific examples of the 11R primer include oligonucleotides having a base sequence of positions 11 to 25 of SEQ ID NO: 22, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the forward primer (12F) of primer pair 12 is preferably a complementary region of positions 28901 to 28887 of SEQ ID NO: 38, more preferably a complementary region of positions 28901 to 28886, more preferably a complementary region of positions 28901 to 28885, more preferably a complementary region of positions 28901 to 28884, more preferably a complementary region of positions 28901 to 28883, more preferably a complementary region of positions 28901 to 28882, more preferably a complementary region of positions 28901 to 28881, more preferably a complementary region of positions 28901 to 28880, more preferably a complementary region of positions 28901 to 28879, more preferably a complementary region of positions 28901 to 28878, and more preferably a complementary region of positions 28901 to 28877.

Specific examples of the 12F primer include oligonucleotides having a base sequence of positions 11 to 25 of SEQ ID NO: 23, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the reverse primer (12R) of primer pair 12 is preferably a region of positions 31264 to 31278 of SEQ ID NO: 38, more preferably a region of positions 31264 to 31279, more preferably a region of positions 31264 to 31280, more preferably a region of positions 31264 to 31281, more preferably a region of positions 31264 to 31282, more preferably a region of positions 31264 to 31283, more preferably a region of positions 31264 to 31284, more preferably a region of positions 31264 to 31285, more preferably a region of positions 31264 to 31286, more preferably a region of positions 31264 to 31287, more preferably a region of positions 31264 to 31288, more preferably a region of positions 31264 to 31289, more preferably a region of positions 31264 to 31290, more preferably a region of positions 31264 to 31291, more preferably a region of positions 31264 to 31292, more preferably a region of positions 31264 to 31293, and more preferably a region of positions 31264 to 31294.

Specific examples of the 12R primer include oligonucleotides having a base sequence of positions 17 to 31 of SEQ ID NO: 24, preferably a base sequence of positions 16 to 31, more preferably a base sequence of positions 15 to 31, more preferably a base sequence of positions 14 to 31, more preferably a base sequence of positions 13 to 31, more preferably a base sequence of positions 12 to 31, more preferably a base sequence of positions 11 to 31, more preferably a base sequence of positions 10 to 31, more preferably a base sequence of positions 9 to 31, more preferably a base sequence of positions 8 to 31, more preferably a base sequence of positions 7 to 31, more preferably a base sequence of positions 6 to 31, more preferably a base sequence of positions 5 to 31, more preferably a base sequence of positions 4 to 31, more preferably a base sequence of positions 3 to 31, more preferably a base sequence of positions 2 to 31, and more preferably a base sequence of positions 1 to 31.

The base sequence specifically recognized by the forward primer (13F) of primer pair 13 is preferably a complementary region of positions 35718 to 35704 of SEQ ID NO: 38, more preferably a complementary region of positions 35718 to 35703, more preferably a complementary region of positions 35718 to 35702, more preferably a complementary region of positions 35718 to 35701, more preferably a complementary region of positions 35718 to 35700, more preferably a complementary region of positions 35718 to 35699, more preferably a complementary region of positions 35718 to 35698, more preferably a complementary region of positions 35718 to 35697, more preferably a complementary region of positions 35718 to 35696, more preferably a complementary region of positions 35718 to 35695, and more preferably a complementary region of positions 35718 to 35694.

Specific examples of the 13F primer include oligonucleotides having a base sequence of positions 11 to 25 of SEQ ID NO: 25, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the reverse primer (13R) of primer pair 13 is preferably a region of positions 39836 to 39850 of SEQ ID NO: 38, more preferably a region of positions 39836 to 39851, more preferably a region of positions 39836 to 39852, more preferably a region of positions 39836 to 39853, more preferably a region of positions 39836 to 39854, more preferably a region of positions 39836 to 39855, more preferably a region of positions 39836 to 39856, more preferably a region of positions 39836 to 39857, more preferably a region of positions 39836 to 39858, more preferably a region of positions 39836 to 39859, more preferably a region of positions 39836 to 39860, more preferably a region of positions 39836 to 39861, more preferably a region of positions 39836 to 39862, more preferably a region of positions 39836 to 39863, more preferably a region of positions 39836 to 39864, and more preferably a region of positions 39836 to 39865.

Specific examples of the 13R primer include oligonucleotides having a base sequence of positions 16 to 30 of SEQ ID NO: 26, preferably a base sequence of positions 15 to 30, more preferably a base sequence of positions 14 to 30, more preferably a base sequence of positions 13 to 30, more preferably a base sequence of positions 12 to 30, more preferably a base sequence of positions 11 to 30, more preferably a base sequence of positions 10 to 30, more preferably a base sequence of positions 9 to 30, more preferably a base sequence of positions 8 to 30, more preferably a base sequence of positions 7 to 30, more preferably a base sequence of positions 6 to 30, more preferably a base sequence of positions 5 to 30, more preferably a base sequence of positions 4 to 30, more preferably a base sequence of positions 3 to 30, more preferably a base sequence of positions 2 to 30, and more preferably a base sequence of positions 1 to 30.

The base sequence specifically recognized by the forward primer (14F) of primer pair 14 is preferably a complementary region of positions 44259 to 44245 of SEQ ID NO: 38, more preferably a complementary region of positions 44259 to 44244, more preferably a complementary region of positions 44259 to 44243, more preferably a complementary region of positions 44259 to 44242, more preferably a complementary region of positions 44259 to 44241, more preferably a complementary region of positions 44259 to 44240, more preferably a complementary region of positions 44259 to 44239, more preferably a complementary region of positions 44259 to 44238, more preferably a complementary region of positions 44259 to 44237, more preferably a complementary region of positions 44259 to 44236, and more preferably a complementary region of positions 44259 to 44235.

Specific examples of the 14F primer include oligonucleotides having a base sequence of positions 11 to 25 of SEQ ID NO: 27, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the reverse primer (14R) of primer pair 14 is preferably a region of positions 45415 to 45429 of SEQ ID NO: 38, more preferably a region of positions 45415 to 45430, more preferably a region of positions 45415 to 45431, more preferably a region of positions 45415 to 45432, more preferably a region of positions 45415 to 45433, more preferably a region of positions 45415 to 45434, more preferably a region of positions 45415 to 45435, more preferably a region of positions 45415 to 45436, more preferably a region of positions 45415 to 45437, more preferably a region of positions 45415 to 45438, more preferably a region of positions 45415 to 45439, and more preferably a region of positions 45415 to 45440.

Specific examples of the 14R primer include oligonucleotides having a base sequence of positions 12 to 26 of SEQ ID NO: 28, preferably a base sequence of positions 11 to 26, more preferably a base sequence of positions 10 to 26, more preferably a base sequence of positions 9 to 26, more preferably a base sequence of positions 8 to 26, more preferably a base sequence of positions 7 to 26, more preferably a base sequence of positions 6 to 26, more preferably a base sequence of positions 5 to 26, more preferably a base sequence of positions 4 to 26, more preferably a base sequence of positions 3 to 26, more preferably a base sequence of positions 2 to 26, and more preferably a base sequence of positions 1 to 26.

The base sequence specifically recognized by the forward primer (15F) of primer pair 15 is preferably a complementary region of positions 47754 to 47740 of SEQ ID NO: 38, more preferably a complementary region of positions 47754 to 47739, more preferably a complementary region of positions 47754 to 47738, more preferably a complementary region of positions 47754 to 47737, more preferably a complementary region of positions 47754 to 47736, more preferably a complementary region of positions 47754 to 47735, more preferably a complementary region of positions 47754 to 47734, more preferably a complementary region of positions 47754 to 47733, more preferably a complementary region of positions 47754 to 47732, more preferably a complementary region of positions 47754 to 47731, and more preferably a complementary region of positions 47754 to 47730.

Specific examples of the 15F primer include oligonucleotides having a base sequence of positions 11 to 25 of SEQ ID NO: 29, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the reverse primer (15R) of primer pair 15 is preferably a region of positions 52221 to 52235 of SEQ ID NO: 38, more preferably a region of positions 52221 to 52236, more preferably a region of positions 52221 to 52237, more preferably a region of positions 52221 to 52238, more preferably a region of positions 52221 to 52239, more preferably a region of positions 52221 to 52240, more preferably a region of positions 52221 to 52241, more preferably a region of positions 52221 to 52242, more preferably a region of positions 52221 to 52243, more preferably a region of positions 52221 to 52244, and more preferably a region of positions 52221 to 52245.

Specific examples of the 15R primer include oligonucleotides having a base sequence of positions 11 to 25 of SEQ ID NO: 30, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the forward primer (16F) of primer pair 16 is preferably a complementary region of positions 53806 to 53792 of SEQ ID NO: 38, more preferably a complementary region of positions 53806 to 53791, more preferably a complementary region of positions 53806 to 53790, more preferably a complementary region of positions 53806 to 53789, more preferably a complementary region of positions 53806 to 53788, more preferably a complementary region of positions 53806 to 53787, more preferably a complementary region of positions 53806 to 53786, more preferably a complementary region of positions 53806 to 53785, more preferably a complementary region of positions 53806 to 53784, more preferably a complementary region of positions 53806 to 53783, more preferably a complementary region of positions 53806 to 53782, more preferably a complementary region of positions 53806 to 53781, more preferably a complementary region of positions 53806 to 53780, and more preferably a complementary region of positions 53806 to 53779.

Specific examples of the 16F primer include oligonucleotides having a base sequence of positions 14 to 28 of SEQ ID NO: 31, preferably a base sequence of positions 13 to 28, more preferably a base sequence of positions 12 to 28, more preferably a base sequence of positions 11 to 28, more preferably a base sequence of positions 10 to 28, more preferably a base sequence of positions 9 to 28, more preferably a base sequence of positions 8 to 28, more preferably a base sequence of positions 7 to 28, more preferably a base sequence of positions 6 to 28, more preferably a base sequence of positions 5 to 28, more preferably a base sequence of positions 4 to 28, more preferably a base sequence of positions 3 to 28, more preferably a base sequence of positions 2 to 28, and more preferably a base sequence of positions 1 to 28.

The base sequence specifically recognized by the reverse primer (16R) of primer pair 16 is preferably a region of positions 55288 to 55302 of SEQ ID NO: 38, more preferably a region of positions 55288 to 55303, more preferably a region of positions 55288 to 55304, more preferably a region of positions 55288 to 55305, more preferably a region of positions 55288 to 55306, more preferably a region of positions 55288 to 55307, more preferably a region of positions 55288 to 55308, more preferably a region of positions 55288 to 55309, more preferably a region of positions 55288 to 553010, more preferably a region of positions 55288 to 55311, and more preferably a region of positions 55288 to 55312.

Specific examples of the 16R primer include oligonucleotides having a base sequence of positions 11 to 25 of SEQ ID NO: 32, preferably a base sequence of positions 10 to 25, more preferably a base sequence of positions 9 to 25, more preferably a base sequence of positions 8 to 25, more preferably a base sequence of positions 7 to 25, more preferably a base sequence of positions 6 to 25, more preferably a base sequence of positions 5 to 25, more preferably a base sequence of positions 4 to 25, more preferably a base sequence of positions 3 to 25, more preferably a base sequence of positions 2 to 25, and more preferably a base sequence of positions 1 to 25.

The base sequence specifically recognized by the forward primer (17F) of primer pair 17 is preferably a complementary region of positions 57914 to 57900 of SEQ ID NO: 38, more preferably a complementary region of positions 57914 to 57899, more preferably a complementary region of positions 57914 to 57898, more preferably a complementary region of positions 57914 to 57897, more preferably a complementary region of positions 57914 to 57896, more preferably a complementary region of positions 57914 to 57895, more preferably a complementary region of positions 57914 to 57894, more preferably a complementary region of positions 57914 to 57893, more preferably a complementary region of positions 57914 to 57892, more preferably a complementary region of positions 57914 to 57891, more preferably a complementary region of positions 57914 to 57890, more preferably a complementary region of positions 57914 to 57889, more preferably a complementary region of positions 57914 to 57888, more preferably a complementary region of positions 57914 to 57887, more preferably a complementary region of positions 57914 to 57886, and more preferably a complementary region of positions 57914 to 57885.

Specific examples of the 17F primer include oligonucleotides having a base sequence of positions 16 to 30 of SEQ ID NO: 33, preferably a base sequence of positions 15 to 30, more preferably a base sequence of positions 14 to 30, more preferably a base sequence of positions 13 to 30, more preferably a base sequence of positions 12 to 30, more preferably a base sequence of positions 11 to 30, more preferably a base sequence of positions 10 to 30, more preferably a base sequence of positions 9 to 30, more preferably a base sequence of positions 8 to 30, more preferably a base sequence of positions 7 to 30, more preferably a base sequence of positions 6 to 30, more preferably a base sequence of positions 5 to 30, more preferably a base sequence of positions 4 to 30, more preferably a base sequence of positions 3 to 30, more preferably a base sequence of positions 2 to 30, and more preferably a base sequence of positions 1 to 30.

The base sequence specifically recognized by the reverse primer (17R) of primer pair 17 is preferably a region of positions 60808 to 60822 of SEQ ID NO: 38, more preferably a region of positions 60808 to 60823, more preferably a region of positions 60808 to 60824, more preferably a region of positions 60808 to 60825, more preferably a region of positions 60808 to 60826, more preferably a region of positions 60808 to 60827, more preferably a region of positions 60808 to 60828, more preferably a region of positions 60808 to 60829, more preferably a region of positions 60808 to 60830, more preferably a region of positions 60808 to 60831, more preferably a region of positions 60808 to 60832, and more preferably a region of positions 60808 to 60833.

Specific examples of the 17R primer include oligonucleotides having a base sequence of positions 12 to 26 of SEQ ID NO: 34, preferably a base sequence of positions 11 to 26, more preferably a base sequence of positions 10 to 26, more preferably a base sequence of positions 9 to 26, more preferably a base sequence of positions 8 to 26, more preferably a base sequence of positions 7 to 26, more preferably a base sequence of positions 6 to 26, more preferably a base sequence of positions 5 to 26, more preferably a base sequence of positions 4 to 26, more preferably a base sequence of positions 3 to 26, more preferably a base sequence of positions 2 to 26, and more preferably a base sequence of positions 1 to 26.

The base sequence specifically recognized by the forward primer (18F) of primer pair 18 is preferably a complementary region of positions 67328 to 67314 of SEQ ID NO: 38, more preferably a complementary region of positions 67328 to 67313, more preferably a complementary region of positions 67328 to 67312, more preferably a complementary region of positions 67328 to 67311, more preferably a complementary region of positions 67328 to 67310, more preferably a complementary region of positions 67328 to 67309, more preferably a complementary region of positions 67328 to 67308, more preferably a complementary region of positions 67328 to 67307, more preferably a complementary region of positions 67328 to 67306, more preferably a complementary region of positions 67328 to 67305, more preferably a complementary region of positions 67328 to 67304, and more preferably a complementary region of positions 67328 to 67303.

Specific examples of the 18F primer include oligonucleotides having a base sequence of positions 12 to 26 of SEQ ID NO: 35, preferably a base sequence of positions 11 to 26, more preferably a base sequence of positions 10 to 26, more preferably a base sequence of positions 9 to 26, more preferably a base sequence of positions 8 to 26, more preferably a base sequence of positions 7 to 26, more preferably a base sequence of positions 6 to 26, more preferably a base sequence of positions 5 to 26, more preferably a base sequence of positions 4 to 26, more preferably a base sequence of positions 3 to 26, more preferably a base sequence of positions 2 to 26, and more preferably a base sequence of positions 1 to 26.

The base sequence specifically recognized by the reverse primer (18R) of primer pair 18 is preferably a region of positions 68792 to 68806 of SEQ ID NO: 38, more preferably a region of positions 68792 to 68807, more preferably a region of positions 68792 to 68808, more preferably a region of positions 68792 to 68809, more preferably a region of positions 68792 to 68810, more preferably a region of positions 68792 to 68811, more preferably a region of positions 68792 to 68812, more preferably a region of positions 68792 to 68813, more preferably a region of positions 68792 to 68814, more preferably a region of positions 68792 to 68815, more preferably a region of positions 68792 to 68816, more preferably a region of positions 68792 to 68817, and more preferably a region of positions 68792 to 68818.

Specific examples of the 18R primer include oligonucleotides having a base sequence of positions 13 to 27 of SEQ ID NO: 36, preferably a base sequence of positions 12 to 27, more preferably a base sequence of positions 11 to 27, more preferably a base sequence of positions 10 to 27, more preferably a base sequence of positions 9 to 27, more preferably a base sequence of positions 8 to 27, more preferably a base sequence of positions 7 to 27, more preferably a base sequence of positions 6 to 27, more preferably a base sequence of positions 5 to 27, more preferably a base sequence of positions 4 to 27, more preferably a base sequence of positions 3 to 27, more preferably a base sequence of positions 2 to 27, and more preferably a base sequence of positions 1 to 27.

Specific base sequences of the 1F to 18R primers mentioned above as examples can specifically recognize the corresponding specific recognition regions under PCR conditions. Preferably, as long as the primers used in a single reaction vessel are not annealed to each other or self-annealed, one or several bases may be replaced with other bases, or one or several bases may be added to the 3'-end or 5'-end. The term "several" as used herein refers to, for example, 2 or 3. When one or several bases are added to the primer, adding such bases to the 5'-end of the primer is preferable. In a preferable embodiment, the 1F to 18R primers preferably comprise, as the 3'-terminal sequence, the specific base sequences described above for the primers.

The base sequences obtained by replacing one or several bases in specific base sequences of the 1F to 18R primers with other bases preferably are at least 70%, more preferably at least 75%, still more preferably at least 80%, even more preferably at least 85%, still even more preferably at least 90%, and further still even more preferably at least 95% identical to the base sequences before the replacement (i.e., the base sequences set forth in SEQ ID NOs.).

When one or several bases in specific base sequences of the 1F to 18R primers are replaced with other bases, the following bases are preferably not replaced: bases at positions 27 and 23 of the base sequence set forth in SEQ ID NO: 4, (the 2R primer); bases at positions 28 and 9 of the base sequence set forth in SEQ ID NO: 5, (the 3F primer); base at position 20 of the base sequence set forth in SEQ ID NO: 7 (the 4F primer); base at position 22 of the base sequence set forth in SEQ ID NO: 8 (the 4R primer); base at position 24 of the base sequence set forth in SEQ ID NO: 10 (the 5R primer); bases at positions 26, 23, 11, and 2 of the base sequence set forth in SEQ ID NO: 12 (the 6R primer); and bases at positions 35 and 34 of the base sequence set forth in SEQ ID NO: 13 (the 7F primer).

The length of each primer is not particularly limited as long as each primer can specifically recognize the corresponding specific recognition region, and hybridization between primers does not occur. The length of each primer is preferably 15 bases or more and 40 bases or less. More preferably, the lower limit of each primer length is 16 bases or more, still more preferably 17 bases or more, and even more preferably 18 bases or more. More preferably, the upper limit of each primer length is 39 bases or less, still more preferably 38 bases or less, or even more preferably 37 bases or less.

In terms of amplifying all the exons of PKD1 and PKD2 genes under a single set of PCR conditions, the primers contained in each primer set preferably have Tm values whose difference is small. For example, the difference between Tm values of the primers contained in each primer set is preferably 5° C. or less, preferably 4° C. or less, and still more preferably 3.6° C. or less.

The above 1F to 18R primers are preferably designed according to the base sequence of the region specifically recognized by each primer. For example, each primer preferably has a GC content of about 40 to 75% and is designed in such a manner that the primers used within a single reaction vessel do not anneal with each other (for example, the primers do not have a complementary sequence of 3 bases or more at the 3'-end) and/or do not include a self-complementary sequence.

The region amplified by primer pair 1 contains exon 1 of the PKD1 gene. The region amplified by primer pair 2 contains exons 2 to 8 of the PKD1 gene. The region amplified by primer pair 3 contains exons 9 to 13 of the PKD1 gene. The region amplified by primer pair 4 contains exons 14 to 16 of the PKD1 gene. The region amplified by primer pair 5 contains exons 17 to 21 of the PKD1 gene. The region amplified by primer pair 6 contains exons 22 to 26 of the PKD1 gene. The region amplified by primer pair 7 contains exons 27 to 34 of the PKD1 gene. The region amplified by primer pair 8 contains exons 35 to 41 of the PKD1 gene. The region amplified by primer pair 9 contains exons 41 to 46 of the PKD1 gene.

The region amplified by primer pair 10 contains exon 1 of the PKD2 gene. The region amplified by primer pair 11 contains exon 2 of the PKD2 gene. The region amplified by a primer pair 12 contains exons 3 and 4 of the PKD2 gene. The region amplified by primer pair 13 contains exons 5 and 6 of the PKD2 gene. The region amplified by primer pair 14 contains exon 7 of the PKD2 gene. The region amplified by primer pair 15 contains exons 8 and 9 of the PKD2 gene. The region amplified by primer pair 16 contains exon 10 of the PKD2 gene. The region amplified by primer pair 2 contains exons 11 to 13 of the PKD2 gene. The region amplified by primer pair 18 contains exons 14 and 15 of the PKD2 gene.

Accordingly, to amplify all the exons of the PKD1 gene, a primer set comprising primer pairs 1 to 9 can be utilized. When not all the exons of the PKD1 gene have to be amplified, only the primer pairs necessary for amplifying the desired exons are selected and can be used in combination. Similarly, to amplify all the exons of the PKD2 gene, a primer set comprising primer pairs 10 to 18 can be utilized. When not all the exons of the PKD2 gene have to be amplified, only the primer pairs necessary for amplifying the desired exons are selected and can be used in combination. Accordingly, a primer set comprising any combination of primer pairs 1 to 18 according to the intended purpose of use can be designed. Further, when an additional PCR as described later is to be performed, the primer pair set may further comprise a primer pair used in the additional PCR.

The oligonucleotides used as primers can be chemically synthesized. For example, it is efficient to synthesize such oligonucleotides by using a general-purpose DNA synthesizer. The 1F to 18R primers can be stored in any state. For example, the 1F to 18R primers can be stored in a dried or lyophilized state, or in a solution suitable for use in PCR (e.g., a buffer). The solution containing a primer may contain a stabilizer for primers, etc., if necessary.

The 1F to 18R primers or any combination of the primers can be combined with a reagent for use in PCR and/or a container for use in PCR, etc., to provide a kit. For example, a kit provided by combining heat-resistant DNA polymerase, deoxyribonucleotide, magnesium, a buffer for PCR, a preservation container capable of appropriately preserving the quality of such materials, etc., can be provided. The primers contained in the kit may be individually contained in containers, or primer pairs may be contained in individual containers, or each set of primer pairs as described below may be contained in an individual container. When an additional PCR is to be performed as described below, the kit may further contain a primer pair used in the additional PCR.

2. Method for Amplifying Exons of PKD1 Gene and/or PKD2 Gene

PCR is performed using one of primer pairs 1 to 18 or any combination of the primer pairs to amplify the desired exons of the PKD1 gene and/or the PKD2 gene. PCR can be performed according to usual methods. For example, PCR can be performed using a commercially available PCR device and a long-range PCR kit, etc., according to the manual. More specifically, PCR may comprise one of, any combination of, or all of the following steps (1) to (5). The following steps (3) and (4) can be performed under the same temperature conditions. In one embodiment of the present invention, steps (3) and (4) are preferably performed under the same temperature conditions simultaneously (continuously).

(1) A step of preparing a reaction mixture comprising template DNA, a primer pair, heat-resistant DNA polymerase, and a nucleotide comprising adenine, guanine, thymine, and cytosine;

(2) a heat denaturation step of heating a reaction mixture to a predetermined temperature and dissociating the double-stranded template DNA into single strands;

(3) an annealing step of cooling the reaction mixture to a predetermined temperature and binding primers constituting the primer pair to the respective specific recognition regions in the single-stranded template DNA;

(4) an elongation step of maintaining the reaction mixture at a predetermined temperature and synthesizing DNA complementary to the template DNA by elongation from the primers; and/or (5) a step of repeating steps (2) to (4) until predetermined amounts of amplification products (DNAs corresponding to the desired exons) are obtained.

Human genomic DNA is preferably used as the template DNA. Human genomic DNA can be easily obtained from the blood or any other tissue sampled from a subject by using a commercially available DNA extraction kit or the like. Although the subject is not particularly limited, examples of preferable subjects include humans suspected to have developed polycystic kidney disease or humans who have genetically relatively high probability that a mutation exists in the PKD1 or PKD2 gene.

Any PCR reaction mixture and heat-resistant DNA polymerase may be used. For example, those contained in a commercially available PCR kit can be used. As the reaction mixture, any buffer known to be usually used for PCR can be used. Examples include a Tris-HCl buffer, a Tris-sulfuric acid buffer, a tricine buffer, and the like. Examples of heat-resistant polymerases include Taq DNA polymerase (e.g., FastStart Taq DNA Polymerase (Roche), Ex Taq (registered trademark) (Takara), Z-Taq, AccuPrime Taq DNA Polymerase, M-PCR kit (QIAGEN), KOD DNA polymerase, and the like.

The amounts of the primer and template DNA used, etc., can be adjusted according to the PCR kit and device used. The primers are usually added to a concentration of 0.1 to 0.5 μM in the PCR reaction mixture. Human genomic DNA used as a template may be added, for example, in an amount of about 25 to 150 ng to 50 μl of the reaction solution.

The PCR cycling conditions are not particularly limited as long as the desired exons of the PKD1 and PKD2 genes can be amplified. For example, the thermal denaturation temperature can be set to 92 to 100° C., and preferably 94 to 98° C. The thermal denaturation time can be set to, for example, 5 to 180 seconds, and preferably 10 to 130 seconds. The annealing temperature for hybridizing primers can be set to, for example, 62 to 80° C., and preferably 64 to 78° C. The annealing time can be set to, for example, 10 to 60 seconds, and preferably 20 to 30 seconds. The extension reaction temperature can be set to, for example, 62 to 80° C., and preferably 64 to 78° C. The elongation reaction time can be set to, for example, 4 to 15 minutes, and preferably 4 to 10 minutes. The annealing and extension reaction can be performed under the same conditions. The operation of combining thermal denaturation, annealing, and an elongation reaction is defined as one cycle. This cycle can be repeated until the required amounts of amplification products are obtained. For example, the number of cycles can be set to 30 to 40 times, and preferably about 30 to 35 times.

In the present specification, the “PCR cycling conditions” include one of, any combination of, or all of the conditions with respect to the temperature and time of each thermal denaturation, annealing, and elongation reaction of PCR and the number of cycles. When PCR cycling conditions are set, the touchdown PCR method is also preferable in terms of inhibiting non-specific amplification as described in the Examples below. Touchdown PCR is a technique in which the first annealing temperature is set to a relatively high temperature and the annealing temperature is gradually reduced for each cycle, and, midway and thereafter, PCR is performed in the same manner as general PCR. Shuttle PCR is also preferable in terms of inhibiting non-specific amplification. Shuttle PCR is a PCR in which annealing and extension reaction are performed at the same temperature.

Although different PCR cycling conditions can be used for each primer pair, it is preferable from the viewpoint of operation and efficiency that PCR cycling conditions are set in such a manner that the same PCR cycling conditions can be used for different primer pairs and the variation of PCR cycling conditions used to obtain necessary amplification products is minimized. The number of variations of PCR cycling conditions is preferably 5 or less, more preferably 4 or less, still more preferably 3 or less, even more preferably 2 or less, and even still more preferably 1. When the number of variations of PCR cycling conditions used to obtain all the necessary amplification products is reduced, PCRs using the same PCR cycling conditions can be simultaneously performed using one PCR device. Accordingly, the desired amplification products can be obtained in a short time using smaller amounts of resources.

Although PCR may be performed in a different reaction vessel for each primer pair, performing PCR using multiple different primer pairs in a single reaction vessel (multiplex PCR) is preferable in terms of operating ease and efficiency. When PCR is performed using different primer pairs in a single reaction vessel, care should be taken so that annealing does not occur between primers. From this viewpoint, examples of preferable combinations of primer pairs that are preferably used in a single reaction vessel include the following (A) to (G):

Combination (A): primer pair 2 and primer pair 12;
Combination (B): primer pair 4 and primer pair 17;
Combination (C): primer pair 6 and primer pair 15;
Combination (D): primer pair 1, primer pair 6 and/or primer pair 15;
Combination (E): primer pair 3, primer pair 8 and/or primer pair 18;
Combination (F): primer pair 7, primer pair 13 and/or primer pair 16; and
Combination (G): primer pair 10, primer pair 11 and/or primer pair 14.

Combination (D) is a set of primer pair 1, primer pair 5 and/or primer pair 9. Preferably, combination (D) is composed of primers 1, 5, and 9. Combination (F) is a set of primer pair 7, primer pair 13 and/or primer pair 17. Preferably, combination (F) is composed of primer pairs 7, 13, and 17. Combination (G) is a set of primer pair 10, primer pair 11 and/or primer pair 14. Preferably, combination (G) is composed of primer pairs 10, 11, and 14.

Not all the above combinations (A) to (G) have to be used. The combinations can be suitably selected according to the purpose of use. For example, at least one combination selected from the group consisting of combinations (A) to (G) can be used, preferably 2 or more combinations, more preferably 3 or more combinations, still more preferably 4 or more combinations, even more preferably 5 or more combinations, still even more preferably 6 or more combinations, and most preferably all of the combinations can be used. If individual PCR reaction vessels (e.g., tubes) are prepared for all the primer pairs, 18 PCR reaction vessels are necessary. When combinations (A) to (G) are all used, the number of reaction vessels required can be reduced to 7. Reducing the number of reaction vessels required is preferable because it is not only economical but also can increase the number of specimens amplified at once.

The regions including all the exons of PKD1 and PKD2 genes can be amplified by performing PCR using primer pairs 1 to 18 and human genomic DNA as a template. If necessary, a further PCR can be performed in combination. For example, sufficient amounts of amplification products may not be uniformly obtained depending on the DNA polymerase used in PCR, the PCR device, the GC content in the amplifying region, the size of the amplified region, and the PCR cycling conditions. In such a case, depending on the means for analyzing the amplification products, further amplification may be desirable. If necessary, additional PCR can be performed.

For example, since the region amplified by primer pair 1 has a relatively high GC content, simultaneously performing PCR under the same PCR cycling conditions as other primer pairs may result in a relatively small amount of amplification product obtained by primer pair 1. In this case, the amount of amplification may be preferably adjusted by further performing PCR using as a template an amplification product obtained by primer pair 1, depending on the type of the next-generation sequencer used in sequence analysis. The primers for use in PCR using as a template an amplification product obtained by primer pair 1 are not particularly limited, and any primers can be designed.

Additional PCR can be performed by using a commercially available PCR device, a PCR reagent, etc. Any PCR cycling conditions can be used for additional PCR. The PCR cycling conditions for additional PCR can be suitably set according to the amplified region, the primers used, the type of reagent, etc. For example, the same PCR cycling conditions as those for PCR using the above primer pairs 1 to 19 or improved conditions thereof can be used.

The analysis of base sequences of the amplification products obtained by PCR can determine whether a mutation (genetic polymorphism) exists in the PKD1 and PKD2 genes of the subject. The analysis of the base sequences can be performed using known sequencing techniques. For examples, since the Sanger method, the DHPLC (denaturing high-pressure liquid chromatography) method, the mutation detection method, which is a combination of endonuclease and DHPLC, and a method for detecting a mutation in the PKD1 and PKD2 genes using a next-generation sequencer are known, the existence of a mutation can be detected by using these methods. Before the base sequence analysis, the amplification products can be concentrated, if necessary. The amplification can be performed, for example, by fragmenting amplification products and preparing libraries and using emulsion PCR. The concentration of the amplification products can be performed, for example, by a technique called solid phase amplification (bridge amplification).

When a genetic polymorphism is detected from the analysis of base sequences, the subject can be determined to have a high risk of developing polycystic kidney disease. For a subject suspected to have developed polycystic kidney disease, the existence of a genetic polymorphism can be used for diagnosis of the onset of polycystic kidney disease. Further, when a genetic polymorphism is confirmed to exist in the PKD1 gene, the result can be used to determine that progression of polycystic kidney disease (when developed) is relatively fast. When the subject is determined to have developed polycystic kidney disease or have a high risk of developing polycystic kidney disease, the subject can receive appropriate therapy or treatment so as to delay aggravation of the condition or development of the disease.

EXAMPLES

The present invention is described in further detail with reference to Examples and Comparative Examples. However, the scope of the invention is not limited to these Examples.

1. Subjects

Tests were performed using 140 samples collected from healthy (male and female) adults 35 years of age or older, who had no kidney cysts in ultrasound examination and who were definitely not predisposed to PKD. In this specification, the analytic results of 6 out of 140 samples are shown as representative examples. The DNA samples were collected in the following manner. 7 mL of peripheral blood collected from each healthy adult was placed in a vacuum blood sampling tube. After gentle end-over-end mixing was performed two or three times, the samples in the sampling tubes were frozen and stored in a freezer of a blood sampling facility. Genomic DNA was extracted from the cryopreserved blood using a QIAamp DNA Blood Maxi kit (a product of QIAGEN K.K.). The obtained genomic DNA was used as sample DNA.

2. Designing and Mixing of Primers

Primers for PKD1 gene amplification (9 pairs) and primers for PKD2 gene amplification (9 pairs), which have base sequences shown in Tables 2 and 3 below, were designed and synthesized.

TABLE 2

| | Primer | | | | | Amplification region | | | |
|---|---|---|---|---|---|---|---|---|---|
| Pair No. | No. | Start | End | Sequence (5'→3') | SEQ ID NO: | Exon | Size | From | To |
| 1 | 1F | 48944 | 48916 | GCAGCAGTTTCTTGTGGCTGTTTCTTCCC | SEQ ID NO: 1 | 1 | 2547 | 48944 | 46398 |
| | 1R | 46398 | 46427 | GTTCTCAGGATAGCCTTGGAACCCAATAGC | SEQ ID NO: 2 | | | | |
| 2 | 2F | 31458 | 31431 | GTTTCTCTGGGTTTATGCCTCGAGGTGG | SEQ ID NO: 3 | 2-8 | 3610 | 31458 | 27849 |
| | 2R | 27849 | 27875 | CTGCCTTTCAGGAATAACTCACACACG | SEQ ID NO: 4 | | | | |
| 3 | 3F | 27902 | 27875 | ACATTACCTCCAGGCCTTTTCTCTGAGC | SEQ ID NO: 5 | 9-13 | 3703 | 27902 | 24200 |
| | 3R | 24200 | 24227 | GTTACCTCCCAACAGACAGGGAAACCGA | SEQ ID NO: 6 | | | | |
| 4 | 4F | 24266 | 24247 | CCGAGGGACCCCCACATCAC | SEQ ID NO: 7 | 14-16 | 5356 | 24266 | 18912 |
| | 4R | 18912 | 18933 | CCCTCAGACGACCCCTCTGGGA | SEQ ID NO: 8 | | | | |
| 5 | 5F | 19253 | 19226 | CTGCCACAGTTCCACGTACAGTCTTCAA | SEQ ID NO: 9 | 17-21 | 2579 | 19253 | 16675 |
| | 5R | 16675 | 16698 | CCCTGCGTTCACACAGGACAGAAC | SEQ ID NO: 10 | | | | |
| 6 | 6F | 16418 | 16393 | ATGTGAAGAGGTGCCTTGTGTGGTCG | SEQ ID NO: 11 | 22-26 | 3555 | 16418 | 12864 |
| | 6R | 12864 | 12889 | GCAATGAAGAGGAAAGCAGCACAGAG | SEQ ID NO: 12 | | | | |
| 7 | 7F | 12227 | 12193 | GCCGGGACTGCCTGTGTGGCTCCTTGAGTGCGCAC | SEQ ID NO: 13 | 27-34 | 3727 | 12227 | 8501 |
| | 7R | 8501 | 8534 | CTGGGGCCCTGGGGATCCCATGAGGCTCTTTCCA | SEQ ID NO: 14 | | | | |
| 8 | 8F | 6313 | 6284 | ATATCAGCATGGTGGCCYGATGCAGTGGCA | SEQ ID NO: 15 | 35-41 | 3079 | 6313 | 3235 |
| | 8R | 3235 | 3261 | TAGGCCAGCGGGGGCCGGAGGAGTGAG | SEQ ID NO: 16 | | | | |
| 9 | 9F | 3559 | 3525 | ACGCCAAGGACAAGGGAGTAGTTCTCCAGGAGTGC | SEQ ID NO: 17 | 41-46 | 3559 | 3559 | 1 |
| | 9R | 1 | 28 | CGCCTACTCCAACCCCAGCCTACCTCTG | SEQ ID NO: 18 | | | | |

(Table of Primers for PKD1)

TABLE 3

| | Primer | | | | | Amplification region | | | |
|---|---|---|---|---|---|---|---|---|---|
| Pair No. | No. | Start | End | Sequence (5'→3') | SEQ ID NO: | Exon | Size | From | To |
| 10 | 10F | 1 | 25 | AAGTGGCTGGTGGATAACTGGGACC | SEQ ID NO: 19 | 1 | 1561 | 1 | 1561 |
| | 10R | 1561 | 1537 | TGACAATCTGCCACACTCCTCCCAC | SEQ ID NO: 20 | | | | |
| 11 | 11F | 11408 | 11432 | TCATCTTCACTCAGCCAGCCCAACG | SEQ ID NO: 21 | 2 | 1240 | 11408 | 12647 |
| | 11R | 12647 | 12623 | GCCTCTCCCGTCCTGTGTTAAACGC | SEQ ID NO: 22 | | | | |
| 12 | 12F | 28877 | 28901 | TGTGAATGTGTGCCGGTTCCCTTGG | SEQ ID NO: 23 | 3-4 | 2418 | 28877 | 31294 |
| | 12R | 31294 | 31264 | GGGAATGAATGAATGAATGGTGGGAGTTCAG | SEQ ID NO: 24 | | | | |
| 13 | 13F | 35694 | 35718 | GGTTCCCGAGTCTGCCCTCAAAAGC | SEQ ID NO: 25 | 5-6 | 4172 | 35694 | 39865 |
| | 13R | 39865 | 39836 | CCTCCACATCTCATACGGCATACTAAAGCC | SEQ ID NO: 26 | | | | |
| 14 | 14F | 44235 | 44259 | TGGCTGGCAATTGGAGAATGCAGAG | SEQ ID NO: 27 | 7 | 1206 | 44235 | 45440 |
| | 14R | 45440 | 45415 | CCAGGCCCAGCTAACACACTGAAAGG | SEQ ID NO: 28 | | | | |

TABLE 3-continued

| Primer | | | | | | | | | |
|---|---|---|---|---|---|---|---|---|---|
| Pair | | | | | | Amplification region | | | |
| No. | No. | Start | End | Sequence (5'→3') | SEQ ID NO: | Exon | Size | From | To |
| 15 | 15F | 47730 | 47754 | CAATCTGGGCAGCCATCCTCAGTGC | SEQ ID NO: 29 | 8-9 | 4516 | 47730 | 52245 |
| | 15R | 52245 | 52221 | TGAGCCTTTCCAGTTGCCACGACTC | SEQ ID NO: 30 | | | | |
| 16 | 16F | 53779 | 53806 | AGGCCTGCTGTATTCCTATTTGCAACAG | SEQ ID NO: 31 | 10 | 1534 | 53779 | 55312 |
| | 16R | 55312 | 55288 | ACAAAGAGGCCCAACTTTCCTGTCC | SEQ ID NO: 32 | | | | |
| 17 | 17F | 57885 | 57914 | ACCCTGACTTTTTCCATGTAACTGTTCCAC | SEQ ID NO: 33 | 11-13 | 2949 | 57885 | 60833 |
| | 17R | 60833 | 60808 | ACTGCCTGGTCTCATGTGGACTCTTG | SEQ ID NO: 34 | | | | |
| 18 | 18F | 67303 | 67328 | AAGACTTCTGATACGCGCTGACTTGC | SEQ ID NO: 35 | 14-15 | 1516 | 67303 | 68818 |
| | 18R | 68818 | 68792 | ATGCCCCATTTTCCTTCACACTCTTGG | SEQ ID NO: 36 | | | | |

(Table of Primers for PKD2)

In Tables 2 and 3, the numbers in the "Start" column indicate the positions of bases on chromosomal DNA (in Table 2, the base sequence set forth in SEQ ID NO: 37; in Table 3, the base sequence shown in SEQ ID NO: 38) with which the 5'-terminal base of each primer is hybridized. Similarly, the numbers in the "End" column indicate the positions of bases on chromosal DNA with which the 3'-terminal base of each primer is hybridized. The numbers in the "Exon" column indicate exon No. contained in the region amplified by each primer pair. The numbers in the "Size" column indicate the size of the amplified region (number of bases). The numbers in the "From" column indicate the positions of bases on chromosomal DNA to which the 5'-terminal base of each primer corresponds. The numbers in the "To" column indicate the positions of bases on chromosal DNA with which the 3'-terminal base of each amplified region corresponds.

Solutions containing primers shown in Tables 2 and 3 in a concentration of 30 μM were prepared and these were mixed in a combination shown in Table 4 below. The primer mix for Multiplex PCR was prepared.

TABLE 4

| Primer Mix | |
|---|---|
| No. | Primer Pair No. |
| A | 2, 12 |
| B | 4, 17 |
| C | 6, 15 |
| D | 1, 5, 9 |
| E | 3, 8, 18 |
| F | 7, 13, 16 |
| G | 10, 11, 14 |

3. Multiplex PCR

Ten kinds of specimen DNA from healthy adults obtained above in section 1 were subjected to multiplex PCR in a thermal cycler (Veriti 96-Well Thermal Cycler, a product of Life Technologies) using the primer mix prepared above in section 2 and a reagent for Multiplex PCR (SequalPrep Long PCR Kit with dNTPs, a product of Life Technologies). Specifically, multiplex PCR was performed in the following manner. A buffer, DMSO, an enhancer, DNA synthetase, sterile water, a primer mix, and Template DNA (specimen DNA) were added to a reaction vessel. Since 7 kinds of primer mixes (A to G) were used, 7 wells were used per specimen and one of the primer mixes was placed in each well. The template DNA was added in an amount of 100 ng to each well, and the total volume of the reaction mixture was adjusted to 50 μL per well. Table 5 below shows the composition of each reaction mixture.

TABLE 5

| Reagent | Final Concentration |
|---|---|
| 10 X Reaction Buffer | 1 x |
| DMSO | 2% |
| 10 X Enhancer A | 0.5 x |
| Long Polymerase | 1 U |
| Primer mix | 0.2 μM |
| $dH_2O$ | Appropriate amount |

Figure 2:
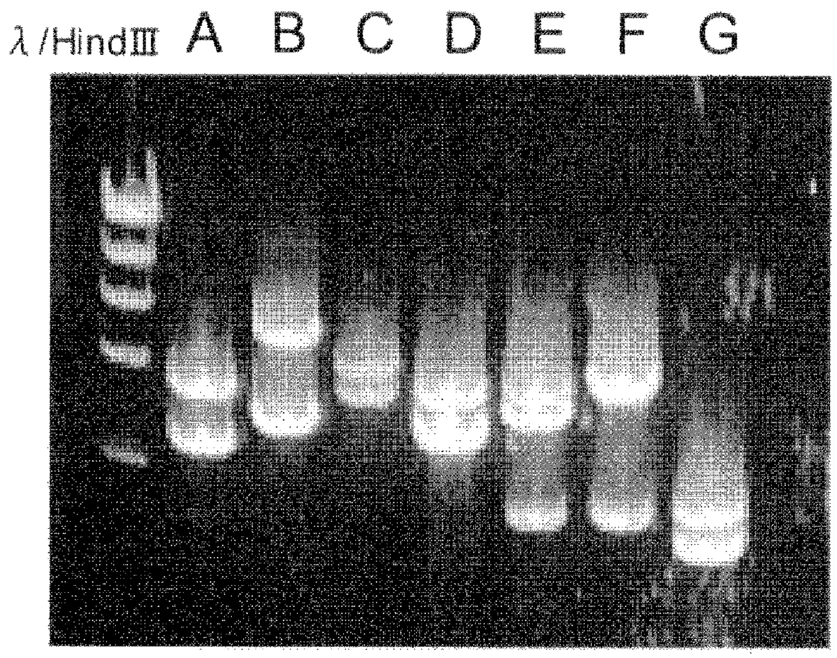
FIG. 2 shows a photograph of the electrophoresis of multiplex PCR amplification products using 1% agarose gel. Two bands were recognized in the amplification products obtained using primer mixes A, B, and C. Three bands were recognized in the amplification product obtained using primer mix E. Since the amplification products obtained using primer mixes D, F, and G include two amplification products of similar sizes, two bands were recognized.

PCR was performed under the conditions shown in FIG. 1. More specifically, a double-stranded template DNA was thermally denatured by heating at 94° C. for 2 minutes using a thermal cycler. Subsequently, after thermal denaturation at 98° C. for 10 seconds, an annealing reaction and an extension reaction were performed at 74° C. for 5 minutes. This operation was further repeated twice with the annealing temperature being reduced by 2° C. per operation. Thereafter, 30 cycles of a cycled reaction comprising thermal denaturation at 98° C. for 10 seconds and then a reaction at 68° C. for 5 minutes were performed. Finally, a reaction was allowed to proceed at 68° C. for 7 minutes to complete the entire reaction. The existence and size of each obtained amplification product were confirmed by electrophoresis using 1% agarose gel (FIG. 2). In electrophoresis, λ/HindIII digest was used as a molecular marker. Further, each amplification product was purified by using a magnetic bead purification reagent (Agencourt AmpureXP, a product of Beckman Coulter) and dissolved in 40 uL of purified water. The concentration of each amplification product was measured by using an ultra-trace UV-Visible spectrophotometer (Nanodrop, a product of Thermo Scientific). The measured concentration of the smallest amplification product was 21.7 ng/μL and that of the largest amplification product was 92.1 ng/μL.

4. Library Preparation

Seven kinds of amplification product mixtures per specimen were obtained by the multiplex PCR described above in section 3. Aliquots of 3 μL of the amplification products were placed together into one tube. The samples thus obtained by placing the amplification products together per specimen were passed through a column to purify the amplification products. The concentrations were then measured and adjusted to 0.2 ng/μL. Using a DNA fragment library preparation kit (Nextera XT DNA Sample Prep Kit, a product of Illumina), the samples having the adjusted concentration were fragmented, and barcode sequences were added. The concentration was equalized among the samples.

5. Analysis Using the Next-Generation Sequencer

The samples for which library preparation had been completed were pretreated using a sequencing kit (MiSeq Reagent Kit v2 2×150 bp, a product of Illumina) and sequencing was performed using a next-generation sequencer (MiSeq, a product of Illumina). Mutation detection was performed based on the obtained sequence data. As a result, the existence of 11 to 25 polymorphic mutations was confirmed per sample. It was thus confirmed that polymorphic mutations (SNP, insertion, and deletion) in the PKD genes can be detected by using the libraries prepared by the multiplex PCR method using the above primers.

6. Mapping Result

About several hundreds of thousands of the DNA fragments (reads) comprising about several hundred bases in length, which were output by the next generation sequencer, were mapped to the reference sequence and the overall states were visualized by using a viewer software (Integrative Genomics Viewer: IGV). The results revealed that only the regions of PKD1 and PKD2 genes subjected to multiplex PCR were mapped and the DNA fragments were not affected by pseudogenes.

7. Comparison with the PKD1 Gene Sequence Obtained Using the Sanger Method

Figures 1, 3:
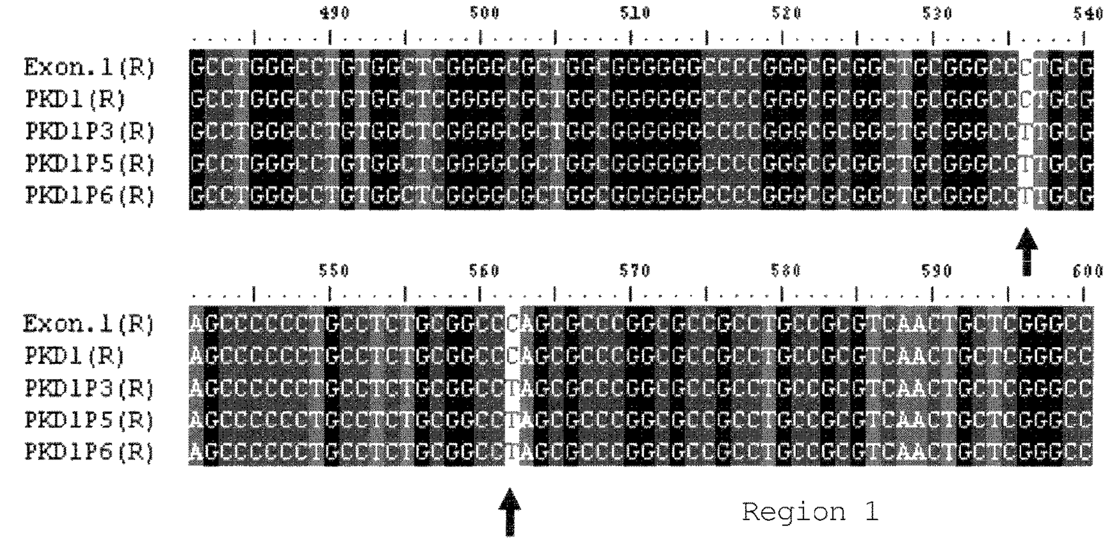
Figures 2, 3:
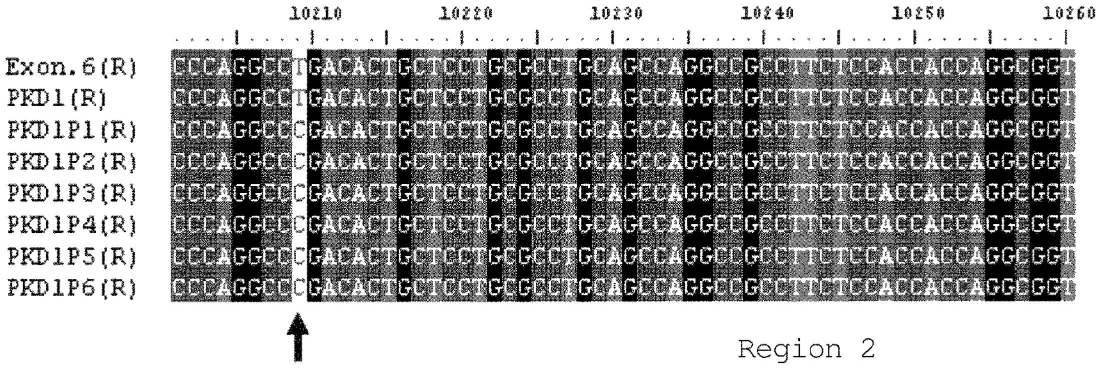
Figure 3:
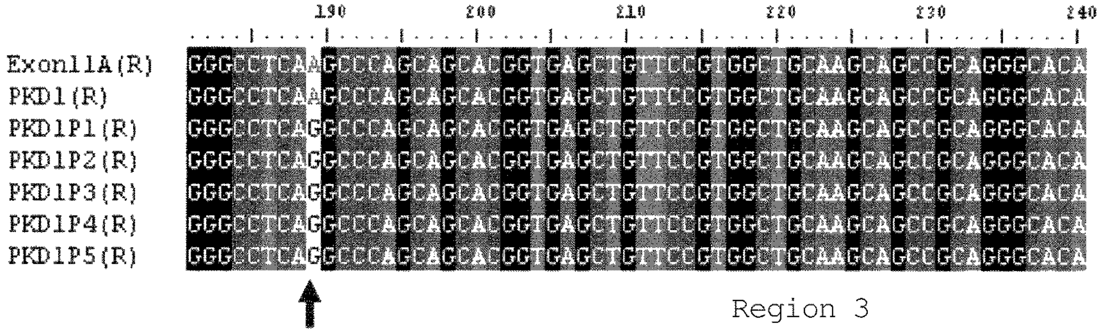
Figures 3, 4:
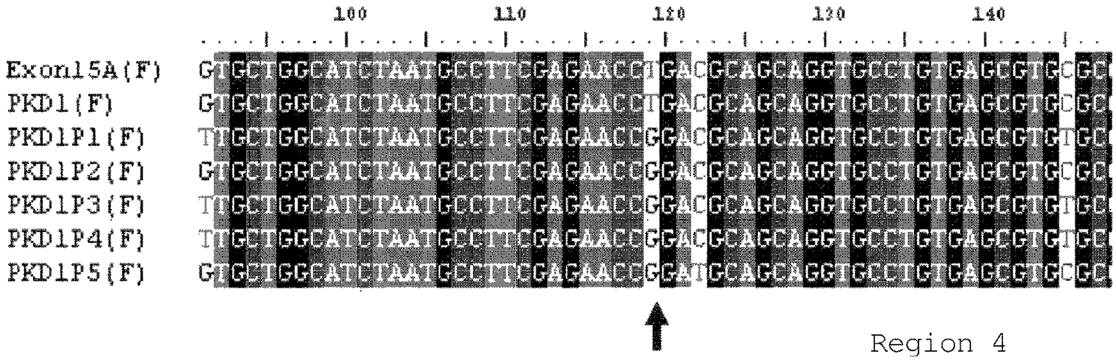
Figures 3, 4, 5:
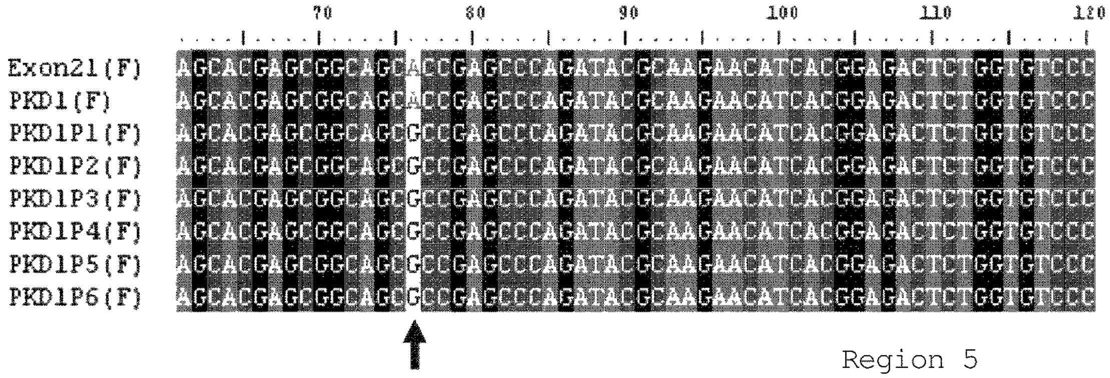
Figures 3, 4, 5, 6:
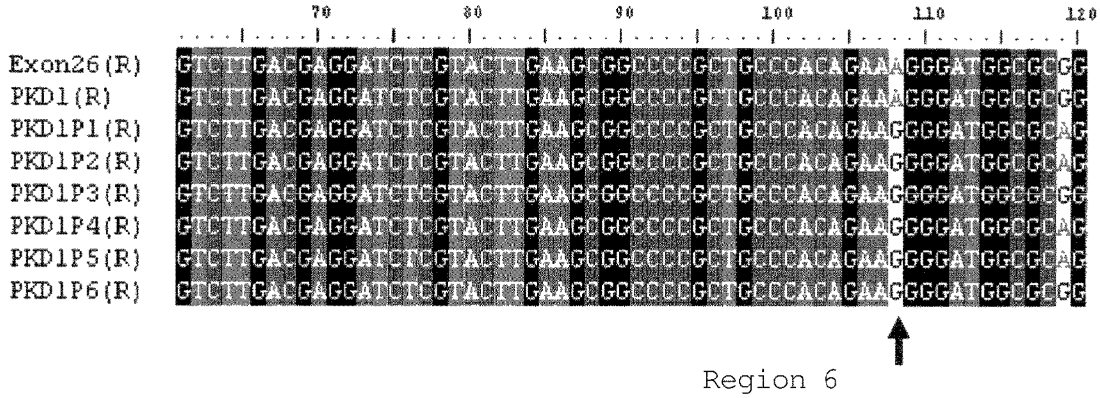

The amplification products obtained by the Multiplex PCR described above in section 3 were purified and sequence analysis was performed by using the Sanger method. The PKD1 gene, which has six kinds of pseudogenes, has several sites where a base specific to PKD1, which is different from any of the bases of pseudogenes, exists. Such sites in seven regions of the amplification products in which pseudogenes might be amplified were intensively investigated. The results show that all the sequences of the amplification products are identical to the sequences of the genuine PKD1 gene (FIG. 3). The above results confirm that when the above primer sets are used, all the exon regions of the PKD1 and PKD2 genes can be efficiently amplified without amplifying pseudogenes.

The invention claimed is:

1. A method for amplifying all the exons of PKD1 and PKD2 genes under a single set of PCR cycling conditions, the method comprising performing PCR using a primer set capable of amplifying all the exons of PKD1 and PDK2 genes under a single set of PCR cycling conditions, wherein said primer set comprises the following primer pairs;

a first primer pair comprising a 1F primer and a 1R primer, wherein the sequence of the 1F primer comprises a sequence at least 90% identical to the sequence of positions 15 to 29 of the nucleotide sequence of SEQ ID NO: 1, and the sequence of the 1R primer comprises a sequence at least 90% identical to the sequence of positions 16 to 30 of the nucleotide sequence of SEQ ID NO: 2;

a second primer pair comprising a 2F primer and a 2R primer, wherein the sequence of the 2F primer comprises a sequence at least 90% identical to the sequence of positions 14 to 28 of the nucleotide sequence of SEQ ID NO: 3, and the sequence of the 2R primer comprises a sequence at least 90% identical to the sequence of positions 13 to 27 of the nucleotide sequence of SEQ ID NO: 4;

a third primer pair comprising a 3F primer and a 3R primer, wherein the sequence of the 3F primer comprises a sequence at least 90% identical to the sequence of positions 14 to 28 of the nucleotide sequence of SEQ ID NO: 5, and the 3R primer comprises a sequence at least 90% identical to the sequence of positions 14 to 28 of the nucleotide sequence of SEQ ID NO: 6;

a fourth primer pair comprising a 4F primer and a 4R primer, wherein the sequence of the 4F primer comprises a sequence at least 90% identical to the sequence of positions 6 to 20 of the nucleotide sequence of SEQ ID NO: 7, and the 4R primer comprises a sequence at least 90% identical to the sequence of positions 8 to 22 of the nucleotide sequence of SEQ ID NO: 8, a fifth primer pair comprising a 5F primer and a 5R primer, wherein the sequence of the 5F primer comprises a sequence at least 90% identical to the sequence of positions 14 to 28 of the nucleotide sequence of SEQ ID NO: 9, and the 5R primer comprises a sequence at least 90% identical to the sequence of positions 10 to 24 of the nucleotide sequence of SEQ ID NO: 10;

a sixth primer pair comprising a 6F primer and a 6R primer, wherein the sequence of the 6F primer comprises a sequence at least 90% identical to the sequence of positions 12 to 26 of the nucleotide sequence of SEQ ID NO: 11, and the 6R primer comprises a sequence at least 90% identical to the sequence of positions 12 to 26 of the nucleotide sequence of SEQ ID NO: 12;

a seventh primer pair comprising a 7F primer and a 7R primer, wherein the sequence of the 7F primer comprises a sequence at least 90% identical to the sequence of positions 21 to 35 of the nucleotide sequence of SEQ ID NO: 13, and the 7R primer comprises a sequence at least 90% identical to the sequence of positions 20 to 34 of the nucleotide sequence of SEQ ID NO: 14;

an eighth primer pair comprising an 8F primer and an 8R primer, wherein the sequence of the 8F primer comprises a sequence at least 90% identical to the sequence of positions 16 to 30 of the nucleotide sequence of SEQ ID NO: 15, and the 8R primer comprises a sequence at least 90%, identical to the sequence of positions 13 to 27 of the nucleotide sequence of SEQ ID NO: 16;

a ninth primer pair comprising a 9F primer and a 9R primer, wherein the sequence of the 9F primer comprises a sequence at least 90% identical to the sequence of positions 21 to 35 of the nucleotide sequence of SEQ ID NO: 17, and the 9R primer comprises a sequence at least 90% identical to the sequence of positions 14 to 28 of the nucleotide sequence of SEQ ID NO: 18;

a tenth primer pair comprising a 10F primer and a 10R primer, wherein the sequence of the 10F primer comprises a sequence at least 90% identical to the sequence of positions 11 to 25 of the nucleotide sequence of SEQ ID NO: 19, and the 10R primer comprises a sequence at least 90% identical to the sequence of positions 11 to 25 of the nucleotide sequence of SEQ ID NO: 20;

an eleventh primer pair comprising an 11F primer and an 11R primer, wherein the sequence of the 11F primer comprises a sequence at least 90% identical to the sequence of positions 11 to 25 of the nucleotide sequence of SEQ ID NO: 21, and the 11R primer comprises a sequence at least 90% identical to the sequence of positions 11 to 25 of the nucleotide sequence of SEQ ID NO: 22;

a twelfth primer pair comprising a 12F primer and a 12R primer, wherein the sequence of the 12F primer comprises a sequence at least 90% identical to the sequence of positions 11 to 25 of the nucleotide sequence of SEQ ID NO: 23, and the 12R primer comprises a sequence at least 90% identical to the sequence of positions 17 to 31 of the nucleotide sequence of SEQ ID NO: 24;

a thirteenth primer pair comprising a 13F primer and a 13R primer, wherein the sequence of the 13F primer comprises a sequence at least 90% identical to the sequence of positions 11 to 25 of the nucleotide sequence of SEQ ID NO: 25, and the 13R primer comprises a sequence at least 90% identical to the sequence of positions 16 to 30 of the nucleotide sequence of SEQ ID NO: 26;

a fourteenth primer pair comprising a 14F primer and a 14R primer, wherein the sequence of the 14F primer comprises a sequence at least 90% identical to the sequence of positions 11 to 25 of the nucleotide sequence of SEQ ID NO: 27, and the 14R primer comprises a sequence at least 90% identical to the sequence of positions 12 to 26 of the nucleotide sequence of SEQ ID NO: 28;

a fifteenth primer pair comprising a 15F primer and a 15R primer, wherein the sequence of the 15F primer comprises a sequence at least 90% identical to the sequence of positions 11 to 25 of the nucleotide sequence of SEQ ID NO: 29, and the 15R primer comprises a sequence at least 90% identical to the sequence of positions 11 to 25 of the nucleotide sequence of SEQ ID NO: 30;

a sixteenth primer pair comprising a 16F primer and a 16R primer, wherein the sequence of the 16F primer comprises a sequence at least 90% identical to the sequence of positions 14 to 28 of the nucleotide sequence of SEQ ID NO: 31, and the 16R primer comprises a sequence at least 90% identical to the sequence of positions 11 to 25 of the nucleotide sequence of SEQ ID NO: 32;

a seventeenth primer pair comprising a 17F primer and a 17R primer, wherein the sequence of the 17F primer comprises a sequence at least 90% identical to the sequence of positions 16 to 30 of the nucleotide sequence of SEQ ID NO: 33, and the 17R primer comprises a sequence at least 90% identical to the sequence of positions 12 to 26 of the nucleotide sequence of SEQ ID NO: 34; and an eighteenth primer pair comprising an 18F primer and an 18R primer, wherein the sequence of the 18F primer comprises a sequence at least 90% identical to the sequence of positions 12 to 26 of the nucleotide sequence of SEQ ID NO: 35, and the 18R primer comprises a sequence at least 90% identical to the sequence of positions 13 to 27 of the nucleotide sequence of SEQ ID NO: 36.

2. The method according to claim 1, wherein the PCR uses multiple reaction vessels.

3. The method according to claim 2, wherein the PCR using multiple reaction vessels are all performed simultaneously.

4. The method according to claim 1, wherein each of the primers has a length of 15 to 40 bases.

5. The method according to claim 1, wherein the sequence of the 1F primer comprises at least positions 15 to 29 of the nucleotide sequence of SEQ ID NO: 1, and the sequence of the 1R primer comprises at least positions 16 to 30 of the nucleotide sequence of SEQ ID NO: 2;

wherein the sequence of the 2F primer comprises at least positions 14 to 28 of the nucleotide sequence of SEQ ID NO: 3, and the sequence of the 2R primer comprises at least positions 13 to 27 of the nucleotide sequence of SEQ ID NO: 4;

wherein the sequence of the 3F primer comprises at least positions 14 to 28 of the nucleotide sequence of SEQ ID NO: 5, and the 3R primer comprises at least positions 14 to 28 of the nucleotide sequence of SEQ ID NO: 6;

wherein the sequence of the 4F primer comprises at least positions 6 to 20 of the nucleotide sequence of SEQ ID NO: 7, and the 4R primer comprises at least positions 8 to 22 of the nucleotide sequence of SEQ ID NO: 8, wherein the sequence of the 5F primer comprises at least positions 14 to 28 of the nucleotide sequence of SEQ ID NO: 9, and the 5R primer comprises at least positions 10 to 24 of the nucleotide sequence of SEQ ID NO: 10;

wherein the sequence of the 6F primer comprises at least positions 12 to 26 of the nucleotide sequence of SEQ ID NO: 11, and the 6R primer comprises at least positions 12 to 26 of the nucleotide sequence of SEQ ID NO: 12;

wherein the sequence of the 7F primer comprises at least positions 21 to 35 of the nucleotide sequence of SEQ ID NO: 13, and the 7R primer comprises at least positions 20 to 34 of the nucleotide sequence of SEQ ID NO: 14;

wherein the sequence of the 8F primer comprises at least positions 16 to 30 of the nucleotide sequence of SEQ ID NO: 15, and the 8R primer comprises at least positions 13 to 27 of the nucleotide sequence of SEQ ID NO: 16;

wherein the sequence of the 9F primer comprises at least positions 21 to 35 of the nucleotide sequence of SEQ ID NO: 17, and the 9R primer comprises at least positions 14 to 28 of the nucleotide sequence of SEQ ID NO: 18;

wherein the sequence of the 10F primer comprises at least positions 11 to 25 of the nucleotide sequence of SEQ ID NO: 19, and the 10R primer comprises at least positions 11 to 25 of the nucleotide sequence of SEQ ID NO: 20;

wherein the sequence of the 11F primer comprises at least positions 11 to 25 of the nucleotide sequence of SEQ ID NO: 21, and the 11R primer comprises at least positions 11 to 25 of the nucleotide sequence of SEQ ID NO: 22;

wherein the sequence of the 12F primer comprises at least positions 11 to 25 of the nucleotide sequence of SEQ ID NO: 23, and the 12R primer comprises at least positions 17 to 31 of the nucleotide sequence of SEQ ID NO: 24;

wherein the sequence of the 13F primer comprises at least positions 11 to 25 of the nucleotide sequence of SEQ ID NO: 25, and the 13R primer comprises at least positions 16 to 30 of the nucleotide sequence of SEQ ID NO: 26;

wherein the sequence of the 14F primer comprises at least positions 11 to 25 of the nucleotide sequence of SEQ ID NO: 27, and the 14R primer comprises at least positions 12 to 26 of the nucleotide sequence of SEQ ID NO: 28;

wherein the sequence of the 15F primer comprises at least positions 11 to 25 of the nucleotide sequence of SEQ ID NO: 29, and the 15R primer comprises at least positions 11 to 25 of the nucleotide sequence of SEQ ID NO: 30;

wherein the sequence of the 16F primer comprises at least positions 14 to 28 of the nucleotide sequence of SEQ ID NO: 31, and the 16R primer comprises at least positions 11 to 25 of the nucleotide sequence of SEQ ID NO: 32;

wherein the sequence of the 17F primer comprises at least positions 16 to 30 of the nucleotide sequence of SEQ ID NO: 33, and the 17R primer comprises at least positions 12 to 26 of the nucleotide sequence of SEQ ID NO: 34; and wherein the sequence of the 18F primer comprises at least positions 12 to 26 of the nucleotide sequence of SEQ ID NO: 35, and the 18R primer comprises at least positions 13 to 27 of the nucleotide sequence of SEQ ID NO: 36.

6. The method according to claim 1, wherein each of the primers is a lyophilized primer.

7. The method according to claim 1, wherein each of the primers is in a solution suitable for use in PCR.

8. The method according to claim 1, wherein in the single set of PCR cycling conditions, primer annealing and primer extension are performed at the same temperature, wherein said same temperature is a single temperature selected from within the range of 62 to 80° C.

9. The method according to claim 1, wherein the sequence of the 1F primer comprises a sequence at least 95% identical to the sequence of positions 15 to 29 of the nucleotide sequence of SEQ ID NO: 1, and the sequence of the 1R primer comprises a sequence at least 95% identical to the sequence of positions 16 to 30 of the nucleotide sequence of SEQ ID NO: 2;

wherein the sequence of the 2F primer comprises a sequence at least 95% identical to the sequence of positions 14 to 28 of the nucleotide sequence of SEQ ID NO: 3, and the sequence of the 2R primer comprises a sequence at least 95% identical to the sequence of positions 13 to 27 of the nucleotide sequence of SEQ ID NO: 4;

wherein the sequence of the 3F primer comprises a sequence at least 95% identical to the sequence of positions 14 to 28 of the nucleotide sequence of SEQ ID NO: 5, and the 3R primer comprises a sequence at least 95% identical to the sequence of positions 14 to 28 of the nucleotide sequence of SEQ ID NO: 6;

wherein the sequence of the 4F primer comprises a sequence at least 95% identical to the sequence of positions 6 to 20 of the nucleotide sequence of SEQ ID NO: 7, and the 4R primer comprises a sequence at least 95% identical to the sequence of positions 8 to 22 of the nucleotide sequence of SEQ ID NO: 8, wherein the sequence of the 5F primer comprises a sequence at least 95% identical to the sequence of positions 14 to 28 of the nucleotide sequence of SEQ ID NO: 9, and the 5R primer comprises a sequence at least 95% identical to the sequence of positions 10 to 24 of the nucleotide sequence of SEQ ID NO: 10;

wherein the sequence of the 6F primer comprises a sequence at least 95% identical to the sequence of positions 12 to 26 of the nucleotide sequence of SEQ ID NO: 11, and the 6R primer comprises a sequence at least 95% identical to the sequence of positions 12 to 26 of the nucleotide sequence of SEQ ID NO: 12;

wherein the sequence of the 7F primer comprises a sequence at least 95% identical to the sequence of positions 21 to 35 of the nucleotide sequence of SEQ ID NO: 13, and the 7R primer comprises a sequence at least 95% identical to the sequence of positions 20 to 34 of the nucleotide sequence of SEQ ID NO: 14;

wherein the sequence of the 8F primer comprises a sequence at least 95% identical to the sequence of positions 16 to 30 of the nucleotide sequence of SEQ ID NO: 15, and the 8R primer comprises a sequence at least 95% identical to the sequence of positions 13 to 27 of the nucleotide sequence of SEQ ID NO: 16;

wherein the sequence of the 9F primer comprises a sequence at least 95% identical to the sequence of positions 21 to 35 of the nucleotide sequence of SEQ ID NO: 17, and the 9R primer comprises a sequence at least 95% identical to the sequence of positions 14 to 28 of the nucleotide sequence of SEQ ID NO: 18;

wherein the sequence of the 10F primer comprises a sequence at least 95% identical to the sequence of positions 11 to 25 of the nucleotide sequence of SEQ ID NO: 19, and the 10R primer comprises a sequence at least 95% identical to the sequence of positions 11 to 25 of the nucleotide sequence of SEQ ID NO: 20;

wherein the sequence of the 11F primer comprises a sequence at least 95% identical to the sequence of positions 11 to 25 of the nucleotide sequence of SEQ ID NO: 21, and the 11R primer comprises a sequence at least 95% identical to the sequence of positions 11 to 25 of the nucleotide sequence of SEQ ID NO: 22;

wherein the sequence of the 12F primer comprises a sequence at least 95% identical to the sequence of positions 11 to 25 of the nucleotide sequence of SEQ ID NO: 23, and the 12R primer comprises a sequence at least 95% identical to the sequence of positions 17 to 31 of the nucleotide sequence of SEQ ID NO: 24;

wherein the sequence of the 13F primer comprises a sequence at least 95% identical to the sequence of positions 11 to 25 of the nucleotide sequence of SEQ ID NO: 25, and the 13R primer comprises a sequence at least 95% identical to the sequence of positions 16 to 30 of the nucleotide sequence of SEQ ID NO: 26;

wherein the sequence of the 14F primer comprises a sequence at least 95% identical to the sequence of positions 11 to 25 of the nucleotide sequence of SEQ ID NO: 27, and the 14R primer comprises a sequence at least 95% identical to the sequence of positions 12 to 26 of the nucleotide sequence of SEQ ID NO: 28;

wherein the sequence of the 15F primer comprises a sequence at least 95% identical to the sequence of positions 11 to 25 of the nucleotide sequence of SEQ ID NO: 29, and the 15R primer comprises a sequence at least 95% identical to the sequence of positions 11 to 25 of the nucleotide sequence of SEQ ID NO: 30;

wherein the sequence of the 16F primer comprises a sequence at least 95% identical to the sequence of positions 14 to 28 of the nucleotide sequence of SEQ ID NO: 31, and the 16R primer comprises a sequence at least 95% identical to the sequence of positions 11 to 25 of the nucleotide sequence of SEQ ID NO: 32;

wherein the sequence of the 17F primer comprises a sequence at least 95% identical to the sequence of positions 16 to 30 of the nucleotide sequence of SEQ ID NO: 33, and the 17R primer comprises a sequence at least 95% identical to the sequence of positions 12 to 26 of the nucleotide sequence of SEQ ID NO: 34; and wherein the sequence of the 18F primer comprises a sequence at least 95% identical to the sequence of positions 12 to 26 of the nucleotide sequence of SEQ ID NO: 35, and the 18R primer comprises a sequence at least 95% identical to the sequence of positions 13 to 27 of the nucleotide sequence of SEQ ID NO: 36.

* * * * *

SEQUENCE LISTING

```
<160> NUMBER OF SEQ ID NOS: 56

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 1

gcagcagttt cttgtggctg tttcttccc                                    29


<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 2

gttctcagga tagccttgga acccaatagc                                   30


<210> SEQ ID NO 3
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 3

gtttctctgg gtttatgcct cgaggtgg                                     28


<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 4

ctgcctttca ggaataactc acacacg                                      27
```

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 5
acattacctc caggcctttt ctctgagc                                    28

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 6
gttacctccc aacagacagg gaaaccga                                    28

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
ccgagggacc cccacatcac                                             20

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 8
ccctcagacg acccctctgg ga                                          22

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 9
ctgccacagt tccacgtaca gtcttcaa                                    28

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 10
ccctgcgttc acacaggaca gaac                                        24

<210> SEQ ID NO 11
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 11
atgtgaagag gtgccttgtg tggtcg 26

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 12
gcaatgaaga ggaaagcagc acagag 26

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 13
gccgggactg cctgtgtggc tccttgagtg cgcac 35

<210> SEQ ID NO 14
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 14
ctggggccct ggggatccca tgaggctctt tcca 34

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 15
atatcagcat ggtggccyga tgcagtggca 30

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 16
taggccagcg ggggccggag gagtgag 27

<210> SEQ ID NO 17
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 17
acgccaagga caagggagta gttctccagg agtgc 35

<210> SEQ ID NO 18
<211> LENGTH: 28

-continued

<212> TYPE: DNA
<213> ORGANISM: Artificial Sequence
<220> FEATURE:
<223> OTHER INFORMATION: Synthetic oligonucleotide primer

<400> SEQUENCE: 18
cgcctactcc aaccccagcc tacctctg 28

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 19
aagtggctgg tggataactg ggacc 25

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 20
tgacaatctg ccacactcct cccac 25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 21
tcatcttcac tcagccagcc caacg 25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 22
gcctctcccg tcctgtgtta aacgc 25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 23
tgtgaatgtg tgccggttcc cttgg 25

<210> SEQ ID NO 24
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 24
gggaatgaat gaatgaatgg tgggagttca g 31

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 25
ggttcccgag tctgccctca aaagc 25

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 26
cctccacatc tcatacggca tactaaagcc 30

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 27
tggctggcaa ttggagaatg cagag 25

<210> SEQ ID NO 28
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 28
ccaggcccag ctaacacact gaaagg 26

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 29
caatctgggc agccatcctc agtgc 25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 30
tgagcctttc cagttgccac gactc 25

<210> SEQ ID NO 31
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 31
aggcctgctg tattcctatt tgcaacag 28

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 32
acaaagaggc ccaactttcc tgtcc 25

<210> SEQ ID NO 33
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 33
accctgactt tttccatgta actgttccac 30

<210> SEQ ID NO 34
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 34
actgcctggt ctcatgtgga ctcttg 26

<210> SEQ ID NO 35
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 35
aagacttctg atacgcgctg acttgc 26

<210> SEQ ID NO 36
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 36
atgccccatt ttccttcaca ctcttgg 27

<210> SEQ ID NO 37
<211> LENGTH: 48944
<212> TYPE: DNA
<213> ORGANISM: Homo sapiens

<400> SEQUENCE: 37
cgcctactcc aaccccagcc tacctctggt gcaccctccg tcccatagca aagcccctgc 60
acagactcca gccgagccca cacctggcta tgaggtgggc cagcggaagc gcctcatctc 120

-continued

```
ctcggtggag gacttcaccg agtttgtgtg aggccggggc cctccctcct gcactggcct    180
tggacggtat tgcctgtcag tgaaataaat aaagtcctga ccccagtgca cagacataga    240
ggcacagatt gcagtcagac agctctttta ttgactttgt ctgcttggtg cgggggttgg    300
gggggtgtcg aggctctaga agcggccatg cccacagaag tggtacacag aagcaggcac    360
agccagctcc gagggccttg aggctgcctg ggccatacag cacactcgcg cgtgcgcgcg    420
cgcacacaca cacacacaca gtcaccttcc tccaccctgg gagccagccc ccaggaggag    480
tcttttcctc taaccaccct ggggtcctct gacatgccta gtcctgctac ttgcccagac    540
ctgatgccag caggcctggg cgctgctctc ttgctacctg gcctggggca agggaggatg    600
acaaggcctc tggggtgatg agagtgcctg gcagacagct gtgcccccag caccggccca    660
aggccaagct cgcatccaag cagcagccgg gctgccataa cgccaccaca cctaccaagc    720
gcagcaggtg ttgggggagg ccagctctgg gcgcaggccc ctcagcccta gtgaaaatag    780
tgacatacaa aaatatacac attttaacac catataaatt actgacacga gacacacagt    840
gagacggtgc agggagtacg gtaggaactg gagaggtaat aacttagggg cagggtggcg    900
gcggtgcagg ctaaccctcc ctgaagccag cagccttagc agtgggggac atctgcccag    960
ggggtggggc cgggcacagc ccgctgtacc tgaggactcg gggaaataaa ttagcatctc   1020
agaggctaga aaccgtccaa tactgctgtg tccttcccaa gggagctggg gaggggaccc   1080
tgggtcctgg ttggccacac agcctcttta aagtgctgaa gcccacagac agacagatgc   1140
ccctgcctgc tctctgggga acctacgtgc agccattctg cctggccctc ggccttgaca   1200
gcggcagaaa gtaatactga gcggtgtcca ctccgactcc acggcccacc cccgccagga   1260
aggaggacta agtgctgctg gggtggacct tgttcttggc ccgaaggggt gtcctgctgg   1320
ggccagtggc caggtccaca ccccgactgg cccgggcaag gcggctgggc agtgctggcc   1380
gcaggcccgg ggatgggcca cgggaagatc cggcgggcgc ccggctgctc ctgcggcctt   1440
gcaggctgtg cagctgctgc tccagctggt agacgtcctc tgtggcctgg ttgagtcggt   1500
caaactgggt gagcagggcc tcgaacacgg cttggaggcg ggagggctca ggctcacacc   1560
ttgtccccag ccggcccagg ctcacgctca gcccatccag ctggctggag gaggtggagg   1620
ggtgcgaggc atcggagcca gcgctgggtg ggggcacatc cggggatacc ttggagcccc   1680
tggaggagcg agagggcagc ggctccatcc cttcaaagcg gactttgtgg cggaactggg   1740
ggcggcacag gggctcagtc agtccggctg caccctgggc agagcccagg gcgtgtccct   1800
ctcccccccca ctgggccgta cccacctcct tgaccttgct gaggcccatc cagaggcgca   1860
gcctgcgcag gaacaactcc accatctcgt agtcctgggg ctcccaggcc ggccggtaca   1920
gctctccacg caaggcgtgg tagcgccagc ggagaataac agcccccagc cgtagggcgc   1980
cccacagccg cagtgcccag agccccacac acagcagggg tgacaggtgc caggactcgg   2040
caggacacag ggtagagagc ccagtcccag ggcacagcac caacagggcc tgggccacgc   2100
tccagaggga gtccacacag gaagacacga gctgcgggga aggcgacacc agtgagggcg   2160
tacagctgag ctgagctgag ctaagacgcc ctccccggcc gcgcagtcac ctaccaggat   2220
ggccagctgg gcgtaggcta ccccgagcac caccaggccc aaggtgaccc ccaggagctc   2280
tggcagagct cggcataatg tcttgccaaa gacggaccac tggcgcacga agcgtagctg   2340
ctgggcagcc tgcggacgag aaatctgtct gcttgcagcc ctggggtgtg cgcccagccc   2400
cgcgcccacc ggcccagccc tcaccttgac caaaagcagg aagagcagcg aggccgccag   2460
gccacgggct gcggagctca gctgcgccac ctggtcgaag ctagtgaagc ggcgcgggcg   2520
```

-continued

```
gccgcgcacg aaacgggtcc actggcggtc agcggcaccc agctgggcga ggcgtaccag   2580
tgccgtggcc gccgtcagcg ccaccagcag ccaccgcgcc caggctccga gccgcagcac   2640
gcgccagcgc ccttccctgt gccaagtacg ggcctcggcc acggcgaagt gcacggcgaa   2700
cagcagcagg cacacctgtg gggggcgcgg tcaggagggc gggagggacg ctgccggggc   2760
ggggccctgc gagggggcgg gacgctgccg gggcggggcc ctacgagggg gcgggacgct   2820
gccggggcgg ggccctgcga gggggcggga cgctgcgagg gggcggggcg ctgcgagggg   2880
tgagacgctg ccggggcggg gccccgcgag ggggcgggac gctgccggtg ggaggcgcgg   2940
ggtctggccg gggacgggcg taccgaggtg agcagaggca gcgagaggcc cgcgctgagg   3000
cggcgcagcg caaaggggcg gacgctgagg gcggccaggg cgcggccggc cgccgggaac   3060
tcgaggcgca gcgtgacggc ggcgtgcagc ccacggccg ggctgtagcg cgtgagctcc   3120
aggaacacag cgcggctcct gcgcagaggg tgcgggtcag taggagcggg tggcagggcg   3180
ggagctgcgg ggaccgcgca gtgcaggcgt ggctgagggg ctgtggaagc cgcctaggcc   3240
agcgggggcc ggaggagtga gggtgggctc ctggctggtg actgcggcca ccccggagag   3300
ggcaggggag ggagctccca cctgttgtcc agccagttgt gcagctgcag gaagcgcagc   3360
cggtcgcggc tctcctccag gctcaggccc agctcctgca cgtagccccc gctgtcatac   3420
acggcacagg agccccagga ccatgccctg ccggagaggg gtggcgtggg tgccgcaccc   3480
cagcccttcc ggcaccccgg agccaggctg gtcaggaggc cgcggcactc ctggagaact   3540
actcccttgt ccttggcgta gacgcccggg gccctcgctc tgctcacccc agcagatccg   3600
gcgctgaata ggcccacgtc cccgagccat tgtgaggact ctcccagcca acgtcgtaat   3660
cgctggtgct gaagcctcct gcggccgagc acgtgtggac cctggggccg ggagggtctg   3720
ggtagagtgc tgaaacacac agagccccag gccggggcca gggcctcatc aaaacccaac   3780
aggagtgttt cctgctggcc agctcgcctg agctctggtt cggcgccacc ccagggaacc   3840
ctcccagcag ccatcaatta gacaacgtta ccatctctca tatacagaga aggaaacggc   3900
ggtgttaaga gggcaaaggt cacacagcta gggagcaggg ctgatgccag agctccgcta   3960
aaggctgctc tctcaacaag aggaacgatt taagtcttgg ggcacgccct gccagctcac   4020
cttcctgcag ccgcacctgc cgcagccgtg ggggccccag ctctgggctg gactggttcc   4080
cgtggacgta gggcagcagc acgtgggcca tccatggcca gagctcctca gacctgccac   4140
agcatcagtc acacgctcca gcccctactg ccccatgccc gcctcgagtg agcggccacc   4200
agagacccag ggaacatggc tcccactgcc ctgctggcca cggctagacc tgggcttctc   4260
agccttatcc tggggatgtt ctggggcaga cagttgtctg tcatgggccc gtcctgtgca   4320
ctgcaagaca cggacctgtg tccctcccct ctgcctactg atgccagcag cacctacctc   4380
cagttctagc agccacaaag gtatctacac atgtccacat gtcccctagg gtctggctgg   4440
actaaaggca aaactaaagc ccagaagaca gaccagtgca ccggatgccc gtaccgcgtg   4500
atggccagga aggcccggct gtgcagctcc tgcttgatgg cgctttgcag acggtaggcg   4560
tgcccatggc atgaggcatc cccatagctg gccagcaggg tcaccagcag aaaaagcatg   4620
tacaccagga ggctctggtg gacggggggg ccctgtggtc agcctggccc cagcccacag   4680
tgacagcagg gctttggcaa cggctggagc catggctgcg gcaggtgtgg ctgcaggaag   4740
gtgagctggc agggggcgcc ccaagactct acctggccag ggtaatggca gcacacaccc   4800
tgcccggaac cccacctggg ggcagacaca caggccactg cagtggtgct taggggcctt   4860
```

-continued

```
cagggccagg caggagtggg cattggagct gggccctggc agggactggg gcagcaagtg   4920
gggggcgtgg ggtaggaggg agaccgggca aaggctgcag agcattgaac ccctaagggc   4980
cttctgaggt gaggaaaggg ggacaggagt gtcctgcgtg catgggtggg aggtgggaga   5040
caagagacgg aggtggcagg ggcacaggcc gcacccaggc tcacccgcag catgccatgt   5100
agcctcttga ccttgcgggc ttcttccttg gccaggaaga gtgcaaagcc gtggggtggc   5160
cgtacgcggg gcacacgtgc gctcacaggc gtcacagccg ggctctctac cagggtgtca   5220
tcttcatccg ggtgcagccg cttggccacc agtgagaagt acagggcttc cagcaagacc   5280
tggggagggg gtggcttcag aggggtcccc cgtgatggag gcctgtagcc taccccctggc  5340
agccccctca ccttcagtgg ctcccagccg aggaatgagg ccaggaagct ggcgctgctg   5400
gacaggagcc acgcaacact cacgcccggg gggaagctcg cacccaccca ccctgagaca   5460
gccacagcca cagccaccag gagcaggctg agcccgtggg ccagggaggc acaccaggcc   5520
ggcagcaggc gcttccgcag accctccacc agtcctgggg aagcagagac agacctgtga   5580
gaggcagctc acagggaggg gctaggggca tcccggggct acgcaagcac acctgtcctg   5640
gacagcctcg ctgcctgggg ctgttcccag ttcaggcctg ggctgggtgg ccccagctcc   5700
cccagcctct gcagcgccag cgtctctgtc ttctccccag gagtgctgga cctgagggac   5760
atggtaggct gtgaattcat cccggcctcc aggaggcagt tgcagccaag cccatgttaa   5820
cctgggcggg cagtttcttg agcctcttgg gtcacagggt ccccccgaca aaaagccgga   5880
agaccctacc ccaaacgaga gtgggagtgg tgctgggagc cagggaacca agagccactc   5940
caggcaccga agtcaggcgt ccgcctgcgt ccctctcccg cccgcttgct gctgataaac   6000
ccatcgccca cagcctgacc agctgccctt acagcagtgc acagtctctc agggtgcaat   6060
gagccccccct tcaaccctgc aaactatgat tgggtctcaa ccatccaaca agcatctcta  6120
caatctagag acgccagtgt gtctgtccca tgcaggttta tggcctaaaa ttaacttctg   6180
gacaaggaaa catatgaatg cctttcaaat cccaacagtg tgtagggctc cctgaggcca   6240
gagatctgct tgtgtctcca ggagccagtg accaccgagg ctgtgccact gcatcgggcc   6300
accatgctga tatgcccggt cccagagctg ctagagaaga ggtacagagg cagcgaagac   6360
acgttgaggg ggaggacgag accaactgcg agacgccgag tcccgggctc tcaggacgct   6420
ctcccgtacc tgcgccctcg tcagcccatc accgaaagaa cggcctgacc cagggtcaca   6480
ctgcactgaa tgcttcctgt tttgctgtct ctcggaggat aaaagacact cttggctggg   6540
cgcagtgtct caagcctgta atcccagcac ttcaggaggc tgaggcagga ggatcacttg   6600
agctcaggag ttggagacag tgagaccctg tctttacaaa aaattaaaaa atgacctagc   6660
ctcaacttgg tcaggcgtgg tggctcacgc ctgtaatctc agcattttgg gaggctgaga   6720
tgggtggatc acgaggtcag gagttcaaga ccagcctggc taagatggtg aaacctcctc   6780
tctactaaaa cacacacaca aaaaattagc cggctgtggc ggcgggcgcc tgtaatctta   6840
gctacttggg aggctgaggc agataactgc ttgaacgtgg gaggcagact ttgcagtgag   6900
ccgagatcat gcgactgcac tccagtctgg gcaacagaga ctccatctca aaaaaataaa   6960
taaaaataaa aaataaccca gcctcaacta ttcctttata gcaacacaaa tgactcaggg   7020
tctgactcag ggagcaggct ctcgctggca gagacggaga atggccaata gggaggcatg   7080
gagtggcagg gaatgccagg gcagaggcgc cgccaggacg gagggtgcag gctcaggcgc   7140
agggaaggcc gtgctctgcg ttgggaaagg agccacggga cgcgctggag gctgcagtga   7200
ggaaggacgc agaggggtcc aggacaaacc caagcctccg acctggtcag cccgaagcac   7260
```

tgtccgagca agggacggcc aagggttgag gaagccggga gggtgagggc cacgcgctct 7320
gtgtggatgc ggagtctgag ctgccgtcag aaatccccgc ggaagcactg aatctggatt 7380
tcacagagct ttgggccgga gatacctggg gctggtcagc atgtagtgac taccccctgga 7440
tttccccata ctctgtattt ttaaaaccaa ccagcaattt attcataaag atgccctcat 7500
gtgatggtta tctgcctttt gtaaatcagg aagttttcct ttttgtttga gtccaggggc 7560
agttcatacc tctttagttc ttggttgctt aacaatgaga agcactcaaa ggaataacac 7620
acaaatcaaa ctagatgtgg atgcaaaagc agcagtcacg caccacttag tgccagggat 7680
gtgttctgag aaatgcgtca ttaggtaatt ctgttgctgt gcaaatgtca cagggcgtag 7740
ttacccaaac ccagacaccg cagcccctgt gcatgcaggc cctgtggtgt ggcctgtggc 7800
tccggggcac cgcacctgca ctgcatgcca ctgcactgaa tcctgcaggc agctgcagtg 7860
caacggcagg gccgtgtgga cctcagcaca cctgagcata ggagggcatg gcagagcccg 7920
gggtcacacg cgtgggaaca cgccgtgggt gcgctccgcc gccggctgcc atgtgcgtga 7980
ctatgtgcgt gactacatac aaggtaacct ctatatgacc atttgttgat aagttacaaa 8040
acaaccaaga aattgaggaa tttttttgtt tttgagacgg agtttcgctc ttgttgccca 8100
ggctggagtg cagtggcgcg atctcggctc actacaacct tcacctacca ggttcaatcg 8160
attctcctac ctcagtctcc cgagtaactg ggactacagg cgcctgccag catgcccggc 8220
taattttttg tatttttagt agagacgggg tttcgccatg ttggccaggc tggtctcgaa 8280
ctgctgacct caggtcatct gcccacctcg gcctcccaaa gtgctgggat tacacgtgtg 8340
agccaccgcg cccggccaaa aatggggtat ttaaaaaccc gcccataatt tctcactgct 8400
ctgagaccaa gataaaaacg tggccccggc cagcctcaca caggagcctt tctgctccta 8460
caaagcccca tgagcctgct ccctccctag agggaaggtt ctggggccct ggggatccca 8520
tgaggctctt tccacagaca acagaggttc agagaagtga agtggtgcag ccacagccct 8580
gccctggcac cccaccccac cctaccccag gcgggaacca cggctgcctg gcctgagtcc 8640
cggcccctcc tctggcaatc ccccctcccc cgagagccgg acactcacag gctgctgagc 8700
aggtccgttt ccatgtgggt gtcttgggta ggggctgggc tgctgacccc ctcggcaagg 8760
acctgctgga tcaggtcttc atctagaggt acaggaggca tagggtgggc ccagctgcaa 8820
gggtgagctt cagagccccc tcctctcacc ccagctcacc tgatgctgag aaggatttgg 8880
caggcgagta ggggctggcc agggagaagc cgtcctcctc tgggcccagc ccatggcccg 8940
cctggccccg tgccagctgc cgcagattgc tacccacaat ggacgggtca ctgagcaggt 9000
ccggccaact gagcgttccc tcgccggagg gccagcacac cagactgcag gtggcgcggg 9060
tcagcaaggt accaggggat gtgtcacaca cacagcccac ccccgtccag tcacgcacgg 9120
acaccctggg cttccgagca aacctgctcc cgggtggtgt gaccacatgg agccacagac 9180
acccagcaag gacacgcagc ccgcacaccc ccggcacccc agacacagtg acctgcacca 9240
gggctcgagg tttctctagg gaacccacct cttagaatca tccagaaaca agtcactctt 9300
catctgtcca acaaaggcct gctgagaggt gcacagtgtc ttgagtccaa gctgcgccaa 9360
ggcggcagga cccccagccc agcccaggac ccccagtaga gtcctcacct cagcgtggag 9420
gcctgagaac gtgaggaagg agctgtccag cacggacgag tccaggcagc tgtcgatgtc 9480
cagcacctgc tgcccggcag gtgtggggct cgggctccca gccacctgca ggacgagggc 9540
agtggtcagc gggcggcagc tcagacctgc tcaggacagg gatgagaagc cacctcctca 9600

-continued

```
gcagacagga cagagcccgg tgccatctga cagaatgtcc tagaatgctg gatatatggg   9660
acatctgcac cgtccgtgat ggcagcccct cgcgacgtgt gccactgaac acttgacagc   9720
agactggtgc agctaaggaa cagagtttta aatttcatat tttctttttt agatggagtc   9780
tcgctgtcac ccaggctgga gtgcaatggc gcaatctcag ctcactgcaa cctccacctc   9840
ccgcgttcag gcgattgtcc tggctcagcc tcctgagtag ctgggattac aggtgcctgc   9900
caccatgccc agctaatttt ttgtattttt agtagagacg gggtttcact gtgttggcca   9960
ggctggtctt ggaactcctg acctcaagtg atctgcccgc ctccgcctcc caaagtgctg  10020
ggattacagg tgtgagccac cacacccggc catcgttcca ttttaattaa cttaaatacg  10080
agcagccaca tgtggcctct ggttcctgcc acggactcgg gagcaacccc tcctggtcgc  10140
ggcttatgcg ccttctctgt gtgctgctgg ggttagtttg catgtaacct cttgaggacc  10200
ccacgtgtgc attcctaagg ggtgcggcct cccgtttccg tatgaatggg aagcgttccc  10260
acctgctgta ttcttggaaa gagtctgtga aggattggtg ttaattcttc cttaactgct  10320
tagaaaaatt ctatcgtgaa ggctctgagc ctgagctttt ctttgtggga tttttttttt  10380
tttttttgg agatggagtc ttgctccgtt gcccaggatg gagtgcagtg gcgcaatctc  10440
ggctcactgc aagctccgcc tcctgggttc atgccattct cctgcctcag cctctcgagt  10500
agctgggact acaggcgccc gccaccatgc ccagctaagt ttttgtattt gtagtagagt  10560
cggggtttca ttgtgttggc caggctggtc tcgaactcct gacctcaagt gatctgcccg  10620
cctcggcctc ccaaagtgct gggattacag gcgtgagcca ccgcgcctgg cccttttttaa  10680
tgttttatat agatggggtc ttgctatgtt gcccaggctg gtctcaaact cctggactca  10740
gatccgccca cctcggccac ctgaagtgtt gggattacag gcgtgagcca ccacacccgg  10800
cccggccact gggacgtttc taagggacta actcagcctc ttcacttcct atagatgtac  10860
tgagattttc ttctggagtg catttcggaa gcgtgcacag ccgcgtgctt gcttcttctg  10920
agttatctgg cgtgctgctg tgcagtcgtc cgtggcgtct gcttagcaaa gtgccctcgt  10980
tctttcacca ttctggcttc tgagtcttct ctctttctcc ctggtcagtc tagctaaggc  11040
tgctcaagtg tgttgaccct tcccgagcag cctttggtgg acgcctttcc ctctggctgc  11100
agcactggaa agtggcggcc ctaggcatgg tgccgaggcc caggctccat tcccagtact  11160
cccgggtccc cagccccagc ccaccttgct ccgggacatc cggaagagaa aaaggatggc  11220
caggtagacg ggatagacaa ccacgctgga caccaggcca acagcgactg tgtcgacgct  11280
cagcgggctc agcctggaca catgccccgt gctgtgtgga ggagaggagg ccacacaggt  11340
gaggctgagg ggcaggaagg gctgggcagg aagaggctgc cccgacccct acggcaccca  11400
cctgtaggca gagtcgccaa cagccccgta ccacacggcg ttggcgccca ggaagaggca  11460
gatgaggaga acgcagcagg tggccctctg gatgcgagtg aaacggctac gaggcggccg  11520
gtcccatatg gagagccaga tgtgcttgtc aaagaagcca cgctgcagct cagccaccag  11580
caggcgccgg aagcgcaaaa gggctgcgtc gcctagaagg cagggagggc cgcactgcag  11640
gaggccacgg ggcaggacca ccctgcccaa cctcccacgg agtgggaaca tggaacgagg  11700
ccttactcgc ggccagcacc tccttctcca ccaggccccc gttggcctcc gtctccaccg  11760
aaagccagtc attgaccagg aagaaggcgc tgcgtgccgt ctgcaggtcc ctgacgatga  11820
cgtgctgcag gaaccaggca gggctgagcc ctgcagaggc gcaggaggga ggtcaggctc  11880
gcagggcgcc ccaatgcggg ggcagagggg cagagcttgg cagggtccgc acaaaccttt  11940
gttgtcgtgc cacactcgga tcttccacac gctacccagg ctgtgcgggg tggcgatccg  12000
```

gaagatgtcc aggctgttgc ggtggaaggc tctgtcgccg tccaggtgcc ggtggccgct 12060
ccggctgtcc accccataca gcatgatgcc cacgtgggcc gtggtacctg ggaggcaaga 12120
gggaggggtg ggaggctcgg tctgctgccc aacacgtgtg gcatcccagg caagtcatct 12180
cagctttggc ctgtgcgcac tcaaggagcc acacaggcag tcccggcttt gcacggctct 12240
gccatacaca aggagctgcg gttactgcaa tttgtccaat taacagcagg acctcaagga 12300
catgattaag ttacatggaa agaactgtaa cttgtgacat gcaaacatgg ctgcacacgc 12360
ctcagtccac accacaacca gtgacccgca ctgcacacct gtccacgcct cagtcatgcc 12420
acaaccggtg acccgcacca cacacccgtc cctcagttca tgcacagact gcaaagcgtg 12480
aagctgtgtc acctcctctc ccagtgacag acccaggtga cagtattttt tttctttttt 12540
ttttgagatg gagtcttgct gtgtcaccca ggctggagtg cagtggcgca atctcagctc 12600
actgcaagct ccgcctcccg ggttcacgcc attctcctgc ctcagtctcc caaggagctg 12660
ggactacagg cgcctgccac tacgccgggc taattttttt gtacttttta ttagagacag 12720
ggtttcaccg ttagccagga tggtctcgat ctcctgaccc cgtgatttgc ctgcctggcc 12780
tcccaaagtg ctcggattac aggtgtgagc caccgcgccc ggccgacagt ttttaaaagt 12840
aggtaatcaa aagaaagaac tgggcaatga agaggaaagc agcacagaga taaaaaatgg 12900
gaacacagcc aggtgtggtg gctcacacct gtcatcccag cactctggca ggccgaggca 12960
ggcggatcac ctgaggtcag gagttcgcct ggctgacatg gtgaaaaatt aactgggtgt 13020
ggtggtgtgc acctgtactc ccagctactc aggagaatcg cttaagggga atggcttaaa 13080
cccgggagct ggaagttgct gtgagccaag atcatgccat tgcactccag cctgggcaac 13140
agagtgagac tccgtctcta aaaaaagaaa aacgaaaaca aaaagggaat gccagaaggg 13200
caattccaat gaaaggaaaa tggaggtact gaagaaacag ccacggggag ggtgctggcg 13260
cctccgtctg agagacgagc tatgcagtca ggatcgcggg tggatgcaca gtctcccaca 13320
gtggtagcga tgctcacgtc acttgtgggg ccacgctact gtgcagaacg tgggctgccc 13380
accctgactg actggcacct acttccagct aggagctgtc ctagtcctca gggacagtga 13440
gtgctcacga ggtcattccc aggatgaaca cacgagccct tcacacagca ctgcaaaaac 13500
tgccttgttc tgacgcctgc gacgagactc actcccagag ggtgcaacca gcacagccag 13560
tgagagcagg ggaggccctg ccaccccgct gcgcccctca cctgagcccc ggccccagcc 13620
tgtcttgacg aggatctcgt acttgaagcg gccccgctgc ccacagaaag ggatggcgcg 13680
gccccggctg gcatccaact ggtccagctt gtgcaggatg gcggccatga ccatgtaggt 13740
caccaggcac acagcacatg tcagcatgac gatgtagttt acatccgctg tcggctcctg 13800
tgaggacaca gccgccgggc ccaggaggtc acgtgcaagc tgtgccttct caggatagag 13860
ccgagcccac ccaggccctc ctcgactctg cagaggctcc caggagcaca gggtcactca 13920
caggaaacac aaagcggaca tggcttgggg gcacgaagag gctggcgccg aaggcggtga 13980
ggtggcgggt gaggcagacg gcctggcggg gcgaggtctc ctccaggggc agcagcccct 14040
ctgtccgcca caccatgtcc tcctcgctga agtactggca cagggacgtg tacaggccca 14100
cggacacctg cagcgccgac cagcggaagt ggctggagag gttcagatgg taactccccg 14160
ctgggtctct gctcctgggc agggaagggg tagcggacgt gagcccaggc tccgccaggt 14220
tggatgtcgc agtctcagag cccatacccg gtccagtccc ctcgctgcct gccgtcccca 14280
tggggccagt aacccaggca atgctgaccc atgatgccct gccctgccct gccaggctgg 14340

```
cccgcagagc tcaccccggg gaaatgaaga aggtgtaggg ccggtggtca gcaccctgga  14400
gtgactctgg gcggatcctc ctgctagccg agcagttgtg ctcattgggc cggggctccg  14460
agtgtaggta gactgccagg tagggctcag gttcctcaga caggtagtgg cctggggcag  14520
aacgcgcagg tcacacgcct gccgggaagc tcaaccaccc gggggacacc cacgatggcc  14580
ctcctgagcc caccctctgc cacgggcctg aaaggccata ggagcctctg caccagagct  14640
ggcacctgct tctccgtggc cccagctcc tctctggcca ggccccagc agcccatgaa  14700
acagaaagca aatttcacca gagacaccca tggaagccct acgagaaacg ccttcccccc  14760
aagaacaagg ccagggggcc gcgtgtgccc cacccgctgc acgcaccgtc cagcagcgta  14820
tagttgagct gcagatgcag cccggccgca gggttgctgc tgtccagggt gaccacagca  14880
ccgacggagg cctggggctg gaccacaacg gagttggcgg agttggcgga gctgcggtgg  14940
ccccgggcag cccagtccga gttgttgggc accttcacgg tgatggcgcg ctctgaggcc  15000
agccgctcga tggggatctg ggcgccggcc tgtgtctgga atgccatcga ggccaccttg  15060
gtggagacgg tgtagttgct gatatagcca aagggaaagg gattggagtc caccagaaag  15120
atgagctgca ccacgtcact gaggttggcc agggccccgc tgaaagcctc ggggatggag  15180
aagtggcagc caggccctgg ggcgccgcca tagcacagca ggctccgcgg gtccgagcgc  15240
ttgccctggg ccacgatctc ctcgcccgcc agcgtcaggg gctcctcgtt gagcacgcgg  15300
gagcgcatga ggatgcgcat gagggcagag gtcaggttgt aggcctggga cgccaccatc  15360
cgagatggtg actcggctcc cagctctgag ggctgtggtg cccgcacgtc cgagctggcc  15420
aggtggatga ggtctcctgc agacatgcgt gaggtcagtg cagagacagg gaggtagagg  15480
gagggtgggg gcaggcaaaa agggggagcc ggagggtggg ggctgggaga aagggggaac  15540
ctgaggggc agagagcgag gtgcaggcag aaggaagggg gaagctggag agagagtggt  15600
ggaggggga gggggaaggt gatggggatg aggacgaaga tgagggggat gatggggaga  15660
gggaggaaaa aggaaggaaa agggtagaga aaagagaagg gagaagaaga ggagcagggg  15720
gaaagggagg ggaaggggga taagggaggg gaagggggat gagggggatg aggaagatga  15780
ggggaatgga caaaaggacg gggaggacgg ggggggaaat ggagaaaagg ggagagagat  15840
ggagaaaagg gatggtaata gggaaggggg agggggagga gaatgggaat tgggggaggg  15900
ggatgaggat gggaattggg gggaggggag ggggacgaag atgggatggg gcaaaggcga  15960
cgcggttggg gggaggaggg aggcagagga aagggccgca cggggcgggc gggtggcatg  16020
gggcacgggc cgcggcacct gtgatgttga ggatgctgtc tccgatggcg gtgggcgtca  16080
cggtgcccgc ggtggtctct gcctgcagga tgagcatcat ggcctccagc ttgtgcagcg  16140
tctgcttcag gcacgagcgg catacgagct ccctgctggg cccctgtgtg gagccagcag  16200
tgtccagccc cgctcctggc cccactcctt gcacacgccc tcctctctac acggtcctc  16260
acctggctcc cacccccagc cctgcagctg gagagcccac ttgactggac ccccacagcc  16320
tcctcactaa gcattttctg tggctctgca tgacccaggg cctccacctg gggaccacgt  16380
gatgcagccc accgaccaca caaggcacct cttcacatga gagcggagga ggaggggaga  16440
gaggagaggg gagtggagaa aaaggggagg ggaggagggg aagggctggg ggggaagaag  16500
ggaaagggct aggggagggg aggaggggaa gggctagggg aggggaggag gggaggggct  16560
aggggaggga agggggaggg gaggggaggg gagagtggag ggcacagagc agcatcttct  16620
tagtccctcc ccacatctgg gcccctcttt acaccctggg tcccccgaga ggcaccctgc  16680
gttcacacag gacagaacgg ctgaggctac tgaagcaggt cagagaccga ggaacgccat  16740
```

ggcaggaagg agcccaggct ggaggctcag ctcctcggcc aagctgcccg tctgccctgg 16800
ggggctgaac ccagtgccct ggcaggcatg cggggcaggg tgagcaggtg gggccatcct 16860
accatgcact gggccagcgc agcagcgatc tgctggatgt catccacagt gtggaccctc 16920
agggacacca gagtctccgt gatgttcttg cgtatctggg ctcggtgctg ccgctcgtgc 16980
ttgggctctg ccgccacgtc cagggcccgc tcgtactggg gcaggcaggg ggcacagcaa 17040
gctgtcagca gcgcaggagg ccggcaggag gccagcagat gcccacgact cccggggtgc 17100
agttacgtgc tagacgctgt gtgatgcggg cactgaccca caacactgag ctgtttcttc 17160
atgggcaaaa cagggtaagc acatgggccc tcctgggcgg gggctgcatt gtggaaagca 17220
gacgccggag agggcccggt gggtgtggct gctgggagcg gaaggtcggg gtgctgcttc 17280
agggtcactg ggatttatct ctggggcccg ggatgagccc tctgcaaagc tccaggcagg 17340
ggtacaggtc ttggtcccaa gcacgcatgc agcagatgtg acgtcccctc ccaggctgca 17400
ctcacctcgt tcagcacggt gaccagggcc aacgagtact cgatgacgtg ctggggatcg 17460
gcctgccgca gcagccctgg gagcacacta gcggtgagcc cgtgcagcca gactgtgagc 17520
cccgttgcgc tgccgttggg ctctgggagg gtgatggcca aagacctacg agcagagggg 17580
ggtggtgagc aggtggcagt ctcgggggcg ccctcccacg gcctggctca cctgttgagg 17640
gcgaccacag cggctcccag ctggtcctgc accaccacgg ccaggcccac ctcgaagtgt 17700
ggcctgaaac ccgggggcag cacggctccg tagctggaga ggctgccctt gtagacacag 17760
aactcctcgc agtggccctg gcgacagcgc cgcagcagca gggcgtacac cagcggggcg 17820
ccagcatcct ccgcgtcatg ccagcctgag ggacggtccc cacggcatca cgggagggct 17880
ccgtgacgtc acagagtcgg gggatcccgc tgctcccccc acgcaggcct gcactcaccc 17940
gtgcattcga agtgcacctt ggtggtgagg gcgtgcacag cgcccagtgg gaagaggcgg 18000
caagagcccc ccagcggcgg gcggttgggg gacaggcgga tggaggcgca gccctcctcc 18060
tcgccagagc ggcccagcac cgtgagcgtg aaggtgtatc cctcgccgtc ccgcagcacg 18120
ccccgccgca gcaccagtcg catgcctgca ctgcccgtgg atgtggtggt ctcatccagc 18180
accagcgtct tgttgctgaa cgtacgtgca gcccaccgct gcaggcagaa ggggtggtga 18240
gggggcgcaa ccctctgccc tgtcagcccc acttctgcct gcaggccccg tcccctcggc 18300
catgggaccc atccccagcc cgcccacacc ccgctcaaca ctcacccctc gcttggagcc 18360
gctgctgcaa ttgaggcagc ggccctccaa gtacacgtag gagctgcggc tcacttcgta 18420
cacggcctgt gccttgcagg acacacactc caaggacaca atgggcaccc ggccactccg 18480
gatcagcacc tggcgtggga gtggggttac ctccaacaca ggtctatttg gcctgctgga 18540
aggactgggg gacccatgga ggatgctgct cccaaactcc aggtttccca ggggcctggc 18600
cactgccggt gagctcactc cctcccagga tactcatccg gtttgccacc ttccaacttg 18660
gacggcggaa gggcatacac agggcagagg acactggagt gtgcgttctg gtgtactgga 18720
cccagctgga ccctagcagg aggcaggcaa tgctcactga gggcccctgg ggggatgcgt 18780
gtgagaagag acgtatgtgt gggtgtgagg accgcagctg ccacgtaggc ctgactcaca 18840
gactcctgca gcccttagcc agggcctggg tcaggaggct gagctgggat ggaacctgct 18900
cccacaccct cccctcagac gacccctctg ggaagacccc caatcaggcc agctgaggaa 18960
agcagggact ggggaacaga cgcccactct ggggcaccag caggccccgc ctgacagcag 19020
caggagcagc caccacgggc tcagggtcac caagcctcct ggccggtcca gagaggggag 19080

```
cgtgagggtg agaaccggcc caccacatcc agcaacaggg acatgggctg gggacagtgg  19140
ctacctctgg ggtgggaagg ggctcttcct cactgttggt attgctaggg gactgtgtag  19200
cttttgccac tagagcatat gtggcttgaa gactgtacgt ggaactgtgg caggtttgga  19260
aggaagcaaa gctgaagcag gctgtcgtgt tacatagaat ttgcatcaga aacagagagg  19320
ggagagcgtg cggcctccac cagcactaaa acacggaaaa cagtagatga ccagggaggc  19380
tgggctgtcc aaggcaagtg gccgaggggc gggcggcacc caccgtctgg ttggtggcct  19440
cctccttgcg gccggccttc cacacggtca ggctgaaggt gtactccacg ccagccgcca  19500
gccgctcccg tggaatggtg accgtgctgc tcccgcgggg cccaaagttc agcgcacacc  19560
cgccagcctc cctctgcagg ccgagaacaa ggggcgacgt ggcctgagag ccccatccag  19620
ttttaaagca gagcccggcc caggagacag cgcgggagac cccctcccca tgctgggacg  19680
gggcccacca ggcactgagg acgggccagc cctggtggca agctgggtgt tctctgggct  19740
catgggtgtg gacgggtgag gggcatggag gacggccctg ccacgcactg acctgtgtcg  19800
aagccacaca ggcccagtgg aaactgagcg gcgtctggtc gccgtcctcc aggttggggt  19860
cgtaggactc gctcccatcc agcaccaggt cccgtgtgtc tgaccacacg cggtatgagc  19920
caccctcaat gatgggcacc aggcgctcgg gggccaccgt cacattggcc tggatgctct  19980
gtgtcagtgg cgtgtcccca aatgacacga caaacacaaa gcagtagtgc cccacaggca  20040
gcgccagccg cggcagcacc agccgaggcc ggctcacgtc cacgccgggc agggccacac  20100
gcgctgggcg ccccggccgc tggcagctgg cggtgcgata cacctcccag cggtactcag  20160
tctggtaggt gacgcagtcg cgcaggtcaa cgtgggcctc caagtagttg cgctgtgatc  20220
gccgcatcag cacctgcagg ggcaggacca cgtccacctc cggctcccgg caggccagca  20280
cctggacggt caccgtggcc tgcgccacga agaagctcac caggttggag gcgttcacct  20340
gcacgcggta gtccccaggc ctcaggtagg agtgctcggc cctgggctca tctgtgtcct  20400
gccctggcga cccatcccca aagtcccagt ggtaggccac acgccggggg ctggggctgg  20460
tggcggcctc aaactgcgcc gagcggttgg tgaagcaggg gccgctctgc agggccacat  20520
actggacggc gtcctgaacc tccagcacca gcgtgcggtt ctcactgccc agggcgttga  20580
aggcgcgcac ctggatctcc aacagccccg cggccacggg cgtgtaggtg acgtcgcggc  20640
ccgacaggat gaccagcgag tcgccctgga ccttctgcag cgagaagtac caggcgtagg  20700
cgacccgaga gccgcgctgc acgcgggctg tgaagttcct ctcagtgccc gtggcgatgc  20760
caggctcgca gcagttgggc acctgcagcc cactcacggc ctccagcacc acgatgcgca  20820
cctgcgcctg ggcccagctc acgtggtttt tgccccgcac gctcaccacg tggtctccga  20880
cgcgggggaa gctgtgggag aaacggggcc cggggagcac ctcggggttg gccccgccga  20940
cctgcaggcg gaaggtgaca gctgagccgg cagccagcag gatctgaaaa tggaccagct  21000
gcccgggcgc caccaccttg ctgctggccc acagcaccag gcccacgatg ggctcctccg  21060
ccgtgaggtt gtacgtggct gagacccagc tgactgcgtt ggaggcattg agccggatgg  21120
agaaggtgcc agcatccggg aagaccatgg tgacatgagg gccacgcttg ctgctgccgc  21180
cgggcacagc ccagcaccag ctcacattgg tgcccgtggc cagctgcccc caaaagggca  21240
cagaggaccc ggccgccacg aagctgcctc cgggctcgct ggccctgatg ctgaggccac  21300
tcacaggcac ctgcacatcc acttccacgg tggcgttggc tgagcccagc gggttccctg  21360
ccgtcatggt gaccaagtgc aggccgggtg tggggaagct atgggtggta aatggctcgg  21420
aggtctccca gctcagcccc tcctccaagg accaagtgta tacgacacca ctgccaccag  21480
```

-continued

```
ccagctcggc actgagggtg acgcttgtgt tgacggcagc tgggttcggg gaggcggcca  21540
ccatcagcca ccccacaggc tccacgaagt ccatggtgca gtcggcccag gcgctgccca  21600
gcatgttggt ggcccgcagc tgcacatggt aggtgccggc ctcgagcacg gtgagcgaga  21660
agcctttgcc gctgccggcc agggccgggc ccctgtccct ccaggcagtc cagctgtagg  21720
agacgttggt gccatcccta accacggcct gcagctgtac cgtgtggttg gtggggaagt  21780
agcggccacc gcccaccacc tgcagcccct ctatgagctg caggacatag acgaagatgc  21840
tgtcctgggc ggagcccacc tcgttctcag ccgtgacgat gatattgaag gtgcccacgg  21900
agcggaaggt gtaagagatg gtaggacccc cagggatggg cgtgcagcgg tcacagagca  21960
cccaggaata gcgcacatca ctgccggcct ccagcgacgt gctgaagctc acgctcccat  22020
tcaggggcac caccgtgcgg cttgcattga cgacgagccc ccgcacgcgc cgcttcaccg  22080
tcacattgag ccaggcctcg ctgcggctca cctcattcca gccggccacc ctaacggtga  22140
agtcacctgt gctgttgtaa gcgtgggtga cctccggacc ctcgagccac ccaccgtccc  22200
ccagatccca caggtagctg gcggggcgcc cacggcccac agcagagaac aggtacggct  22260
gctgcagctc cagcccaagg gagccattga ccttgatgct ggtgaccagc acgggctcct  22320
gcacctccac cagggctgag tcattggcag cagagatgtt gttggacgcg gtgactgtca  22380
caagatagga gcctgggtct cggtagatga acgtcacctc agggcccctg gcacgggtgg  22440
gggcggcttc ctcggtgcca aagtcccagg tgtagcggta ggggaacggg ggccaggcac  22500
atgccaccag ccaggcctcg tccccgagct gcacaaactg cctctctggc tgcagggtga  22560
cgttgcccac ctctggctcc acgcagatgc tggtgaagta atgcgccctg ttcacgcggc  22620
tggacagcac cagcgccagg gggaacgtgc cgctccgcgt gaagttgtgt gtcaccgtcg  22680
ggcacccccg cacggtcgtg ttggaggagc catccccgaa ggtccagtcg aagaggtagt  22740
gggccgggtt cccggtgacg taggccgtga gccgcgcgtc aggctgcgtg gggatgcagg  22800
cggcgggttc aacgcgcagc acctccagga cgaagaccag cacgtgcagg ctccgggcca  22860
ggtggccggc ggggctggcc gcacccacgg tcactgtgca gttctgtgcc cgcaggtaca  22920
catgctccac tgttgcctcc gggcccgaca gcacggtgcc gtccccccatg tcgaaggtcc  22980
acgtgatgtt gtcgcccgtc tgcaccgcgg cgctgaccac cacgggggcg ccctgctcca  23040
cggccaggct catgtccacg ctgagtccgc ggagctcctc aaagacgcgc acatccgcct  23100
gggccgccgc accgctcacc gtgttgttga cctccaggcg cacgtggtag gtgcccctcg  23160
aggcataggt gtggttggca gccggctggc tctgggtcag gacaggggag ccgtccccga  23220
agtcccacgt gtaaagaaca cccccaggcg agggcagcgg gtgcgggtag aaggtgacgg  23280
gccggccggc caccaggacg ccgtcactca cacccacagc cacggagggc agggaggcgc  23340
gcacgctcac aggcacctgc tgcgtcaggt tctcgaaggc attagatgcc agcacggtca  23400
ggaggtactc acctgtgggg acaggcccga gtggggcagc cgcggcaccc ccacctgctc  23460
cccacccgct cggcagaagc cccccgcctg aggagcccgg ggtgaacggc tgcacctgcg  23520
gcccagcctt aagggtccca ggctcccaag ccacgtgcgg gacggagcac aggtgtagca  23580
gcactgaggg ctgcctggcg aggacggcac cgcctccaag tgcagctgca ctcggggcag  23640
cagagcagca agagccaggc ccggggaggg cggggggcgc agttcagggg cccagcttcc  23700
ctgtccactc cccccacgcc tggcccctcc ctcaccccag taggggccta agccatcagc  23760
ccaggtgagg tcacagtgag ggctgttggg gaggaagggg ggcagcttga ctggggagct  23820
```

gggggggaccc cgtgctcaga gcctgaaagg cagtggcccc ctcacccccct catccctcac 23880 ctggggcagc gtaggtgtgc atgacattgt gctccaccag cacctgggcc accgaggggt 23940
ctggaaccgg gaaggactcg ttgtacggag gctggaactg gtggagggcc tgctccccat 24000
ccccaaaggt ccacctgccg gggcggtggg acgcagtgag tgaaccggga caggggtggg 24060
cggtggcggg gcagggggtg cttgggaccc agccgaggct ccactctgca gtcacgcccc 24120
gggcctccat tcagggccca cccggctgtg ctgaggcctc tcccggctcc cgtgcagcct 24180
cagggctcct gtgcacccag ttacctccca acagacaggg aaaccgaggc tcagaaaagc 24240
aaccccgtga tgtgggggtc cctcggctga ggctggggct gggacaagag cctggtgccc 24300
accccaaacc ggcccccgag tcactcacag gaaggccacc tccacggccg agtccaccag 24360
cacgcccgcc gtcagtgcta gcgtggcatt gggggacagc acggccggca ctgtggagac 24420
ctgcagaccc tgcatcctgt tcatccgctc cacggttacg ttgtagttca cggtgacgtt 24480
gctcacgtgg ttggaggccg tcagctgcag ggacaggcgt cagtgagccc aggtggcagg 24540
tgagaggcct ggccctgatt ggcgtccctc cctccactca cccacagcca tggcagcgtc 24600
ctcgggcagc atgaagcaga gcagaaggca gaggtgaagg tggagcccgc ccccgccctg 24660
ccccgcccca tcccctcccc tccccacccc cgcccaccta ctgagagctt gaagaccgcc 24720
gcgctctgat aaatgacatt gaagaccacg ttctggaagg tcagggactg cttgtcgttg 24780
atggtccacc ggaagaccat gtccgagccg gcctccacca cggggctgta cctctgcggg 24840
gggaatggtg tcagcctggg ctctgtggag gactctgccc ttagcctgtc gcctcctgga 24900
cacacctccc gtcgggctgg agagtcccac gcggggcaca gaggagagga ggtgcccggg 24960
gctctgcatg ccatgggagc caagcccggg ctgggacact cactgtccgg ctctccagcc 25020
agccatgtag tactactaat gcctcaacct ctctgtgcct cagtttcccc atctgtaaag 25080
caaacctagt accagctaca aagagtccac ctctctctga gtcttctcag accctcccgg 25140
cgctcttgcc ccagctcctc acccagagag ctcggagcag tgaggggagg cacctacact 25200
ggcttacaga acccaggaca ggctgcacag gtcacgccat ttctgatggc cctcccaag 25260 gcccctggtg aagaggcagg tacccgcaag atggagacag ccctgtcccc catgtaccca 25320
gcatggtggc accgcgggca gcccgcagtt tcccatcagg ggttcagact ccacctcaaa 25380
agccactcgc tttagccagg cgagaacaca gcagagggcg tgagagactc acgggggctc 25440
gtgtgaggtc agggagcaga gttttaaatt cattttgtga aatgagacag tggaatgagt 25500
tagcggagcc actgtcagag ccgtgacttt ccaggaattt aaagcccacc aggtagcccg 25560
aggagccagc cagcaggacc tgcccggggc cgacgtcccc agtaactggg ctgctgccct 25620
cactgggaag ccaggcctca cgccctgtgt gagcaccctg tctgcaggca cctgcctggg 25680
ggctggtggt ggagcctcgg ccatactcac cactaggact ccctgcagta cacgggcctc 25740
ggggctgggc gtggcgcgga ggccacagat gggctcctcc gccgtcaccc gcaggctgag 25800
gttggcccgg ctggcgctgt tttccaccac cacgtccacc acgtgctccc cctcactgag 25860
ccacggcagt gctaccactg agaacagggt atcgttggtc tcccaggggc agccgggcac 25920
gaaggtggcc accagggcag ggcagacatt ctcaaagcgg gcgctgacac tgccccccagg 25980 ccagcgagcc gtggccgtgg cgttggcacc agagtccacc tggagcacca aggctgagcc 26040
gttggtgggc acgtagaggc ggccgtcgcg gggggcaggg tagatgaccc gcagcccagc 26100
cactggggag accacgtcaa agctgcagga gaggttgtgc ctggacacgc cattgcccac 26160
ctctgcccgg acctcatagc gcccaggcag ccgcagtcca gggttgggcc tcaagcccag 26220

-continued

```
cagcacggtg agctgttccg tggctgcaag cagccgcagg gcacaggcag ggcaggccca  26280
agtgccctcc agctgggctg gcaagtgggg cagccatgac gaggcgttgg cggagaggta  26340
cggggcccgg ggaccagggt ggccgggagc cggcgagcag tgcaggaggg cgccagggcc  26400
agcgtcgtgc tgcaagccaa cgaggtcacc agggagcatg aggacatcct ggccgtggag  26460
ggtgacctgt ggagagggag gcagggctgc atcacgtcct cacggtcatg gcccgtggac  26520
ccccgcacga cggatgaggg tggacacgca gggctccccg cttcgtcagc cacacctcaa  26580
ggagcctccc cacagtgctc gtgacaagga caggcaggac agttgcagac cgggggacac  26640
acggggagag gacacaggcc aagacctggc agacaggaag gagcagctgt gctgggagag  26700
aggaagagga ggcacagctc gtgccaaggg cccaggcgag agcttctccc actgggagag  26760
ggccgagggc actgcagagg tcggaggtca gaggtggcaa ggacgtggga ggggcctgca  26820
ggctgggtgt gtctggtgca cagacccaga ccctgggcag cagacaggaa ggtggcctga  26880
ggagatgcag ggaacagacc caggtcaggg ccacacaccg agtactgcgc ggggggcccc  26940
gcgggaacgg agaagaggaa ctctctccat agcgcatagg gggcccgggg tagccctggc  27000
cctgacgtgc agccattggc gcaggcctgg gggtggcagg aggcgtccag cggcaagcag  27060
atgttggctc cagggcacca gcgtcccccct ggcatgcacg cgggggccag ctgggtcctg  27120
ttgtccgggg acctgctctc aggctcgctg ccgttctccg gggtccctgt gaggagggga  27180
gggtgttggg gccctgattt gcccacaggc caccgtcaga gatgcccaac tgcctgcacc  27240
agcaatcctg gccttgctgt gaggacaggt ctccccacct gggcagcact cccagcccag  27300
tgctgcgtcc gtctccggcc agccgactga cccaggccgg cccccaggca ggccccaccc  27360
aatccacccc caggacacct ggaatgagct ggtgtctctg gaacccctgc tctgtccacc  27420
taagactggg aaccactctg gtggccacag gaccagcaga cgtgaaagct cagagaggcc  27480
accccgagtc ctgcggcgcc caccacccac cacccaccac ccagagtccc acctgctgtg  27540
ctgaggagcc ggtacacctg cagccgcagc tgggcgggcc gccggagctc ctgggtccca  27600
aattcggccg tggtgaggaa ggcttcacgg ctcagacgca ggcccgggaa taccatgacc  27660
tggtgggcag gggccgcct cagctccaca gaccccatcc cagcctgaag cccagactcc  27720
ccctacccga acttcccagg aagaggggag ggaaggagag cgagccatca gacccccaca  27780
ggcctggctc ctgtcgctcg agaggaagac tccggtggaa actgtccatg gggggcagga  27840
cccctgacct gcctttcagg aataactcac acacgctcag agaaaaggcc tggaggtaat  27900
gtgagtaaac gctttcctct ctgcactctg gattttccca accatcttca ctgggcacaa  27960
gcaacattaa ggcccccaag ttttttggcg agacccacag tgggcagggc aggcaaggcc  28020
tccaggggca ggcaggaggg caggttgtag aacgtggggg gccgactacc tccacgggct  28080
cgtgcggggc tgagaggccg tcctgctgtg ccagaggcgt caggggtccc tgcaggtccc  28140
cactgggcgc tcccacgagg aggttctcgg catcctgcac tgggcctggg gtggcgagtg  28200
cacagtgagg cgccgggcca gggcccagga caccaggacg aacagactgg ggaccgagcc  28260
gcccgaaaac ccccccacca gcccctcctc ctcagcccag gctccaccgc gggcgctcgg  28320
caggccccta accacagcca gcgtctcagg cccctgcctg gcccccccgca cacctccggg  28380
ctgcagctcg cagacgtagc tgtgcggcgc tgagcacagg tcggtgttac accacccggt  28440
gggcccgagc cggacgcagt gctcggctgt ggctgggtgt ggctccccgg gcagccagtt  28500
ctggcagctc tccaggctga aggcctcgcc ctgcggcgct gggcccacct ccacccccctg  28560
```

-continued cacagtcgag aagccgatcc acacgtctag gctcctgggg gcgggtgtgg gatggcaggg 28620
ggctcagggc actcctccat cctcccaccc tcacagcagc ccgctgggag ccccatcact 28680
gtcccccttt ccagatgggg aaactgaggc tcagagcccg gagaccaggg cccaccagcc 28740
caggctcaca gcagcaccca cccacggggc ctgtgggtac cggcagggat ccccgtgcag 28800
gccacctccc gtatggcgtg cccaggagtg tccggaggct gcccccagct catgtccacc 28860
tctgcatctg cagagctgac aggaacggcc ccaccggccg gcgccacctg ctcaccaggg 28920
ccggcccagc tcccacctcc ttcctcctga gactccccag ccgcaggctc tgccccagtg 28980
cttcagagat ctcccaacct atggcccctc ggggggtggg ggcaggcacc tggtgacccg 29040
ggagaccagg aagcgctgca cggcgggact gtccaccatt gccagggcgg ccccggccca 29100
ggcctgacac tgctcctgcg cctgcagcca ggccgccttc tccaccacca ggcggtagca 29160
gtgcccgttg ccagggaaga tctccgtgtc cgaggggcag agcgggtgca ccgctggaga 29220
ccggtgggaa cgagggtgtc aacggtcagt gtgggcccaa gacgggggta ccaggctctg 29280
ccccatctgg atggccctgg ggaggaaggg gagtgggcag cagacactca cctcgggccg 29340
gctcctcgcc cagggccacg atgctgtagg cggcctccag gcctgaacca ccgcggttct 29400
ggatgctgag gtcgaggctc tcgtcactct gcaccgagga cgggcacacg agctccaggg 29460
cggcaggtgc cgcttccacc tgcacgtctg tccccagcag ggctgagccg gcccccaggg 29520
ccagcacggc cgtcacgtga tagcgcccag gcagcacata gcgatgcgag gcagccggcc 29580
cagcggcatc cacctcggcg gagccgtctc cgaagtccca gcgtgtggca gtgacaggga 29640
gcggggcagc gatgtggaag gctgctagct ggccagaggc cagaggtccg tggggcccca 29700
ccagggtggc ccctggggag gcagggaaga cgtgctggag gagggtgggg cccctacagg 29760
tgggggcagg aggtggcggg gggccggagc agagggacag gcaggcaaag gaggcactgg 29820
agggctgggc cgccccacac aggcaccagc cctgctccga gagggctgcg aggccctggc 29880
cggtggagaa gcagaaggcg ctgcaggcct ctggctgaag caggccttcg tgggcagctg 29940
aaaaggacac tgctgccacg gtgcctgagc tgttgtcagg gaggcaggcg acatactcct 30000
cacctagaag aggcagccac tggaccccgg gttctgctcc tcctggctcc accccacgcc 30060
cccacatccg cccgccgcac tcacaggctc ccatgctgtt cccttggccc ggaggccccc 30120
cccagagagg ccttcctgag ccctgcccag tgtctgcagg gcccaggtcc cacctggctg 30180
ggaaggacag agctggcccc acccaccggc actcaccaca gccactgtcc agcaagggga 30240
tgccaagcag aggctggcca gccagggagc caggcccagc acacgtggct gcctcgggct 30300
gcaccacccg cacctgctgc tcctccgccc atcgcggcag ccacgccagg ccacagtcac 30360
actcaaacgg gttcccactc aggtttctgc agggcagggg caggtgttgg ggaccaggtc 30420
tggtgggaag ggtctatgcc agccccccac tggcaaccag gccctggagc caccctgaca 30480
gcaccgcctc ccctgcccca accaagccgg cactgggggg ctccaagcag gcagtgaact 30540
gcccccagga tctggtctca agcctggaag gggacacgga ccaactggga gggcagaagg 30600
gatattgggg gcctggggtc cagccaggac ccccacccaaa gaaccacaac ttacatttca 30660
cttaaattaa ataaattagc aaatattcct tcttctaacg tagaaatctt gttgttgctt 30720
atatccctgg aagagacggg ggattcggca aagctgatgg aagcccccac agctgagcag 30780
caagaggcgg tgccgccagc ccacccggag tgagccccgc atgctggcac gactggggga 30840
cactcacagc tctgccagcg ccgagaggtt cgccaggagc ccaacgtcca gcgcccggag 30900
caggttgtgg gagacgtctc tgaggagtga gtggccgtgg gtcagggcca gagcccctag 30960

-continued

```
taggccagag gccatccctg ggcccatccc acacattgcc agcatcccca agctatggcc  31020
tcccaccctt gagctcccca ctcccagagg tcaggagggg actttctgat ggaagaccca  31080
aatgaacact catctgggga aaccaagcca ggagaggcct gggggcctca gccctctgca  31140
cccatctcag ccctatgccg agtgccacat ggacctgtcc acccagggcc aggaagggca  31200
cggaccccca acccatccca cgcagggcca aggcccccca tcccctgtcc acagtccccc  31260
acagagccaa ggtctcccaa ccctgtccac agcccccaca cagactcgag gggcccccat  31320
ctcctgttct gaacccaaca gggtggtccc actgtgggac cacaaccagg tatgactgtg  31380
tgagaagcag gctcactacc aggctaccag ggagcacagg ggagcaggcg ccacctcgag  31440
gcataaaccc agagaaacaa gacctccaag acggccaggc actggggcac acgccggtaa  31500
cacagcaccg tgggagctga gacggaagga tcgcctgggc ccaggatttt gaaaccaccc  31560
tgggcaacac agtgagaccc cgtatctaca aaaaatacac attagccagg catggcggca  31620
tgcgcctggg gtcccaagta ctcgggaggt agaggagaga aaaatcactt gagcccagag  31680
aggtcaaggc tacagggagc tgagatcgca tcactgtact ccagcctggg tgaaacggcg  31740
agactctacc tcaaaaataa ataaatacat acataattaa taaataaaac atcaaagacc  31800
agccgaccta actccatcta aaatacacaa cttctacgca aaatataaat aaaattagaa  31860
aacaaactac aatctcagaa aagcactagc aacttacacg acatactaaa ggccaaaaat  31920
accctcctga cacacagcta ataaagaaaa cgtcaactat tccagttaaa aagaagaaaa  31980
ggaaactggg tgtggtggct tatgcctgta aacccagtgc tttgggaagg ccaggagttt  32040
gagaccagga tggacagcat agcaagaccc catctctaca aggaaaaaaa gaatcagcca  32100
ggcatggtag tgtgtaactg tagttccagc tactcggggg gctgaggagg aaggatcgct  32160
tgagccaggg aagtcgaggc tgcagtgagc tatgattgtg ccactgcagt ccagcctggg  32220
cgacagagca agacccggtc tcgaaagaaa acaaagagaa agcaaggaaa gaaagatggc  32280
cgggcacggt ggctcactcc tgtaatgcca gaactttggg aggccaaggt gggtggatca  32340
tgagatcaag agatcgagac catcctggcc aacagggtga aaccctgtct ctactaaaaa  32400
tgcaaaaatt agccgggcat ggcggcggga gcctgtagtg ccagccactc aggaggctga  32460
ggcaggagaa tcacgtgaac ccgggaggcg aaggttgcag tgagccaaga tcacgccact  32520
gcaatccagc ctggtgacag agcgagactc catctcaaaa gaaaaaaaaa agaaaagaaa  32580
agaaagaaag ggaggagaga gagaagaaaa ggagaagggg aaagagccgg gtgcaatggc  32640
tcctgcctgt aatcccagca ctttgggagg ctgaggcggg cgcatcacct gaggtcagga  32700
gttcaagacc agaccgacca acacggagac accctgtctc taccaaaact acagaattag  32760
tcgggcgtgg tggcaagcac ctgtaattcc agctactcag gaggcttagg caggagaatc  32820
acttgaaccc gcgaggcaga ggttgcagtg agctgagatc gcacccctgc actccagcac  32880
cccatcctgc aagagtgaag ctccatctca aaaaataaaa ataaaaaaaa aaaggatgga  32940
gggtgagagg gagggaggaa agaaagagaa aactccaaaa acaaaaaaag aaaaaccagg  33000
caattagaag aagcacaatt ggtcacagcc gtaggaaaaa catcccatgt cagtagtcag  33060
tgaagaaaaa gcaacagaaa ccacagggcg gcagcatgtc tctcttttca gagctgcccg  33120
agttacaaac caggtcctgg agctggtgat gcggaggtga gtagacagag agctggggca  33180
aaccgagaac tccacctccc ctcggcctca agcacctcgg gggtcactct gccgcccacc  33240
ctgggcaccc ctcctggtcc cacgcactcc cagtagtgct cctggcacag gactatggct  33300
```

-continued

```
ccgcaggtct gcacaccacc cccctgctcc ccaggacccc gaggcctcac ctcctgccac  33360
gggcctctac ttccccaggt gtcaccctcc ccacgagtga cccagcaggt gcctccgcct  33420
agacttgctc ttcccagcaa tgaccacccg gcagccagcc ccaagccggg gcggcctcca  33480
tccctgaaca cccgcccagc ccctgccagc ctccagccct gctcctccca ccggagctcc  33540
gctcccacag gagcctaccc ggcgcaggag agacgcacac acaggctgcc cggtggggcc  33600
cggggccagg gcaagagctt gagaagggaa ccaacaaaga aggggaccag aggccacccc  33660
agctgagggg acagagcagc cgaggccttc tccgtgccag gaagcagcac cagccacgga  33720
cggtggagcc aggccctcac ctgggctggg tgcccagaca gatgagacgc tgggcactgg  33780
ctcccggagc ttctcgttcc atctgcggat ggagggcacg gttgggggtg cagttccctt  33840
cccccagggg ctgtgggaca ctcagagagc ctatgcctgt gccctgggct ccgggagggg  33900
agaggatctg gggggccaggc acacagggaa cggcccctcc ggcagggcca ccacttcccc  33960
cctaactgaa ccctgcttct ctgccgtccc ctcctctaca ccaaggtagg gacacgggct  34020
gaggtgctcc ccactgccca taaggatggg tgggcccaca gccgcgctgc taggcatcca  34080
caccatcccc gccgtggggt gggacagggt ggtggctggg agaccagcaa gaggccattc  34140
tcgagacagg gtgaggcagc tggactcaca cccactgccc aagcaccatg cccgaggggg  34200
aacactgtgc cgtgaggaac tgcagttaga cctgaggagg gactttccag cggctgcggc  34260
ggcagcagaa ccaatgcttt agggagaaat gaggcaccgg gacccgaggc gcaggagccc  34320
taaggggcga gaggtgctgc agaggccacg gtgaacacag gcaggccccc tggaagggac  34380
acagctgtga aactgcccca gggaggggca caggctctcg cacctgcccc caggcatggg  34440
gagcagctcc cacccaggcc acgggagaaa ggaaagaagg aaaagcctga agatgtttgg  34500
ccacacctca ttttctggaa aatccatcaa gagtggctgc tgctgggagc tgacaagcca  34560
gggcaggggt gggggcaggt cagccgagga ccccagagcc ccccggctcc ccgcccatcc  34620
cactgtgaac caggcctggg ggtgccatgg acacttcttc cacgccagca ggcagccctg  34680
cctgtcaccg gttctggcca tgcactccct gcgtgccagg ctccaggctg gctccttctc  34740
ccggccctca ccccagccca aggcccagaa atgcagcaag gtcttgggga ccccgctcgg  34800
ccgagctccc agggcccagg gcagtggaat gaagctgggg cccagacagg agccaggtgc  34860
agtcccccag cccccagggt gtggaagcgt ctgccctggg taggactcag gtgcccccctg  34920
ggtgtggaag catctgccct gggcaggact caggtgtggg cttcagggac agggaacagc  34980
acaggggtcc ccgtggagtc ctcacctcgc ttgctcccgt actttttcac gtctccatct  35040
gcttttgcca tcgccgttct gggggaacgc caaggcctag ccaggcagcc tcgcgccagc  35100
ccccccaccc cgcccctcgg gcttcctctg cacccgccag gtgacatcat cgccgctgtc  35160
tgatgccctg cccccacgtt ctggttccct gcaaggatgg gggacacagc agggcccagg  35220
catctggcag caggaccacc gagcggccct aagcccaggc aagagcacag agcagagtgc  35280
agggtcctct ggggtcccag gcccttgctg ccccacgcac tcctcacccc agttcctgct  35340
atgagctgga agggtgggag ccaggtgcac agggacagcc tgatgggtgc ccgagggcca  35400
ggatgtgctc ccagggaagc tgaagccaag cttgtcggga ggagtacacc cccatggggg  35460
gcaggacggt gccccagccc cgggacacaa ggggtcccca gcgccgagcg tccgatctgg  35520
aaggcgggag gagttaggac catcctagcg tgggacccag cgggctcctt agcggctgct  35580
ggggcaccac tgggtggaga aggaagtccc aggtgtgtgg ccacagtacg ggtcttcacc  35640
ccttcccagc acccttgcca atcctggagc aggagcagca acagcagagg gtgtggccag  35700
```

-continued

```
gcctggaggc tgcccctcca cacccgtcac aggtggggcc acgtcccagg gctgtgggca  35760
gcagggccag cctgccggcc cgaggtagct gacacgtgtc tcatgctgca gcgggtctgc  35820
ccgccacccg ggcgtgtgaa ccccaggtcg ggccccctcg ccctggagcc tcggcccctc  35880
aggggtgttc ccagccaggc gctggctctc ctgccctccc cctgggctct gcccacagtt  35940
ggcgcgaggg tgggtgaagc ctgaggctgg cagggccggg aagtcttggg gctgggcctt  36000
ctgccccaca ggcgctcctg ggccggggga gccggggtcg gggaatgcaa cagtgggact  36060
gaggagaact tccctgggtg tggggcagct cccggggccc tcccaatcca cagcagaggg  36120
aatggcccca gacaaaccag acctgcctca gagtctcaca ctcagagctg agtgccccag  36180
gcgcccactc cccagaccag atgctgagtg gggtctgggg gccggacgga gcccccaaag  36240
aaacatctgc acattccaga cacgtgtggt cagcagcggg tgtgcgccag gcccggcacc  36300
cccgcccgcg ctggccgcct cactggaaac tgggctgggg ggaccggctc ggaggggccg  36360
cctgcggagc ttatgtaacc gctcctccct cggcaggggc aggacaggac gccagaccca  36420
gggaggcccc atgcccctg ccaggccccg tcctctcctg gaggagctgg ttcccctccg  36480
cccagcaaga ggacccccag gcccgtccct cccgagagca ggcccagggt gaggaaatgg  36540
gctgcagtgt gggcgctgga gaggacaggg gacaggcggc agtgccaccc ccactgcggc  36600
cccttcctcg ctgggccagc cgagccatga cctcatctgt ttccctctgc gctgtgctcc  36660
tttctattta aggagagtga ggcggcttcc agggccggaa atgatcctgt ttaaattaac  36720
gggctgcagt ttgggacggt gctcatttga aaaaaaacag tgcagccccg ggctgggcag  36780
atggctgctg gctccgccta ccacttccat ggggagggcc agggaggccg gccacaaccc  36840
tggccccacg aggggtgggg gtggcagcct ctgatacagg acgaggctgc caggccccaa  36900
gcaacagagc cctgcacgag ggtctctggg tcccagacac ggggtgtgag actagctggg  36960
gagccccagg ctcagcggca ttctgtcctt acagatccct cccacggctg aactgtcccc  37020
aggatgagat gccgggggtg acatgggcag cctcaggtcc tcccgggacc cacaggcagg  37080
cacagggatg gagactccgg cctcggaggc tgaacgaggg agatgagaaa ggggagtctg  37140
cgatgtcctt gcctacacag atggaaaaac acagccagct caaaaagggc cgtctggaga  37200
cgagcccacc tgtggggtgt aggaaggaga gcgcttcata cgtatgctac ctgccgctgg  37260
ggtcggggcc acccttccag ttcaagggga gaatgagggc cggctcctgg tgcccctgca  37320
cgcagctgac atggagccag gcgttgtgac cccettgcat ccctctccac tcccaccctt  37380
cacagcctgt gtgggcaggt gctgcactga ccttacgctc ctgatgggca cactgaggct  37440
caaggggccc tcctcctccc ccaacaccat cccccaaaca cctccccggg cagccagcag  37500
ggtccagtgt gtcaatggag gaagccaagg taggaagagg atggtggggg ggggggcaag  37560
caaactggcc atctgcgccc ggctgtgcgg gcacagcagt gccctggaga gggcagcagc  37620
acagatccag cggggcagcc ggaatcccat cacccactcg gctgtgggca cagccaatga  37680
tggtacgagc catcctgagg ccagggccac gatgcacagt ggacgggctc agaacccgga  37740
gcccctgtac tcccacagct gtgacgttcc ctgggcatgg gcttgcccca gcgctggcct  37800
cattcctgcc tcaaccagaa ggaagagctg gcttccgcct ctgcctgggc acaaagccct  37860
ttctgaggtg gcctcacaga agccagcctg tcttcagatc atggcgctgc taaggtcagg  37920
aatgccaggc tgggccaggg ctgggcctcg ggagctgcag ggagaaaagg acccagcccg  37980
cctcagcccc agatgtagcc cttctcctgc caccagtgcc tgggcaccct ggcccctagg  38040
```

caaggacagc tgccaagcca tgaagagcga ggtgttctgg gaaagggcgt gagctgcatt 38100
ttccagctgc gctcactctg cagggagact gtggcgcccc cgctgctgtg cccgcagacg 38160
tgcccggcct cagccagctg gagcgcaggc agcagagtgc aggccaggcc cagacagcag 38220
cgggatgttt tcattccagg gtgcttggcg ggctgggctg ccgtggccac tgcagagctc 38280
cagaaaagaa catgtgtgtc tccctccaaa gtatattcct tgctggaaag cagatcccag 38340
gcagggtctc ccccacgagc agggggagag gcaccccaag gtgggggagc gagggcagtg 38400
gcagaaccac cccataccct aggggaccca gggaggggct tgcagatgcg ggacccacat 38460
ttggcagcgg tgcccggcca ctgtcaccag atggtggcca gcgcatcacc cactcatggg 38520
ccaggatggc agaggagatc cacagagacg gctccagcag gaggccctca tagagatgcc 38580
ctggcctcag aagagccaac agaaagccgg gaagggggac gtcgaggctc aggcttggca 38640
caacctcccc aaagctccca aagactctcg gtgcccacca gcgacagcgc acaccgccac 38700
cacctaacag caagaatgca gcggggtccg cacatcaggg cgggcactga gcggaactca 38760
ggcagtgcca ctcgccagct tacgtcaaaa gaacaaaagg agtgaggacg gtactcgcgg 38820
ctctgccaac acttcccagc cccgcacgtc tcacacacac cagaacgcgt caaaaggcac 38880
caatgggcaa acacccagat gtaggcacaa gcaggagtgg gccgggtctt gtgagccccc 38940
acagccacgc ggccctgcgc tgaaggcacc gaggctgggt gctgaggggt ccataggagt 39000
ccacccgccc aggctgcact ggctcccgtc gtccagtgtc tggtctaagc acaggcacag 39060
tgtctggctc tcaccctcag gctgttacac tctgctctgt ggcagggcag gtctcacagt 39120
gcatggagga caggggaatg ggcccccgga acccctgagg gaaccgacag agctacttta 39180
acaaggtatg attgttgggg ctgccagtgg ctgagccagg tcactgctac actgccctgc 39240
agggtgcatc taatcatgga gcccacttta caggtgagga aactgaggct gagagactgg 39300
accaaggtca caccagaggt ggaggcgctg ggacgtgaac ccaggtctga ctccagggcg 39360
caaattccct acatctgggt tcccagcctc cttcctgaaa ctgaacagga aactagagag 39420
aagggacaca gcagggatga gccagggagg gagaggtggg aggggctggc agggagggag 39480
aggtgggagg ggctggcagg gagggagagg tgggaggggc tggcagggag ggagaggtgg 39540
gaggggctgg cagggaggga gaggtgggag gggctggcag ggagggagag gtgggagggg 39600
ctggcaggga gggagaggtg ggaggggctg gagggaggga gaggtgggag gggctggcag 39660
ggagggagag gtgggagggg ctggcaggga gggagaggtg ggaggggctg gcagggaggg 39720
agaggtggga ggggctggca gggagggaga ggtgggaggg gctggcaggg agggagaggt 39780
gggaggggct ggcagggagg gagaggtggg aggggctggc agggagggag aggtgggagg 39840
ggctggcagg gagggagagg tgggaggggc tggcagggag ggagaggtgg gaggggctgg 39900
cagcacccaa gcagctgcac ctgggcgcag ggcccctcag cccctcgggg agtgcaagca 39960
catcgcagcc cgactcggaa gcgccactgc cacctctgtc tgtctataaa ccagggcact 40020
agtgtgggcc ccaggcaccc tgtgcggctg caggggtctg ccccagagca tgctgatgaa 40080
atcatcacca cggcttctca aagagcctca atttcctggt gtgtaaaatg agaccaggag 40140
tggctgcaac cctgcggtgc cgtgatgagg tatggagaga caagaacaca gagggctcag 40200
cgcggagccc ggcgtggcca ccgcggggag agggtgcgga ctcttcctag accttttctt 40260
tttgagacag agtttcactc tgtctcccag gctggagtgc aatggtgcaa tcttgcctca 40320
ctgcgacctc tgcctcccag gttcaagcga ttctcctgcc tcagccccca aagtagctga 40380
gactacaggc atgcgccacc acgctcagca tttttttttt ttgagacaga gtctcgctct 40440

-continued

```
gttgaccagg ctagagtgca gtggtgtgat attggctcac tgcaacctcc gcctcccggg  40500
ttcaagtgat tctcctgcct cagcctccta attagctggg attacaggcg cccacgacca  40560
cacctcgcta atttttgtat ttttagtaga acggggtttc accatgttgg tcaggctggt  40620
cacaaactcc tgaccttgtg atccccccac cttggcctcc caaagtgctg agattacagg  40680
cgtgaaccac cgcgcccacc ctgttttttt tttttttttt taaagaccgt ttcctagtcg  40740
cccaggctgg agtgcagtgg caccatcaca gctaactgca gtctcaacct catagactca  40800
gggaatcctc ccccctcagc ctcccaacta gctgggacta caggcgccac cactaatatc  40860
tatttattgg tctcgctatg ttgcccaggc tggcctcaaa ctcctggcct caagccatct  40920
gctctcctaa agtgctggga ttacaggcgt gaggcaccgc gcccggctgg acagtggttt  40980
tgatttacgt ttccctcatg actaatgagg ccgaccatct tctcacacgc tgttggccat  41040
ctgtgcgtct tctttggaga aatctctgtt cagatcctgt gatttttttt tttttttttt  41100
tttttttttg agacagggtc ttgctctgtg acccagcctg gagtgcagtg gtgtgatcac  41160
agctcactgc agccttgacc tcctcggctc aagtgatgtc ccacctcagt ctcctgaata  41220
gctgggacca cagatgcata ccaccacgcc cggccaatgt tcttttattt tttagagacc  41280
ggggtctcac cctgttgccc aggctggtgt caaactcctg ggctcaagcg atccacccac  41340
cctggcctcc caaactgctg ggattccagg cgtgagtgac cccttgtcca tgtttaaacg  41400
gggtccctgt ctgttgttga atcatagtgt tccctgtatg atctggatgc aagccgatac  41460
tgcatggatg acctgcaggt gctctctgtc tccacagtcg cctctgcagt gggagctcgg  41520
gtgccccaca ttcccaactg ctgcagacac aaccaaagcc tccccatccc ttcccccacc  41580
cctgccggca atcgcgtaca ggagtgagcg tgtgacttct tgtccacatt tttgtccaca  41640
agtttggcga gtttgcatcc gcgtctaata aagaaactac cgtttctcac gcaggcacgt  41700
tctgaacgcc cgagtgcggg agccacgtaa gacccggctc agggaccccg ggtgaggcca  41760
gctggacatg caggatgcag gtcctcacca ctgcctccgc tcggctgcca gggctcttcc  41820
tagaagacac aggcctctcc taggctctcc tgacagaggc cctacccctg cccccgagtc  41880
accttgcccc ttggggactc tctctgggca gctccctgtg ggagctttga aacctggctt  41940
caatgtcacc tgcactgggg gtccttccag gccagccccc tccccatcat ccatctctgt  42000
ccttggagaa tcatctgcgt gttggttgaa cgcgggctcc agtgataacg gagccctcga  42060
gggtggccct ccttctgctg agggctcatg gaggccttgg tgacaatccc tagtcctcgc  42120
tctcaggatc cagggaccag aaatgggagc caggggcccc tccgtggcct ggccagcccc  42180
ccaaggaagc tgtgtctctg gcagttgcgc tctaaggcat caggcctagg ggtcgctcca  42240
gaatgcctgt cttccccgac gccaatccca ggcaggggcc ccggggtctg cgcctgctgt  42300
ccctacactc tcccacactc tcctgtcatt cagggatgca ggtgggaaag ggcaaggccc  42360
cgggtgctcc tatattttac atcagtgaac caagcaccta ccaagtccct cgatgtgccc  42420
agtcctggac cccagcattt gcgagacagc agcagaccca ggtgaccccc agccagggtg  42480
agtggcaacc agcaccagaa gtggccttta gagcaggggg ccctgagctg atgacatcta  42540
cacctaggcc agtgccagcc aggacaacct ctgggacaat gggatgtcgg ctccaacgac  42600
caatttacaa gaaacacaaa gcacacactc acagcaccac ggaggtgaca ccatggaggt  42660
ggcacccccca agacacagcg agaaatccag gctgcaggag ccagtttctt caacaaattg  42720
cacaaggaaa aagagaggaa gggaagctcc tagacatcat cggacattta aaagacaggc  42780
```

ggtggctcaa gcctgtaatc ccagcacttt gggaggctga ggcgggagga tcacgaggtc 42840
aggagatcca gaccatcctg gctaacacgg tgaaaccccg tctctactaa aaatacaaaa 42900
aattagctgg gcatggtggc gggcaccagt ccaggctact caggaggctg aggcaggaga 42960
atggcgtgaa cccaggaggc ggagcttgca gtgagctgag atggcactgc tgcactccag 43020
cctgggcaac agagtgagac tccatctcaa ataataaaaa taaataaata aataaataaa 43080
taaaatacat cactcacacc tgtaatccca gcactttggg aggccgaggc aagcagatca 43140
cctaaggcca agagttcaag accagcctga ccaacatggt gaaaccccat ctctactaaa 43200
aatattttta aaaattagcc gggcgtggtg gcgcgcgcct ctaatcccag ctactcagga 43260
ggctgaggca ggagaatcgc ttgaacccgg gagatggagg ctgcagtgag ccgagatcac 43320
accattgtcc tccagcctgg gtgacagagc cagactccgt ctcaaacaaa acaaaacaaa 43380
agacatcagc tagctggtcc aagcacagtg gtgttcacaa cgaattgatc acagccaggt 43440
agaattcttc attctttctc cagtcctact gctttgcttg accagcctta aagacacaca 43500
tatatttttg tctgggcgcg ttggctcaca cctgtaatcc caacactttg ggaggccaag 43560
gcaggcggat cacctgaggt caggagtttg agaccagcct gaccaacgtg gagaaacccc 43620
gtctctccta aaaatacaaa attagccagg catggtggca catgcctgta atcccagcta 43680
ctggagaggc tgaggcagga gaatcacttg aacccgggag gcggaggttg ccgtgaggtg 43740
agatcgcgcc actgcactcc agcctgggca acaagagcga aactccgtct caaaaaaaaa 43800
aaaaaagtat atatttttaa aagacattgg ccgggtgcgg tggctcacgc ctgtaatccc 43860
agcactttgg gaggccgagg tgggcagatc acgaggtcag gagatcgaga ccatcctggc 43920
caacacagta aaaccccgtc tctactaaaa atacaaaaat tagctgggca cggtggtgca 43980
tgcctgtaaa cccagctacc aggtactcgg gaggctgagg caggagaatc gcttgaacca 44040
gggagtcgga ggttgcggtg agctgagatc atgccactgc actgcggcct ggagacaaga 44100
gcaagactcc gtctcaaaaa aaaaaaaaaa aagaaaaaaa aaaagacatc aactaattgc 44160
agtgtgtgga ccttatttgg ctcttaattc aaactattaa accaaaaatg tgaacacacc 44220
aggccttcgg tggcatgaag gaactgtctg ttgtgttagg tgggtctgca gtattgcgat 44280
gccctccaaa atgcttgcag ataaaagggt ggctggaatt tggttcaaaa catgggtcag 44340
ggctgggcgt ggtggctcat gcctgtaatc ccagcacttt gggaggccga ggcgggcgga 44400
tcatctgagg tcaggagttc aagaccagcc tgaccaatat ggagaaaccc tgtctctact 44460
aaaaatacaa aattagccag gcatggtggt gcacgcctgt aatcccagct actcgggagg 44520
ctgaggcagg aaaaagcgct tgaacccagg aggcggaggt tgccatgagc cgagatcgtg 44580
ccattgcact ccagccttgg caacaagagt gaactctgtc tcaaaaaaaa aaaaaaaaaa 44640
aaaaaacaca tgggtcagga gggagaaggg tcggggcagg gagggcaggg caggctctgg 44700
ggtggggggt ctgtgagtca gccacggctc tgcccacgtc tccccacgaa gcttcgagcc 44760
acgcagagca gcacgttttg cagtacgcca tcttttccaa aagccaccac ctctcggcag 44820
catcattaac ccaaggcagg ctgtggcctc agaagccccg gctgtcctcc acctggaact 44880
ggacacagct gtccctgctg agcttcagca gccagggagc cacaagtgga gaggcacctg 44940
cgtgagcccc ccaggaaggc tactggtgac acccagacag caacgctctt ggacccttga 45000
acacctgcca gcagctgtga tctgtgtcct tcacctctcc cagcttgacc cctcttccct 45060
ggggaaaacc cagccgtctc cccgaggagg agtttgcagg gtagacagca aaatggctgg 45120
gctgccccac agcacagagg gtggcctggg gggccagcca gggccttcac atccttccta 45180
aggccctagt ttgccatggg tcccctcacc ccaccttcca gaactctccc agcggcggcc 45240
ccaggtgtgt acagaacagc acccacctgc ccacatgagg tcaccctgtg ccctgttgca 45300
cacttggggg gcctggcatt cggaatcttg ccagctcagg ctgggacagg ccaccaactc 45360
ccagggtccc cctcctccaa accccaggac cagagcctaa gaggacaaca caaggcaggg 45420
gcgggggctc cactgctgtg ccaagggcct ggagaacacg ggccttgctc tccgctcagc 45480
agccaccagc gcccttctct cccggacagc tcctgagggg ctgctctcat ggacaccatc 45540
aggtgctggg aagcaggaac caccaggccc tggacagagt ccccagtgac cggcctggca 45600
gacagaggag ccctcagcta cagcatcaca aacaacgggt ggggtaggtc tgatgcaatt 45660
ctgtgggtgc tgttgccagg caggaggagg ccatctccac agagacagcc gcgagacaca 45720
cgcgtccgca gtcagggagc gcaggagcaa tgtggccccg aggggcacgg gctccattgg 45780
tccaggagaa cccattcttc tcccaccctc gagaccaccc agcaaagccc caaggacaca 45840
cggctcccct aaggaagggt ggccacaggc gggagtgacc cagaaacgtt acaaaaccaa 45900
atgccagaac ccacccaatg tttagcaagc ctggggatgt gccacgtccc ccagggatcc 45960
agcacgcacc caaggagaca ctgtcccggc gaggagcctg gagcctggga aatacaaggc 46020
atcagactgg tcccaagact ctccccagcg ctggggacaa ctgtctgctt atcttagtcc 46080
cctccgccct tttcaatcca accctgggtc ctgggcacct catagttcca aacccctgct 46140
atgcacatcc cggctgtgat gcctgggaca ggtcgtgtca cctctccaaa cctgtttcct 46200
catctgtgaa atgcaaatct ccacggtccc tatgcctcgg atggtcagag tcaggattcc 46260
gcatgacgac cccccaacagg agcctggcac agacctggct ctgggcagcg tctccataaa 46320
ggccacctgt tgtttttatc tcccgaaagc gaacatgaca aggctttaac cccccacggc 46380
aatccccccct cacccctgtt ctcaggatag ccttggaacc caatagcaga gcgcctgagg 46440
cccttcatga ccccagccca cccgcgagcc cacctcccac cctgccccta cccctcacac 46500
ctcccgtggc cagcctccag cctcacggtc tttgctcaca ccgttcaccc cccttcttct 46560
ggacccacct catcgcccct tcctaagcat cagcccaatt cttgcacatc catcaaatcc 46620
ttttccagac acctcctgga actcttccct gccgccccct acagccatcc ccacctctcc 46680
gggtaccccg cagccccagg ccgcatccca attcctctcc aattagcgac tgtttgtcct 46740
cccagctgag cgcggcctcc gcgccccgcc cccgctggcg tctgcagagc ccccgggtgg 46800
gacgtctgtc tccagacccg gggtttttcg gctccccggg gccgtgccaa ccgcggctcc 46860
aggcgttcct tatttagcag ggccgccgtg ccgcgccgga gcctcgccct gggagcgtcc 46920
tggcccgcgt cctgcttccc gtcccgggcc agggaacgcg cccacgcccg cccgtcccgc 46980
ggcctctccc gggtgccgct gggcccgcta ctcacagcgc tgtggcgtcc gcggggatgc 47040
gcagcgcggg accgagcgtc cgcagcccgc ggcccgagca gttgacgcgg caggcggcgc 47100
cgggcgctgg gccgcagagg caggggggct cgcagggccc gcagccgcgc ccggggcccc 47160
ccgccagcgc cccgagccac aggcccaggc ccagggccag cgccaggcgg gcgggcgcgg 47220
cgggcggcat cgttagggca gcgcgcgcat ggccccgccg tccccaggcc cgcccgcgcg 47280
cggaggccgc agctcaggcg gggcccgcgg acggcatggc gggcgcgggg ctggatgggg 47340
ctgcggccgc gacctgctgc tgagcgacgc ccgctcgggg ctcggggcca ggccgctccg 47400
ggagctcggc cgcccgctcg gacgctggcg ctgcagtgcg ggccccgccg cggctcctcc 47460
tcctcctccc cgcgcggcgc ggggcggacg gggcgagggg gggcggggcg ggtgcaggct 47520 ccgcccccttt cgccacagcg cgaccgggcc agcgatgagg gactggcatc cggaggcttc 47580
accctccgct ccacagggtc ggcagcaggg cggggcctcc ggaagctccg ccccacgcgt 47640
tcccggggcg catgcgacgt ggggcggagc gtctggaagc tccgcccgtc gcactgcaga 47700
gtcggccgag gcgcacgagc tatttttcac gctccgcccc gctgcaggct aaagtgcgtg 47760
ggcgggaagc ggtgggcagg gtgccatctg gctccgccct tctcctgtgg tgtgggccag 47820
gcggcgggtt cctcctcctg cagcagccac aggctccacc ctgatccttc ttccgcggtg 47880
tggatccttc tcccgcaatc tccgtgcgcg gcccgagtca gtacccgcag cctcccgacg 47940
cacccgctgg ctccaagcct ccctacccca ggtttcctgg ctgagagaga gacagaggga 48000
gagaggggga agagagagaa caggcaatgg gaggttgatg gtgagagctt attgaaagac 48060
aagagggagg aaacccacat ccttcattcc ccatccattc atttattgcc ttatttattc 48120
cattgaatct tcacagctct agaaaaagtg tgctacaatt attcccttta ttaaatgagg 48180
tcactgaggc acagacagtt taagaaattt gccagcaggg cacagtggct cactccggta 48240
atcccagaac tttgagaggg ggaggaaggt ggatcccttg agtccaggag ttggagacca 48300
gcctggccaa catggcgaga ccccgtttct acaaaaatta gccaaaatta gccaaactgg 48360
ctcacgcttg tagtcccagg tactcgagag gctgaggccg gaggagcgtg tgagcccagt 48420
aggcagtggc tgcgctgagc cgtgattgtg ccactgcact cccgcctggg caaaagagta 48480
agatcctgtc tcgaaaaaaa aaaaaatgga aaaaagaaaa aaagaactgg ctgggagtgg 48540
tggctcatgc ctgtaatccc agcactttgg gaggccgagg cgggcagatc acaagatcag 48600
aagttcgaga ccagcctagc caacatggtg aaacctcatc tctactaaaa atacaaaaat 48660
cagctgggca tggtggcagg cacctataat cccagctact agggagcctg aggcaataga 48720
atcgcttgaa cctgggaggc agaggttgtg ccactgcact ccagcctggg caacagagca 48780
agactccgtc tcaaaaaaaa aaaaagaaat ttaccaggtc acacagcagg tggatggtaa 48840
ggctgcgatt gtattccaaa cccagctttt aattgcagtc aaatgacaga cttaagattc 48900
aaggactcca gtggagggaa gaaacagcca caagaaactg ctgc 48944

<210> SEQ ID NO 38
<211> LENGTH: 68818
<212> TYPE: DNA
<213> ORGANISM: Homo sapiens

<400> SEQUENCE: 38
aagtggctgg tggataactg ggacccaaga gttatctcag cgtcgggcag gcatcgacag 60
ctccaggagc cctttccctg caggcgggct ggcgggtgag cgattccctc ccttcccagg 120
ccttcccggg aatggaacgt gggcgcccgc gcccgggctc cggttccact tggaacgcgg 180
actcgggagc cgccgggcga gcgcgcagac cgcgggggcg gctccctcgc acctccccgc 240
tcagcgcgcc gcggcggatg ggcgaggcgg ggcgaggcca gagggaggcg ggccaaaggg 300
gcgggcgaga ggacgcggga ccgcggggag gtcgggggcg gggagcaggc ggcggcgggc 360
gccgggaaga aaggaacatg gctcctgagg cgcacagcgc cgagcgcggc gccgcgcacc 420
cgcgcgccgg acgccagtga ccgcgatggt gaactccagt cgcgtgcagc ctcagcagcc 480
cggggacgcc aagcggccgc ccgcgccccg cgcgccggac ccgggccggc tgatggctgg 540
ctgcgcggcc gtgggcgcca gcctcgccgc cccgggcggc ctctgcgagc agcggggcct 600
ggagatcgag atgcagcgca tccggcaggc ggccgcgcgg gaccccccgg ccggagccgc 660
ggcctcccct tctcctccgc tctcgtcgtg ctcccggcag gcgtggagcc gcgataaccc 720

-continued

```
cggcttcgag gccgaggagg aggaggagga ggtggaaggg gaagaaggcg gaatggtggt    780
ggagatggac gtagagtggc gcccgggcag ccggaggtcg gccgcctcct cggccgtgag    840
ctccgtgggc gcgcggagcc gggggcttgg gggctaccac ggcgcgggcc acccgagcgg    900
gaggcggcgc cggcgagagg accagggccc gccgtgcccc agcccagtcg gcggcgggga    960
cccgctgcat cgccacctcc ccctggaagg gcagccgccc cgagtggcct gggcggagag   1020
gctggttcgc gggctgcgag gtaagagcgc gcgacccgca gcggcagatg cacgaaccag   1080
aacggccggc gccggccggg gccatcgccc gctgcggcag ctccccgggc tccatctcgc   1140
atcccctctg cgttccgcct cccttggaag cgcattcccc acctccgcta gtgctgccct   1200
atttccggta cccagcgcgg aattccactg ctcttttgtt ggtgcatatt tattggatac   1260
ctccttcttc aggatatgtc accatagtct tttttactga aaattagtga aagcctaatt   1320
agagtgaaag agtacatctg ggttttgttt tttttttttct tgtagaggaa aaaatgaaca   1380
ttacttgtgt aactgatggt agttgcaact gcatatttgc caatgtcaca aaatctaaag   1440
gaaaatgtta tagtcacccg tggtttcctt cttgcctgga cactccattg tcccgggctg   1500
aaaagggtag cagtacagtg catataatgt caagttgtgg gaggagtgtg gcagattgtc   1560
attggtgcat ttttttggtg atgtgtgtgg ttgttttgag gagtgggagc tgttaagaac   1620
accacaaata gaataaaata atatcgtgaa gttatttggc cgtttctaat tctagacatt   1680
tttctaaaaa cagttgcaaa ggaaagatta cattgtttta aaaaaatttg aagtatgttt   1740
ttaaataact aaattaatgt tctttgaaat tccaccaaaa tgatgaagtc accagatagc   1800
agctgataaa tgtgtctgag cccagtgcgc ccagctctac aaaaggcaga agaggaattt   1860
tcaaatttgc cagtgcccag taagaggaca tgaattttct agtaccagag gaaattctct   1920
ttttacaaat tttgtcagag gtatccttgg gaaagtattt catttgcttt taccctccaa   1980
attattttaa tctatatttt taagagtttc cattctcagt tgagtttttc ttgttcttct   2040
ccttctgtca gttttgaaag tcttgcacaa aaacaatcca ggtgttgtta cagcagtgtg   2100
attaaaacca ggtcaggcct acactgaaat cccagttcca ccactcatta gctgtacgac   2160
cttgagcaag ttacttatcc tctctgatac ccaatttttg gatttttttt tttttaaag    2220
agatgatcat aacgcttagg acttgactct ttgggagaat taagtgagtt aagacataaa   2280
atgtgcagca tgtatttgtc atgttattag cgcttcagaa atataaatgt aaacattttg   2340
gtacttcgtt tatggagatt cttatactag ttaattttat taaaagcatg atggggaaca   2400
gaagatcctt ttcggataac ctgtgtgagt aaattaataa aacactaaca ctttttaaga   2460
ttcaaaactg gattaattat gttattttac accatttaaa atgtgcattt aaaaaatatt   2520
cactgaagtg agagagaagt tcctttttaag ttaataaata atggtaagtt gcatgatcct   2580
tttaactcag tttaagcatt tgataacacc cctaaccttg tttgaataaa ctcaataaca   2640
gaatatagag aaataaaata tatatttcat atgagtatgt atgtaaattt atttctttta   2700
aaggaaaatt tcaggaaaca aaatgaataa gctcatagtc ataaaacctc tagccaaagt   2760
gtgtcaatgg tctgatttgt aggagagcag actcaggaat cgggaatttt tttttttttt   2820
ttaagagtcg gggtttcact ctgtcactga ggctggagtg cggggaagca aacgtagctc   2880
actgcggcct caaactcctg ggctcaagct gccctcccac ctcagcttcc caagtagttg   2940
ggattacagg tgcaagctgc tgctcctagc tgaaaagttt taattatata aaatgtttaa   3000
ataaattgtt attcctttct tttatgaaga aatataattg atattcttgt cacttattaa   3060
```

-continued

```
ataagcaaca ttttaaaatg tttagcacct actgtgaaga tagcactgtg ctagctgcta   3120
tgaataaact agaatagcat atcactgttt tcctatggac aaaaacccag aaatgtaaaa   3180
taaatagcca tgaatgggtt gagattcccc ctgccccctt tggatactga tgacagaaat   3240
cttatatgca ctatgtaagc agtgccctag gatcagaaca gaaagtaact tgcaattttt   3300
aaaggtggga gaaatgactg aagtttggag tggtcaggag tttccctgga agtctcttgc   3360
ctttgtgact ttgtatagct ccctcaaact acctgagcct gagctcctca tttataaaat   3420
ggaagaattg aacctagctt ccaaggtcct ttctagcttc accatgctct ggtctgttgt   3480
ttaatgacat gaatccaaga tggacaacaa atggtcgatt ttgctccttc tacagtaaat   3540
agatctatct tcttagcaga agtaaaatag taaagaaaga agacatgttt gaggcctgtt   3600
gaggcctgtt tgctgtatgc attgtatcta atcaaggaat tgagaatgta gccctaaata   3660
ttaggaagga gttgaaagtt tctgagcagg aacagaacat gctgaaagga aattgtgtca   3720
gcagcatggt gtacaggaga gcttggcaga gagaaaggag gcaagaagac ctgtgggagg   3780
cagccagtaa ggaggtgaag agggcctgga ccaaaggaag ccaaggatga ccgaaagatt   3840
taaagatgaa gcccagattt aaaagtatcc tcaagtattt gtttattctt ttcttagcaa   3900
attcttttta gtacaaagat aaaatatggc actctgagtc ataaaatttt ctgaatttca   3960
gaagttgaat gtttttctga atgtatcaac ctgttaaagt cagttcctgt ttgttatttt   4020
aggcgtatat tcttgggctt tttttttttt ttcctagaga aactatgaag tactagctgt   4080
gcaagtcagg gtgggctaag ctgctaaaac agatacctcc ctccccttca ataccctgaa   4140
gaacaagaag ttaatttttt gctcgtgtaa cattttagag agggtattcc aggttgaata   4200
cctggaataa tgaatgaaat aataagtcga ctcttatttc tcctaaaata attggatctt   4260
gacattgaaa ttggtgtgct gattgtattt aataagtgac ctccaatgca gttatttcat   4320
tttgccatac tttatgtaat ttttattttt tctgccttcc ctttcgatgt ctaaagggaa   4380
gcataattag ttattggaaa ggttattgag acttaaaaaa agatttgaac atggctttgg   4440
ttgatgctac cacacagaaa ctgcaaacat ccaactcacc gctcttagtt gctgttcatg   4500
atagtctatg cacagtgact gatgaattta gcctgtcttg aggcttcaga acttagtctt   4560
atgtcatcac gagcagagct ttatcctaaa ttacaggttt tcaatggggg gggggggggag   4620
gggcagtttt gcccctcagg ggacatttgg caatctctgg agacattttt gattgtcata   4680
cctgggggga tgcccctggc atctcctggg ttgaggttaa ggatgctgct aatctacaat   4740
gcacagtaca gccaccccac acacacacac tacaaagcat tctcccaccc aaattgccag   4800
gagtgaggac tttgagaaac cctgccctag actgttaaat tcaaaaggaa ataatggttt   4860
attgctcaca gtgtgccagg cactgtgtta aactccttat attcatagtt ttgtttttat   4920
cctcacaaca acctgtgaag aaagaactct catccgtcac cactttactg ttgagggcac   4980
taagccttct aaaggttaaa tgacttgccc agggccgcaa ctattagatg ttgcagtcag   5040
gatttaattc caggcacttt gtgttcaaag tgtttctcat ccactgtgct atatgccagt   5100
agtgcccaaa cctaacttta gccagcaatt gtctgcatct cttcagttta tgaacattta   5160
tttattagga catgcaggat aatcatacca acacagtccg tgtatccaga attctaattg   5220
atctagggag tgggagagcc tgcctctcta ttttttttaa attggtgtga aatatacata   5280
acataaaatt ggccatttta accattttaa gtatataatt gagtgacatt aggtagattt   5340
attatattat gtaaatggac ttaacacaat ttatttccag aactttttta tcatcccaaa   5400
cagaaactct gtactcatta aacagtaact ccctgtttcc ccactccccc ttgccccaga   5460
```

-continued

```
cgctagtaac ctccattcta cttccccttt ctgtgagtct ccctgttgta gctacctgat   5520
gtaagtgaaa tcagaccatg tttgatcttt tgtgtctggc ttattcactt agcatagtat   5580
tttcaaggtt tatccatgcg tgcaaattcc cttctttttt atgacgaaat actatttaat   5640
tgtgtgtgta catgtgcaca cacaatgaaa tactatttca tcataaaaag gaagtttgta   5700
cacatatata cacacacacc aaattttgtt tatccattca tcagttcatg ggcatttgcg   5760
gtttttttcc acctttcgac tgttgtgact ttccgtttat ttttaatctg aactttactc   5820
catcacttcc tccctttcct tttttattcg caccataatt ttgaacaagc agactttgta   5880
ttttcattac tctggggatt tttttgaggg aggcttgcta ccctttgggg ttgtggtaag   5940
gttgtgccag taacagaatt catgcagtaa aaaacattca tgggactttc ttttgtgata   6000
ggtactaggg atgcagagat gaataataca aggtctcgac cttcaaggag ctcagggttt   6060
agtagggaaa acagaggtat aagtaagtca ttgcaatgcc aggtcccaga tatgggagga   6120
ttccagcaaa gagaggataa ggccaggcac agccgctcat gcctatagtc ccaacacttt   6180
gggaagctga gatgggagga tcacttaagc ccagcagttc aaggctaccc tgggcaacat   6240
agtgagtggc aaaaaataca aaaattagcc aggcagggtg gcacatgcct gtggtcccag   6300
ttatttggga gtttgaggtg ggagaatcac ctgagcctgg gagattgagg ctgcagtgag   6360
ctgtgatcac gccactgcac tccagcctgg gtgacacagt gagaggtgag agcctgtatc   6420
taaaaaaaaa aaaaagagag gatcagattt acctggagag gtcagagaag gtttccagag   6480
ggagtaaaac ttgagcttca ttttgaagaa tgagagggga atacaaggag ggaaaaataa   6540
taggaacaag acctgttcct gttacagcaa acctgtaact cccaccatgg aatgggcacg   6600
ttttcctgta gacatttgga gccagtgtgg gcttcaagcc tagggggctg atatgatcat   6660
ttgtcaatct gaagatgact cttggaacaa cgtagaggat agggtgaggt gggtaggctg   6720
gtggctgaca gactaggtca ggagagggct gaccaagagg aggaggggtg acgagggctg   6780
gaactaaggc atatgagctg ggatggaaag aagctagata gaaaggaaac aaaaaccatc   6840
agaactgtgg aaccaactcc atgggaggga taagaagagg gcctattcta gggtgaaacc   6900
caaatttctg gcatggtacc attaacccaa acagaaagag gagatttcca gagaaagaaa   6960
agcaaatttt gcgggaggtg agtgtgagct gtctagagaa tatgcaggta gaactacatg   7020
ttaactgtaa catatacttg tctgcacctc aggagatggc tgattaagaa ttcaggattc   7080
aggccaggca cggtggcaca cgcctttaat cccagctgct taagagactg gggcgggagg   7140
attgcttgag cctgggaatc cgagatcagc ctgggcaaca tagcaagaca ctgtctctaa   7200
aaaaaaaaaa aaattcaaga ttctggagtc aatattactt aaggtagcaa ctgtctattc   7260
tatagaaaat ggacaaatat agataaaaag ccacttccct ttctaaaagt gtccctgcaa   7320
ttcaagtgaa tactaggaag gattgtgttc attcttctaa acaagactca catgtatctt   7380
agcacaaaaa gaggattctt ttatgataca aatgcactga gaatttggtc aggctatcac   7440
aatgaactga tagttcagat ggatttgagt ctttatacca ctctggaatc tggaccaact   7500
gggcctccta aggccatttt gcagatctgg gcttgtttct gaagctacag acaggcctct   7560
tccaagcact ctaagtgctc cacaaataat atttctgttt cccagaacaa ccccacaaaa   7620
aggtactctt actccatttt tagatgagga agtggaggct catgatgtca ggtaagcttt   7680
ctcagctccc aagtggttaa gccctcagtt taatgtcatt tgactccaga gccctatgtt   7740
gcaccatgcc ttgataatag gccatatggg tttcatgtat ttcagatggg gaaggttagt   7800
```

-continued

```
gtgaggtgaa agatacacaa ttaacctttt aaccatggaa ctgaaatatt tacagatgaa   7860
gtgatacaat agctggaatt aattccaaaa taattggggt ggtactggtc catggcctgt   7920
taggaactgg gccgcagagc aggaggtgag cagcaggcta gtgagcattg ctacccccta   7980
tcatatcagc agtggcatca gatgggtgag gatgtaaatg aactaggatt ggcattgagt   8040
tgatattgtt ggatctaggt gatagattta tcattataat attctctctt tgtgatattt   8100
ctgatatttt ctaaaataaa aagttgtagt tatttattta tttagacgga gtttcactct   8160
tttgcccagg ttggagtgca gtggtgtgat ctcggctcac tgtagcctcc gcctcccggg   8220
ttcaagcgat tctcctgcct cagcctcccg agtagctggg actacagcct cccgagtagc   8280
tcaccaccac acccagctaa cttttgtatt tttagtagag aggaggtttc accatgttag   8340
ataggctggt ctcaaactcc tgacctcagg tgatccaccc acctcggcct cccagagtgc   8400
tgggattaca ggcgtgagcc agtgtgccca gccaataaaa agtttttgaa aggatttaga   8460
taaaatagtt ggggaaatgg catttttgtt caaagccaat tatttatgtt tggaatatct   8520
tttgtgcttg gagttctcca ttacagagtt ccccagtgtt cctattaata agtaacattg   8580
agcagaggaa tgcactgttt agatcagcag tccccaacct ttttggcacc agggaccggc   8640
ttcatggaag acaatttttc cacagacctg ggtaggaaag tgtttgggga tgaaactgtt   8700
ccacctcaga tcatcaggca ttagtgagat tctcataagg agcaggcaat ctagattctt   8760
cacatgcgca gttcacaata gggttctcac tcctgtgaga atctaatgcc acccctgatc   8820
tgacaggagg cggagctcgg gcggtaatgc tcacttgcct gcggctcacc tcctgctgtg   8880
gggcccggtt cctaacaggc catggaccag tacccgtctg cagcctgggg actggggacc   8940
ctgctttaga tgatgtactc tggctttgca ttctggcatt agctaagcac cctcttaaag   9000
gaaattgggt ctatactctc agtccgtgtt ctccctaaca cctggaaaca ttgaatacct   9060
tcaatgctgg gaagttaact cccaccacaa ctagaacagc tatgggaaag acaacagttg   9120
attttgaaga gtgtcaccaa tttgcacatg attccatcct taaccattct tatcctatca   9180
gctctgccaa acatggagaa tagttggctg caggacagct atttttccta cttgtagatg   9240
caactatttc tcacccacca ggatgtaaaa ggtccctgta ccctaagatt ggtcctacat   9300
acacacccaa tgggaaaatg agatgaaaaa tttaaagcag taaatatttg aggaagtaga   9360
tagagtaatt tagaaaaaga aaatacacag ggccaagcac agtggctcac atctgtaatc   9420
ccagcacttt gagaggccaa ggtgagagga ttgcttgagc tcaggagttt gaggccagcc   9480
taggcaatgt agtgagaccc cacctctaca aaaaattaaa aacttagttg ggcttggtag   9540
tatgtacctg tagtttaaga aacttgggag gctgagctga ggcaggagga ttgtttgagc   9600
ccgggtggtc aaggctgcag tgggccatga ttgtgccaga gtactccagc ctgggtgata   9660
gagtgagact ctgtctcaaa caaaaaaaaa aacagagaca gaaaaaaaga aagaaaatat   9720
atggatgtat atcatataaa aatataaata agggaggcca agtgcagtgg catgcctgta   9780
atcccagcac tttgggaggc tgaagcagga ggatcacttg aggccgagaa ttcgagacca   9840
gcctgggcaa cgtattgaga cctcatctct gcaaaaaatc aaaaaatgag gcggaaggat   9900
ggcttgagcc caggagatca agccttcagt gagctgtgat cgtaccacta cactccaggc   9960
tgggtaacag agagagaccc tgcctcaaga taaataaatt catacataca tacatacata  10020
cgtacataca tacatacata agaagacttg tttctttcca tttgcaatgt ttcattcaaa  10080
ggctagaatt aaattgccgt aggccatcac aagtttagct tgaatattat tattttttca  10140
agatggagtc tcactctgtc acccaggctg gagtgcagtg gtgtgatttt ggctcactgc  10200
```

aacctctgtc tcccgggttc aaccgattct tctgcctcag cctcccatgt agctgggatt 10260
acaggcgccc gccaccacac ctggctaagt tttgtatttt tagtagagac agggtttcac 10320
catgttggcc agactggtct tgaactcctg acctcaagtg atctacccgc ctcaccctcc 10380
caaagtgctg ggattatagg cttgagccac tgcacccagc ctagcttgaa gaaaatttga 10440
taggagtttg tttttttcta tttataggcc aagcaatacc acgtataaat attaagaatc 10500
atggctgttc cttagtgcct agttgtttat aaaccatggg aaagaatgaa atcattgacc 10560
aaatgagaca gggtaacagt cttccctggg agtaaagaga ctagcagtct ctattgacat 10620
atattttagg cctggcctcc aaaataaatt tacccaaaga agtgatgtat ttgtgtccag 10680
ggctaccgag cctaatcttt ggctgcctct gtgttattct aagttgtaat tttccatgtc 10740
atctaaattt gtaataattc tttaatatga tagtgtttca gtgaacaaac attctgcttg 10800
ctgcatttct tctgagtgag taattccctg acaactacca gatcttggca gaagcaaagt 10860
tggtcataag ttatgctcca ctctcagtgc tggtgaaacg tatgatgcgt aacacagtgt 10920
ttttgaattc agtgctgatt ttcctaaagg acatttggaa ggaaaaaaga aaaggaaagg 10980
aaataccca attcaggaat agaacttaca tattattata agacttaaaa aatacatgaa 11040
cactaatgat gaactcattt cttcgaagta aaaggcctta tgctattttt tcccatttcc 11100
ctatgtggct tgattgtggc gaaagtggct gtgtgagttt ccattattga aggagttaag 11160
gtctgtggaa tcaaagcatg agacaacatg caaggaccag gttggtttcc atttaacagc 11220
caacctaatc taactgaaag gattgagagg tttgtctttt ttggaaagtg ttaaggttct 11280
tccaagtaac cagcaatgtg actttaccac actgttcatt aacggggctt tggatggcca 11340
ccatgtctgc tgctggctga gtccaaaact gcggtcactc tctccagcaa gctcatggag 11400
ggttacgtca tcttcactca gccagcccaa cgctttttcc atctgctaaa atgtagaaca 11460
tggttgttga ttctactctt tctacaaaga aagagaggga acatggatga gttgctgctt 11520
ttaaagatta tatgttaatt gctgttttaa aaatctgctc agctaagcac gcttagtgta 11580
atcagtcacc atggagtttt ttaataggac agcttctgct cttacagagc agagttttta 11640
tgccagtagg ttagaagcat aacatgtttc tatattgaag tgattctcca acaaggactt 11700
cttttcatca ggggtgacct aaaagttatt acttgaaata taattacatc atgttcttaa 11760
ctgggtttag tagtaggata attacaaggt tgtatccacc tcaaatagga agaactgata 11820
agttttgcac aattatttaa ctcctctgtt aggccttcct tatttcctgt tctcttttta 11880
aaatttgact aagatattgc taatgggctt gggagcctat aaaatgatca gaattgttgc 11940
cttatgtttt gcatgtttgg ggtaacattg gagccagatg tactcttaaa taaaaggtag 12000
gcctacaaaa ccagtttctc agttgcattc aaaatgtgat taaaaaaaaa aaaaggagaa 12060
tctcccttat aggtgaactt tttaatttgt gctttatttt cccttttgcc attcatgaga 12120
tttcttaaat aaaatgatat cttttctttt cttcattatt attttaaagg tctctgggga 12180
acaagactca tggaggaaag cagcactaac cgagagaaat accttaaaag tgttttacgg 12240
gaactggtca catacctcct ttttctcata gtcttgtgca tctgtaagta gaatatttcc 12300
ttgcactaat gggaaagttt tgaaaagatt tgacctatcc aaatcataat taaaaggaag 12360
tgtgtatgca ccagaggggc aactgggaag ttaccttctt acctttgttt ttaattctaa 12420
tatttttatt tgggcatttg tttattgact atcttcctat ggtagaatgc aagctttata 12480
agagaaggga cgtgatttgt tctctgctgt acccccattt cccaaaactg cagatggcaa 12540

```
cagaaggctc tgaaaaatat ataagaaaga atttttctaa ttgtgactaa attgtgacca  12600
aatgctaagt gactgtggac ttgcgtttaa cacaggacgg gagaggcaaa gagttcaatt  12660
ccaatttaga atttggtcaa gttctcttct gcactctggt aaacattaat taaaaatcag  12720
cattatctga ccagccagtt catcgtcagt ggtggtgatt ttcactatga gatacgcgtg  12780
gcaacttgcc agacaccaag aaaccaagtt agaggatttt tgtattagat tccttaacaa  12840
tgaatacagt atcaccatta ttacagtatc atcattattg tcatactatt attatatcag  12900
ttaacataaa gtctgcataa gaattgtttc cagaaaaatg actttccaaa tttaactttc  12960
aggaaataca aataatgcta ctaatattgc ttttattggc gtatacatgt aatatcccct  13020
tcttttggat ttggatatgt tgtgtcattg cctcatttta attcattatt tcttctcaat  13080
ctttaataat tgctggactt ttactccaca agaaacttgc tataggccca tctctttcgt  13140
cttctttcct tctttcagtt cgtcttccca tcctctggta gggggagggg agggatgcct  13200
gagcgagaga ctagctgtag gaaccatttg tctcaaagtc cagaaagcca caggtgatgg  13260
atttgtcctc tgaatcaaag ggcgttcgat gatggatttc tgtcatgtct catctaaagt  13320
cttcacgaga acagatgagg aagcagtttt atgaccccag agcctcctac caaactcctc  13380
tgagaaaagg tttccttttt tttttttttt tttaaattag agacagagtc ttgatctgtt  13440
tcacaggccg gagtgcagtg gcacaatcat agctcactgc agcctcgagc tcctaggctt  13500
cagtgatcct cccacctcag tcacccacgt agctgggact acagctgcac accaccatgc  13560
ccagctaact tttaaaacat ttttgtagag gtggggtctc actttgctgc ctatactggt  13620
ctccagctcc tagcttcaag tgatcctcct gccttggaag ttctgggatt ataggcatga  13680
gccactgcac ccagcctgga tgtgatattt ttatgtttta aattgttaga gtttagaaac  13740
ttgagattga gtttgctgcc tgcattaaaa tgatgcttaa acattaaact gcagtggcct  13800
taaatattaa caagttgatt agaattacta agttcttttc aagctttaca tatacagaca  13860
aatttcttat gcaaaataga aggtaacccc tgtacgtaag tctagaattt cagcagtccc  13920
caaaactgac tgagcattag aatcactctg attttaaaat acatatgtgg ttttccgaga  13980
tctactaaca gagcctccat aatgtagcct agagaaacga gttttcagat gtagtgataa  14040
atttggaagg taagtcagag aagtaagctg aagacagagt tttaggaaat atgcctaaag  14100
tcacataatg aattggtttt cttgtttatt tgagaatatt gtcgcttttt gttctttttc  14160
atgcaaatca cattttattt cttatgtgag tagctatata tttaaaaatt ttgtttttgg  14220
aatattgtag aatctctact taagaaagta tcttagcagt catatggtct gacctcactg  14280
aatgctaaat tctctttaaa acatccgtct cagatggtta ctcatactgc ctctgattga  14340
acaagagtcc caggttaagg gacttacttc tttgaaatcg ttcatttcat ttttctacag  14400
ctatgttaga aagttcgtcc ttagcagtga agccagagtc tatctcttat aacttctacc  14460
cagttgcacc ctccaagcct acctatacca agtatctttt ttccacgttg cttttccaat  14520
tcagctcttc gcaagtttgg agacaaatac ctaatctcct ctaagccttc tccaggttaa  14580
gcctttccag ttcatccagc tgttgattat gtgattggag acacaagttt gagtaactcc  14640
catgatggaa agtccctctg gtgaatgttc tgttcatcag agtccctaag aaagcacatg  14700
agcctcacca tggtgagtgg ggccatgaga ttcctaaacc agacactaca ctgtggcttg  14760
tgcaacctac catggccaga ctcatgaggc tgtttcatca tataaataat tccttagtct  14820
cttcaccaaa aactgtgaag cactgtgtcc cccagctgta tgtgagctag cctgggacca  14880
tagtggagga ctcctctttc aaccctgtta aatttcatct tgttaggatc tgcccatttt  14940
```

tccattctgt tgaaattatc ttggaactgg attcattcat ctcacatcag ctactccccg 15000
aagcctcaca gtatcagcag agttattatc tctatccata tccttgtaaa ttattaaact 15060
aaaaaagatt ggtctaagaa catcagtcca ttaatcaagg ctctttggtt ggagttcact 15120
tcattatatt atcatccagc tcagagtgtt cataaacaag atgataggaa agacttttcc 15180
aaatgcctgt ctgagtaatt cccccattcc tgtgatctgt gagctgttga ccagattaaa 15240
aaggaagtga gaataaccag gcaagattta ctcctagcaa aaccttactg gcttctagtg 15300
actgagtcct ttccctattg cttaccagct atctttttaa ttactagttt taaaatcttg 15360
ccagcaatgt caatatcaaa tgaccaagaa tatcaaactc attactctgt atgtaaatga 15420
gatagtgtac ttacccctat ggcttaagta ttaggctgtt cttgcattgc cctaaatacc 15480
tgagactggg taatttataa aaaaagaggt ttggccaggc actgtggatc aggcctgtaa 15540
tctcagcact ttgtcaggct gaagcaggtg taatggtgag ccaagagttc aaacttagcc 15600
tggacaacaa ggtgaaaccc cctctctgca aaaaatacaa aaattatctg ggcatggtgg 15660
catgcacctg tagtcccagc cacccaggag gctgaggtgg gaaaattgtt tgaagctggg 15720
agtcagtgat tgcagtgagc catgattgca acactgcact ccatccagcc tgggcgacag 15780
agcaagaccc tgtctcaaaa aataaataaa tgaataaata aataaaataa ataaataaat 15840
agaaaagaaa aagaaagaaa agagatttat ttgcctcatg gttctgcagg ctgtaaggga 15900
agcatagctc cagcatctgc ttctggggag gcctcaggaa gctgttactc atggcagaag 15960
gtgaagcagg agcttgcaca tcatgtggca aaagcaggag caagagagag agaatggggc 16020
agggaagaag ccccacactt ttaaatgacc agatcgcatg agaaatcact cgttacctca 16080
aggacagtac caagaggatg gtactaaatt cctgagaaat ccaccccat gatctgatca 16140 cctcgtacca ggccccgcct tcagcattgg ggattatgtt tcaacatgag atttggatgg 16200
ggacaacatc caaactatat caccttgcat agtaggtagg gttttaaaaa gcagtttggc 16260
acagtaagaa aagtacagat ttttttgca tcagacagac ctgagttaaa atcccagctt 16320
cactgctaac atgctaggta aatgtgggca agttaattaa catttctaag cctttgtttc 16380
ctcactggta aaacaagtat ttggaaatat cattgtgaag attagaaata atacatgaaa 16440
agatcctagg atgctgtctg tcatacagta gtagtagtaa gaagttattc ttgccaaaga 16500
ttgttgagaa tggcagaatt atctcagttc taagagctat agtttctaat tatttgagcc 16560
tagactcaga ttcatttgga gcagctaact gctcaccaag agcttatttt ccatcttacc 16620
aatgaggtta tgtgccctgt gtttttaaaa tcagtctact taaccaagag aacagaaatg 16680
acatgagaat taagtaatct cactttctct gttatttagg atttattcct actcaaaacc 16740
tgagagttgc tatgaattca ccattaaagc acttattaat atacatgggt tactgttata 16800
aatagcaata gtattgctat tgtgtgagtt aggtgttgaa gttcaagaaa ggaataaaga 16860
atatttagaa gatctttgaa aacagtgtct gggtacggtg gctcatgcct gtaatctcag 16920
cactttggga ggccgaggca ggcagatcac ttgaggtcac gagttcaaga ccagcctggg 16980
caacttggcg agacctcgtc tctacaagat atacaaaaat tagccgggta tgttggcatg 17040
cacctgtaat cccagctact taggaggctg aagcacaaga atcacttgaa cctgggaagc 17100
agaggttgca gtgagccaag attgtaccac tgcactccag cctgggcaat agagcaacac 17160
tctgtctcga aaaaaaaaaa aaaaaaaaaa aaaagaaaga aagaaggaag gaaggaaaga 17220
aaaaaaaagg aaaaaatgca aggaaggtat ttggtgaatc tataataata aaaatgtatt 17280

-continued

```
tgtcatttcc tttttctgtg ctctcattct ataaaattga gtaaaaaatc tatatatagt  17340
ttaaacacat taatagaaat cacaaaagtt agctgagtca acattgtaga aacataatat  17400
ttctgtatgt caaagaaata gacaacatta aaaagcagaa agcaattaca aagaatgatt  17460
ataagaaaca tcacaaaggg ttaatatttt aacacatttg aaactcaaaa atcactgaga  17520
aaagcagtag acttccataa atattttata gagtagaaaa aataggccaa gcacagtggc  17580
tcatgcctgt aattccagca ctttgggagg ccgaggaggg tggatcacga ggtcaggagt  17640
tcaagaccag cccggccaag atggtgaaac cccatctcta ctaaaaatac aaaaactagc  17700
caggcgtggt ggcaggtgcc tgtaatccca gctacttggg aggctgaggc agggaattgc  17760
ttaaaccctt aaacccggga ggtggaggtt gcagtgagcc aagttcgcac cactgcattc  17820
cagcctgggc gacagaacga gactctgtct cagaaaaaga aaagaaaaga atagaaaaag  17880
aatccatggg caggcacagt ggctcatgct tataatccca gtactctagg aagccaaggt  17940
gagaggatca attgaggcca ggagttcaag gccagcctgg gcaacatagc aagactttgt  18000
ctctattaaa aattttaaaa ttagccaggc atggtgacgc acacctgtag tcccaattac  18060
ttgggagcct gaggcaggag aactgcttga ggctgcagtg agctatgatt agaccactgc  18120
actccagcct gagctacaca gtgagacctt gtgtcaaaaa agtaaaaaaa taaaaattag  18180
ccaggcatgg tggcacatgc ctgtagtccc agctactcag gaggctgagg caagaggatg  18240
acttgagtct ggaagatgga gactgcagtg agctgtggtc atgccactgc actccagcct  18300
gggtgacaga gcaagaccct gtctcaaaaa aaaaaaaaag aaaagaaaag aaaaataaat  18360
aaaatttatt caaatacaaa agtgatgtgg tttgactctg tgttgccacc cagatctcat  18420
ctccaattgt aatccccgtg tattgacgga ggttcctggt aggagatgat tggatcatgg  18480
ggatggtttc ccctctgctg ttctcatgat agtgagtgag ttctcatgaa atctggttgt  18540
ttggtaggtg tctgtcactt accccttctt tttctctctc ctgctgcctt gtgaagaagg  18600
tacttccttc tcctttgcct tccaccatga ttataagttt cctgaggcct tcccagccat  18660
ttggaactgt aagtcaatta aacctctttc ctttataaat taccgagtct caggcagttt  18720
tttatagaag tgtgaaaatg gtctaataca gagacttggt accaggagtg gggtactgct  18780
ataaaaaata acctgaagat atggaagcga ctctggaact gggtaacagg cagcaattgg  18840
aacagtttgg agggctcaga agaagacagg aagatgtggg aaagtttgga atttcctaga  18900
gacttgttga atggctttga ccaatacact gatagtgata tggacaatga agtccaggct  18960
gagatggtct caggtggaga tgaggaactt attgggaact ggagtaaacg tcactcttac  19020
atgttttagc gaagagactg gcagcatttt tcccctgccc tagagatctg tggaactttg  19080
aacttgagag acatgattta gagtatctgg cagaagatat ttctaagcac caaagcattc  19140
gagaggtgac ctggcttttc ctgaaagcat acagttatat gtgctcacaa agagatggtt  19200
tgaaattgga acttatgttt aaaggggaag cagagtgcaa caaaagttta gggagtttgc  19260
agcctgacca tgtggtagaa aagaaaaacc cattttctgg ggagaaattc aagctggctg  19320
gagaaatttg cataagtaac gaggagctga atgtgagttg ccaagacaat ggggtaaatg  19380
tctccagggc gtttcagaaa atcttcaggg cagaccctca caacacaagc ctggaggcct  19440
agaagggaaa aatggtgtga gccaggccca ggcccaggcc ccagctgttc tgtgcagcct  19500
tgggacatgg caccctgtgt tccagccact ccagctccag ctgtggttaa aaggagccaa  19560
ggtacagctg gaccattgct tcagagggta caaatcccaa gcattagcag cttccatgtg  19620
gtgttgggtc tttgggtgca cagaagacaa aagttgagct ttggaagccg ctgcctagat  19680
```

ttcagaggat gtatggaaac acctcgatgt ccaggcagaa gtctgctgca ggggcagagc 19740
cttatggaga acctctgcta gggcaatgca ggggggaaat gtggggttgg agctcccaca 19800
cagagtcccc actggggcac tgcctcatgg agctgtgaga aaaggaccac catcctccag 19860
actccagaat ggtagatcca ccaacagatt gcactctgcg cttagaaaag ctgcaggcac 19920
tcaatgccag cctgtgaaag cagctgcagg ggctgtaccc tgcagagcca cagaggtgga 19980
gctgtccaag gccatgggag cccacccctt gcattagcat ggagacaggg gatcaaagga 20040
gattttggag atctaagatt taatgaatgc cctgtcgagt ttcagacttg aatggggcct 20100
gtgacccctt tgttttggcc aatttctcct atttggaatg ggaacatata cccaatgcct 20160
gtacccccat tgtatcttgg aagtaactaa cttgcttttg attttacaga ctcaggcaga 20220
agggacttgc cttgtctcag atgagacttt ggacttgaac ttttgagtta atgttggaac 20280
gaattaagac attggggttc tgttgggaag gcgtatttgg ttttgaaatg tgagaaggac 20340
atgagatttt ggaggggcca ggggtagaat gatatggttt gactctgtgt ctccacccaa 20400
atctcatctc caattgtaat ccccatgtgt caagggaggg acctgatggg aggtgactga 20460
atcataggggg cagtttcccc catgctgttt gcatgatagt gagggagttc tcatgagatc 20520
tggttttttg gtaagtgtct gggcttcccc cttttccctc tctctcctac tgccttgtga 20580
agaaggtact tgcttctcct ttgccttctg ccatgattgt aagtttcctg aggtctcccc 20640
agccattcag aactgtgagt caattaaacc tcttcctgcc tattctcagg cagttcttta 20700
tagcagtatg aaaatggact actacagaaa gtgtgtaact ttaaactcag tagtatccaa 20760
agaagtaatg aaaatggaga aacgaacaac aaaatcatag tacaatatgg tgtatgtact 20820
aggacaggaa gagccctttt aagaagagat ctatgtattt ccatttgttt atctctgaaa 20880
gaaagcaact ttgccttgta ttctgaaaaa gaaaggaata ttttatttta cttgtaaaaa 20940
tcttacaagg atgctagtct aaatatagtt ttcctaattt gccagagaat ccatgaagat 21000
cgagttgata acaagatcag tgaagtaaag gtcagtgagt taatctcaca gcagctgcag 21060
gctaattcca tttccagtga aaaacgtctt gattgctcac cacatatctt ttcaccacaa 21120
acagtttcag tcttaagatc acatgttgca atccatgaga agtaactatt aagccttcaa 21180
ctatgactgg agggctcctc gccctttctg ataaattgac tggacaaaaa ctcaatttta 21240
aaatgacaag aaatagaaga tgtataaatg tactttaaat gtgaccaaaa tgggttgtga 21300
aaacacaaga cacaatatcc aaaaatgctg gcaacacagt acactgtaga gtattggttg 21360
tttatttacc cttgctattg tgtggctgag cttactgcca ctgcccagca ttgcaagggc 21420
atcaaactgc ctatcactag cctaggaaaa gatcaaaatt caaaattcta agtacagttt 21480
ctactgaatg cttatcactt ttgcaccatt ttaaagtaaa aaaatcagta agttgaacca 21540
tcatatatcc aagattgtct gtatataaat attatacatc tttctctcac ttttaaaaca 21600
aaataatact agccaatact accattctca aaagcacttg tgtcaacagc ctttacccct 21660
taaagatttt cctcacaatt ttaaaattgt tacttactat tttctttgaa atgttgacca 21720
aacctggatt aaaagatttg ggggttttag tgactgtatt tcacaaactc tcttattgat 21780
tctgcagcct cacttctgcc tcctaaaaag ccctcaccaa ggtcacgggg gatggctctt 21840
ttcagcctct tcctggcatt tggtccagtg gcatttggca ttctaggact tccctctttg 21900
tctttgataa ctccctctct tcctgtgttc ctccttgctg tgttcacttg cttcgctttc 21960
ttctttctga agcatgttta cacagtgttt tctctgattg ggcctgtgac gttctttagg 22020

-continued

```
tcatcttttc cacaaataat gcttcaacta gtacttgcgt gccagtgact ccacgtccca  22080
ctcatgagct ctgaacctag taccagcttc tgctggacat ctacaatggg atctctcaca  22140
ggcctctctc attggtaaca tgccccagcc tgaactcatc tcccacccat ctatccagcc  22200
atgctctcta gttcacctga acacttgggt gtcatcctag atgctttccc ttcccagtct  22260
tctgtgatca ttctgcctca tcagaggctc tctaatctgt cttctttcct atatcgctct  22320
tgtccctatt ttaatcctaa tcatctattt cctgacttat tcattcctta agttggtcag  22380
taatttaatt aaaaacagat ttaggccctg accttaaatg tgataagtga tatgaaagga  22440
gatgactggg gaaaaggatt tccctcaagg aaggcctctg tgaagcctga agcaagaatg  22500
aaaacgagtc agacgaagag agaattgtat gaatgaaggc tctgaggcag gaaaacactc  22560
agatcattcc agaatcactt agaagccaag tgaagccagt tcctggagag cagatcatca  22620
aatgaagatg gaaaggtgac caggggccag acctgtagtt ttggtgggcc ttggtgaggg  22680
atttacagta ggacacccca tggtttaagt atgaaagtga caagattcct ttaagtttta  22740
agaggcctcg aaatatgaac cacagattag atggaagcta ctctccctgt gtctggactt  22800
tttagaattt ccaagagctg ctgtttctgg aaccagatta atacaagtca gtcttccatt  22860
tatttattta tgtatttatt tgagacaggg tctcactctg tcacccaggc tggggtgcag  22920
tggcatgaac acagctcact gcagcttggg ggctcaagag atcctcctgc ctcagcctcc  22980
catgtagttg ggaccacagg cacctaccac ccagctaatt ttatttgttg tagaaatgag  23040
gtctcatttt gctgcccagg ctgttcttga actcttgggc tcaagcgatc ctcctgcaac  23100
atcttcccaa agtgctggga tcactcttcc atttaacatg ctatctcaac gtcaagataa  23160
actttaaaat ctttagataa taggctggca ttttacttaa acgatcttta cttcttcaga  23220
actgccattc cctataaata tctggttctt caaccacatc aaaccacttg tgatctcaaa  23280
aagcctcagc gtacactgtc ctttctgtca ttctaattcc tcctcatcct tcaaaatcaa  23340
ctcaaggacc agatccaggg agaagcttag tggtgcccac ccgaaccggc cccctccttc  23400
gagttgtgct gccattcggg cccacctctt cacacagggt tgtcagacca gaccagctca  23460
tgcgttcacc gcccttgcag ggatgggatg cagctgtgca cctctcagtg ccgacacctg  23520
gagagtctca cgaaatgttg acaacatggc ctgtttccat ttcttgttca ctaggacttc  23580
tcatttacta acacacagaa tttcctgtag tatgtccact taatcagttc aagcctaata  23640
attccttgat ttgggtatag tgctttgcat ttatatactg atggtcccca acttacgatg  23700
gttcgattta tgatttttca acttcatggt gatgtgaaag tgatacacat tctatagaaa  23760
ccacactttc aattttgaat tttggtcttt ttccaggcta ccatactcta aagatagagc  23820
cacagatccc agtcagccat gtgattatga gggtaagcga ccaatactct acagtgtatt  23880
gtattgccag atggttttgc ccaactagcc taatgtaagt attctaaaca tgtttaaggt  23940
aggccaggct aagctgtgtt gctcattcag taggttaggt atattaaatg cattttcaac  24000
ttatgatatt ttcaatttac aatgagttta tcaggatgta actctactat aagtcaagga  24060
tcatcttgta tagcactttt aatttataga gtcccttcaa atgtttgttt gtattttatt  24120
tccactgcat ccctgtgagg ataccataag ttatacagct aacaaaacag ttagttttcc  24180
tgtgcaaagt gatggcttca tcttgtggca gattacctgg aatactgtgg ccaaggcatc  24240
ttagttctac tgtctttata tatctagtac agttatattt ttatggcagc tctgatttct  24300
tctttggccc aagggttatt aagagaggga aaaaatttaa tttcttaaca gatatatata  24360
tctatgtcaa gtcatatatt taattcaaac ccttaatatt cctaggtaat ttttgtctac  24420
```

-continued

```
tttctctgtc aaagattgaa agatacaggg ttttaagttt ccaactgtaa ttgtagtttt  24480
ggtaattgtt ttattactaa caggtattgc tctgtatatt ttgatgttct gttattcaat  24540
acataagaat tcattacagt tgaatcatca tgtatagtat aatttaccaa tgtaaaataa  24600
ccttttttatc aaactgagta ttcaccttat aatgtcctct gtcagaggat tataatacca  24660
cttaaaacct tttaaaaaat attttgttcc tgataatttt agctttgagt ggttttctta  24720
taacaattct agagatgcgt ttttattttt taaccaagat ttaaagcttt gtgatttagt  24780
aagagtctaa accattcaca gttcatgctt ttttgtcaaa tttctattat ttagtatttt  24840
cctctctttt atattttcct gttattttcc atttctattc ttttgttaga ctggaaattt  24900
tttctttgct ttcttttatc ctagtgattt gaaatttatg taatatatac tattctacaa  24960
taccctttat ttgttttcaa tatttgaacc tatatttttc aacattatta agaataaaat  25020
agtatttgtt gctattttga aatgatagac catgttttta aggcaggttg gtggttgtta  25080
aggcaccagt atcggccagg cacgatggct cacacctgta atctcagcac tttcggaggc  25140
cgaggtgggc agatcgtttg agcccagcac tttggccgat actgtggttt actgtatttt  25200
gttctagttt attttatgga aaatgggaat tcagtggtta agacaaggat taaatagcag  25260
aagaaagatg tgtacatatg tacagatgta tgtgtccttt atatgttttt tagtactctt  25320
gtctcctttc tggtcctcat ttaaggttat ctatttcatg cagtaaattt ttcttcacaa  25380
ttcatttcat ttagagagtg aatgctacct tccaagtggg ctttctccag ttttcctttc  25440
agggacttaa aggagaagtg atgttaacag ttttatattt ccattgcatt ttacagtgtg  25500
cagatgtctt cacatatatt tccccatttg agctttacaa aagcccttag tattattctc  25560
attgtctaga ttccaaaatc aggcttagag gagttaaata gttgtccagg atctcaagat  25620
gcaagaccca caatcatgaa cagaggcaga tgttcaggat ggaggcaagc tgaaactcaa  25680
aaccaaatca ttatgactcc aaattcagga gtcttttagc tgccacctgc atgggctctt  25740
ggtgtagctg accaccagag tttgtagagc tgtcattcag gtgtgccatg gactttcctg  25800
ggacctggca caggagaagg actgagttaa tgtttgctga ttaaatatct gttacaggct  25860
gggcgcggtg gctcacgacc gtaatcccag cactttggga ggccgagcag ggaggatcac  25920
ttgagctcac aagtttgaga ccagcctggg cagcatggcg aaaccccgtc tctacaaaaa  25980
atttgaaaat tagctggcca tggtgatgca tgcctgtagt cccaggtact caggaagctg  26040
aggtgggagg atcacatgag cccatgagat tgaagctgca gtgagctgag atggtgccac  26100
tgcactccag ccttggccat agagccagac cttatctcaa aaaaaaaaaa aaaaagttac  26160
aataatcttc ccttcaaagc tggaaggcat tatttacctg tctgtccagc agatggtgct  26220
acataaccaa gggaatctgt tgcttgccct tggtgaagct attaaagcca atacagatct  26280
tgagaatttc aaaagcaaaa atcaatactg gattatgagt gctctaggaa aataaagaga  26340
taaattttca atttacatac ttatatatag ttataccata tttgtaaata aaaatatata  26400
aataatttat caaaattcct ttttaacagc aacaaccaca gtaaacccac aggttaaaaa  26460
ctccacaaca gtctatatta atcagtcaat gcaaagtaca ttccaattcc aagttaactg  26520
aaaataatca acttaatcat ttggttggct ctgagcagcc ttcactgctt gctcttgtgt  26580
catgtttctt tctgtcctcg attggctata gacttacaga cggcttttgc agaggacagt  26640
gtactcatgt ccatcctttg catcctttgt gggagttggc taggcagcac tctccctggg  26700
gacactatga actcctcttc ttgagtgcag agatcacgtc ttgttcatct tcatgcccaa  26760
```

-continued

```
taccttgttc cataaatatg aatggattag aattctaaac tcttaactct gccccaagac  26820
agttctgaga ggtagtaagt catataacac ctgaagagga ctgttcttgt cctaattaca  26880
ttaggttata agatgacagg tgagggagcc aaaccagggg gcctggaaat tattcataca  26940
tctctagata cagtatacaa gttgtgtgta ttatgtgtat ttactctgta attgattgct  27000
tgagatgaac ccccaaacac actcgtgttt ggatcattat tatctaccct tctccttaaa  27060
taatcttaat ttcctatgat gcttgaaagg gaaagagggg ccaggtgtgg tggttcacac  27120
ctgtaatccc agcactttgg gaggctgagg tgggagcatc acctgaggtc tggagttcaa  27180
gaccaacctg accaacatgg tgaaaccctg tctctactaa aaataaaaaa tcagctgggc  27240
atggtagcac atgcctgtaa tcccagctac ttgggaggct gaagtgggag aatcgcttga  27300
acctgggagg gggaggttgc agtgagccga gatcactcca ttgcactcca gactgggcaa  27360
caacagtgaa actccgtctc aaaaaaaaaa aaaaaaaaaa ggcagagtgg ggaagagagc  27420
tgcatgaagg agagatttac taaatagtac ttaatcccaa aataatttct ataggtttga  27480
atatgatccc tgaaatttat tataggttca ggtaagtatt aatcacgggt attcagaact  27540
gtggtttaaa aaatgtatag aacatgtttc cttccccttg aaacttttta tcagctaatt  27600
ataggaatta tattatacct gcaatcatta aagtccagaa tgagacagta cttggtaaag  27660
tgctgaaatt tataataaat gcattatagc aatccagtta aggaggaaga gccaccatta  27720
ttgaacattt gttaagtgtc agccattgta ctagataaat tttagttatt atttttattt  27780
aggcaccaaa aaatccatgg gatagttggt tatccccatc ttactgaaga ggaaactgaa  27840
gctcagaaag tttaagcaac ttgcacaggt cacatagcaa gtaaggagca tggccaggaa  27900
tcagaccctg atctcctttg gtctactaag cttgcaaagg atcttcccgc ctccttccaa  27960
gaccattcaa tattatcagt aaatgtccat ggcaaggatg tagttcgagt tatagggttc  28020
cattcaagat atgattggta ggtgggaagc agatatgtct gtgtcaatca gtatcctgga  28080
agaaggagat gatgaactca agtggtgatt aagggaagtt taatgaaggg actatttaca  28140
gagatgtggt ggggttaaga gaaccaacaa ggggaagtga tgcactcaaa aagttactac  28200
ctccaggctt taggggattg ggggagggag tggcacagtg tgaacccagt gtggttgtga  28260
gaaaagggat tccctcagca gccatggcca aggttagagt ctccactgcc aaactgcatc  28320
caggtggtga gggaatggag aataggggtg gggtaacaaa ctctgacctc ggtatcccca  28380
aagggcaaag gattccaggt ggtacagttc gtaaagatta gcctcagggc acagaacagg  28440
gcagagaaga atggagaatt gatctggagg aaacaaacaa tggcttgccc atgttattgc  28500
agggagagta ggctggtgtg cacagcagga gggtggggag cccagcatat agctgtgttg  28560
gggcctgtgc agatcagcct cactggcagg gaggatctga gccgagaggt ggtggaagat  28620
gaaatcgagt aggcatgttg gtagtcctaa atatcaagta aacgttcctg atcttacatt  28680
gatactcaat agtaagccaa ttttgtttcc cataagccaa tattaatatt acgtatttct  28740
tttataagcc agagatatag agagataccc tagaagaatg ataggggaaa ggaaggcaag  28800
ggtgagagaa gaccttgtgt gaatttgtcc aaaatgttta tccacaggaa caatcccttt  28860
gtgaaggctg ctggtatgtg aatgtgtgcc ggttcccttg gggcgttcat ttggatcttt  28920
ctgtgttcca gtgacctacg gcatgatgag ctccaatgtg tactactaca cccggatgat  28980
gtcacagctc ttcctagaca cccccgtgtc caaaacggag aaaactaact ttaaaactct  29040
gtcttccatg gaagacttct ggaaggtatt tgcaaataac tttgaaagta cctctctatc  29100
acagaaaatt gttcatttgg cttcatcatt tcaatgcatg agtatcgaca ggacctgctt  29160
```

-continued

```
tgcatttaac actgtgtgag acgtaagtta tggtgagttg ttagaagtta ctgttcctac  29220
tctcaaaggg ggtaaactaa cattgagaac tttgcctgtg ccttgcactg tgctgagtgt  29280
ttcatatctt accttattta atttctatag tctaactcta taaggtaagt actaagacta  29340
tgccctagtt tgttaatgag gaaaatgaga ttcaggatgt ttaaatgcgt atggtcacat  29400
ggctagggaa caagaaaaat tgattttttt ctagcctgac agctacttca tcctagtttg  29460
taattcattc catgagtcaa gattcaataa atatttattg agaatctcct agaatgtaag  29520
gccaatgaag ggcagtgtgg ttcttctgtc ttgcttcgcc ttttgtgttt tgtctctttg  29580
ttgatgatgg catgtatccc cagctcttag aacagtgctt gattcaaagt aagcacattc  29640
tttcaaaggt ctgctgttgg tggggcttgg tggctcacgc ctgtaatccc agcactttgg  29700
gaggccaagg caggaggatt gctttagccc aggattttga aaccagctgg gcacaacata  29760
gtatgacttt gtctctccaa aaaagttaaa gaattagcag ggtgtggtgg tacacacctg  29820
cagtcccagc tactcaggag gctgaggtgg gagaatcact tgagcgattg cttgaggtca  29880
aggctgcagt gagccatggc catgctactg cattccagct ggggcaacag agtgagaccc  29940
tttctcaaaa aaaatccccc ccaaaaaaaa acccaaaaac aaacaaaaaa ggtctgctgt  30000
tgtgaagttc aacccaatcc agccccttcc caagttgtca caaattccaa cgtagttaac  30060
agtataccaa tgagtgatac cacaggaaaa atattaaact gatctgaggg atatggggct  30120
tggaatctaa gaaaattgga agggaaattg aaaaggaaat tattatttct ccttggggag  30180
atagtttcta aaattcttac tacaccctgg ggtcagagct gttgatttta aggatagaga  30240
caactgagtc acaggaaact attcatatat aaaagtacct ggcatccaaa accacacttg  30300
tataatatga atctttcacc atctgagtag ggcaaatcag tctatctctg ttgatcatct  30360
gacaaggata gcacactgag aaatagatct gtcttcccta caggcatagc tagttgtaca  30420
aactaacaag agacttttgt atacacattc catgatgata aatgccaatc actaaaggga  30480
cgaggaggga ttggagagtt caccatacag caaaatagtc cagacaggtg aaaggtctat  30540
caaatgccag gctggtaatc aaaactgtag ccttttctct aaacaaagtt tagaaccatg  30600
attgtgtggg acattatttt aataagggaa agtgcagtta atcatgaccc cacctttagt  30660
ccaagaacaa aaatcagagc tgccacgtat taagtaccca ctctgtgcca ggtgcagtaa  30720
ctatgcaaaa gatgggtttt ccagatgcaa gaaccttggt tcagaggacc ctgctcaagg  30780
cctcatagct aacaaatgat ggggcaagat gctatcccaa atctctctga caacaaaact  30840
cattcttatc actctactat tttcatagag ttgccaaatg cttggttatg caaacgatgc  30900
aggcaggggc aagacagcgg ctgagcttgg aactttttca gagatgtttc ctttgctttt  30960
agttcacaga aggctcctta ttggatgggc tgtactggaa gatgcagccc agcaaccaga  31020
ctgaagctga caaccgaagt ttcatcttct atgagaacct gctgttaggg gttccacgaa  31080
tacggcaact ccgagtcaga aatggatcct gctctatccc ccaggacttg agagatgaaa  31140
ttaaagagtg ctatgatgtc tactctgtca gtagtgaaga tagggctccc tttgggcccc  31200
gaaatggaac cgcgtaagtg tctgtgactc attgccactc ggtgatattc attcatttat  31260
tctctgaact cccaccattc attcattcat tccctgacac cttcaccaag gcaaaaataa  31320
gttcagtgac tcttcagtgc ttatatttaa accttggcca acttgacctt tgacttctta  31380
agttttcact acttcttagc cttcttttag tttctacatg catatttttc agaagactaa  31440
atcgttgacc atataacccc tcaaaaatta attatctgag cgtttgaaaa tttcatttaa  31500
```

gatgccctgg gccctgtttt tacaggtgca gtaacatcat ccactaagtt atttaacaca 31560
agttttctgg ttcaggaact ctttttatag gtcttgcaaa caggtttttg ttcagaatgg 31620
agttatttaa tgtgtaagct tgtgaggcaa ttttttgtta ggtttaaagc ccattttgtt 31680
caaatgtttg agattttagg tatatatttg tacacgtgca tatttacagg ggctttttgt 31740
acactttggt actcctactt caaacatctt gtgtattaag ggaggtcact tactatttta 31800
gaagtattgt agttattata aagaaacaag aagacctcca aggccgtttc agggtgggcc 31860
tttgcggttg ctgtccctgg gtacgtcact ggtcggagtc atcttctaag ctttgctcag 31920
ctaattctgt cggttcatct aggttctttt cttggaaact gagttgccca gaatccacat 31980
ttgttactat acaatgggca atcacctttt caattagtat attcttcttg taccttccag 32040
tatacactct atttaatacc agaacccata agaaacaaat ttagtaaaaa tccaggttgg 32100
gcacagtttc tcatgcctgt aatcccagca ctttggaaag ccaaggcgga cagatcactt 32160
gaggtcagga gttcaagacc agcctagcca acatggtgaa accctgactc tactaaaaat 32220
acaaaaatta gctgggtgtg gtgacatgtg cctatagtca cagctattcg ggaggctgag 32280
gcaggagaat tgcttgagcc cgagtggtgg gggttgcagt gagctgaggt ctcatcattg 32340
cactccagcc tgggcaacag agcaagactc cccctcaaaa aaaaaaaaaa acaaatttag 32400
tgaaaatcca gagctttaga acaaaggaac taaatagtct caaaggacat tatcatccaa 32460
gttatgatag tgatttcgct ttctttaaaa aaaaaattat tacagataga gtttcttgat 32520
gttgcccagg ctggcctcaa actcctgggc tcaagcagtc ctccagcctc agcctcccaa 32580
gtagctggga ctatgagaat atgccaccat gcccagcttt attttgcttt ctaatgtgcc 32640
tttttgtagt tcctgcaaag cataagcatg ccttcatctg tggtaccctt tccaatattt 32700
tatttatctc acatcactaa taagataaat ttatacagcc actgctctgt gccagacatt 32760
atttaagaag ttatttcacg cattatctca tctgccttca caaaacaact ctaaaatagg 32820
tatcacctcc attttataga tgaaaaaact gaggctcact tgcccaaagt gtcacagcta 32880
acaaattgga ctgaaccaag atttaagcag cctgactcca aaacccatgt ttcgcctact 32940
aaacctcttc catattaatt cctcctccat attaattgcg tcgttagggt ggcttgtcga 33000
cgctctcagc tccccatcag tactcaagct tcctgagggc agggattcta ttttgttaac 33060
tgctgtattc tcaaagcctt gaacaatgcc tcatatgtaa agatactaat aaatatgtgc 33120
tggatgcatt cgagtgattt ctactccagg gtggattgcc aaaggggacc ttccctgtca 33180
tatctaaact atccttttat tcttctacat tctcaagtca ctcccatttc ttcttccctt 33240
caactccaaa cttcttggaa gaatagtctt catttgccac ttccatttcc ttaccatcaa 33300
ttcacgtctt aaagcttagg ttcttgcttt tgacatctca ccaggaagct actagggacc 33360
tctagttagc aaatccactg aacaaatctc agtttttatc cccttcatac tgtctgcaga 33420
aagtggcagt gttgaccgct cattcttttg acttccatga agaactctac actttgggtt 33480
cttttaactc tgaaacccct ttctctcact tctcttattc ccaggttcta tattcatatc 33540
tccgtctttt ctttctttc tctctttccc atgacattca gatggcttcc actgacatct 33600
ttatttggtg actcatcatt tcttcaacaa tgtgccaggc atgttcccat tgctagaagt 33660
ccccccctctt ctagtagtgc ccttgatgct ggagaaacaa agcagcagga aacagaagaa 33720
acgtcctttc ttcacagagc ttgcattcta gtgatacaag acacatctct attccacctg 33780
gatgtcccac acctcttgtg atttaatatg ccccaaacta aactcatcgt tttcttatga 33840
gatctgctct ttgttctgtt aatggcactg ccgtcttcct attgccctga aagagactcc 33900
agagtcattt ttgagccatg tttcctcctt gccccaactt ccaaatcagt taccaagttc 33960
tgctggcagt cactgtggtt acgacactct ctcactcctt cctttccctt cccatcttca 34020
ctgagtgact tcaggcctca ttacctcttg gttattgcag actttgctaa gggagctgtg 34080
tcaggggtcc ctaagaccac ccccaggttc agtgattcac tagaaggact cagcatagag 34140
gcatccttac agctaaggtt tattatggtg aaaggataca aaagaaaagg cacatggcaa 34200
tatctgggga aaacctggtg taggcttcca ggagccctct cccagtgagg tcacatagga 34260
tgtgctgaat ttctccagga acgagttgta gcaacatgtg tgaaatgtct atcagagaga 34320
ttaattagag actcagtgcc tggggtgttc actgggtact ggtactggtt tatgactagc 34380
atgtgccaaa attcccgact ctcagaagga aagcaggtgt tgagtgtaag ccacattgct 34440
tatacaaata gcacaggcac agcaagcctc tcttaccggt cagggaaagt tgaatactgg 34500
tgcagggagc tgtttatcag tcaagttccc agatgccagc caaagtccaa ccttgcaaac 34560
aggccttcct aaagaaaggc catctcaggc ctgctgtgtt aactcttttc tgcacatgag 34620
ccctctgttc ctccccactc cagtcttccc tgctgccacc agaccagccc tgttgtgtgc 34680
ctcttagaac tttcccttca cagactcctt catgtttgcc cttcacaagc tgaccacaga 34740
ccacctttca atctgccatt ctttatctta tgggagccaa actgaactac ttcttctctt 34800
gaccaatggc tcacggttga aaatgccctt cccatttgta ttagtctggt ctcatgctgc 34860
tgataaagac atacctgaga ctgggcaatt taccaaagaa agaggtttaa tggacttaca 34920
gttccacatg gctggggagg cctcacaatc atggtggaag gcgaggagca agtcacgtct 34980
tacgtggatg gcagcaggca aagagagaga gcttgtgcag ggaaaatccc acttataaaa 35040
ccatcagatc tcgtgagact tactcactat catgagacca gcatgggaaa gacctgcccc 35100
catgattcaa ttacctccta ccgggtttct ccaacaaaac atgggaattg tgggagttac 35160
aattcaagat gagtttggtt ggggacacag ccaacccata tgaccattca cctgtgcaag 35220
tccagatcct actcaccttt catggttcag gtccaacaca gcttcttcct aaagcctttt 35280
ctaatccatc cctccactgc cagatcccca aataaggaca gctttcctct gatctgccag 35340
ccttatttct tttctctttt gcttcttatt attatccacc ttgtatttta cttgtttaat 35400
tataactctt atttccctac ttgttataaa tttgggaggg aaaggacctt tatatcccca 35460
ttagtgctga agaagcatct gttttctaag agatcctctg aatatttgtg gatgaaattc 35520
ccaaatgctg acaatgccac ttgatgaact tgtccctctt ttggctgtaa ttttctctgg 35580
ggacctcaag tcgtctagtc cctgagcaca gttacccaga gaaggcagcc gtataaactg 35640
agcagaggct ctagagcaga gcagaggctc tagggacaaa cagccctggc attggttccc 35700
gagtctgccc tcaaaagctt tgggactaca ttgacctcac taagcctcag ggccctcatt 35760
cctaaagagg ctaataacag tatgagaatt aaccaagaaa acatgaactg ccaggtcagg 35820
cacagtaccc agcttgatag gccttaatac atactttatt ttacaaggaa ccagctgtcc 35880
ttgtaattgc ctcaagtgtt ccactgattg taactgtttg ttttttggtt ttgtttttaa 35940
tcagttggat ctacacaagt gaaaaagact tgaatggtag tagccactgg ggaatcattg 36000
caacttatag tggagctggc tattatctgg atttgtcaag aacaagagag gaaacagctg 36060
cacaagttgc tagcctcaag aaaaatgtct ggctggaccg aggaaccagg gcaactttta 36120
ttgacttctc agtgtacaac gccaacatta acctgttctg tgtggtcagg tgtgtactga 36180
ggacatgcat ccctcctatt tctgtgtggt tgtacataca tcctattctg gggttagcca 36240

```
gaaaaacctt tgcctgcagt tagctacatg aggatgccaa ggacccagac ggatagcaag  36300
ggaggggtaa aaactgaagg cttaccgaaa taaaggatat ttgaggaagg gagttgggat  36360
cctagaatat tacgagttgg aaagaaccat aactctggtc caagttcatc tcaatgctgg  36420
aacctttcca gaaaaagtat tgtgtttttc taacatctgt ctttacccat tataaggatg  36480
gttagtgcca catgttccat caccaagtcc cccggccatc aaatcttgac tcatttcctg  36540
gagtttctca ctctcagatg agcctctgct attagcacac aagcacagta accggagtgc  36600
ttgtaggatg ctcagtagga tacccaggtt acctgctcgt gctcagggct accaaaggca  36660
cgtaaagttc cttccacaga tcctgggatg ttgccatgat gacccctctg tgagatagta  36720
acaaaaatga caaagattcc actggcttgt ctgggactct tcttcattca tttattcagc  36780
aaacattcat tggacactta atatgggcta ggcattgttc tcggctcttg ggacatgtca  36840
gcaaacaaaa taaagatccg caccttggca gagcttgcat ccaaccagga ggagactaga  36900
gaataaacat taaacaatac aaataaatag tatagtatat tagaaggtaa taggtactat  36960
taaaaagaaa gaaaaagcag agcaagagga agtcagagtt cacccacttt aatcttcctg  37020
gtgagcatgt cagcaacacc caaacatcac taacatggat tattgcatgt atatttacac  37080
ataagataag aagtgtttat tctcataata gtctttgtca tcattcttga ggttaagttc  37140
aattctgctt tatgtggctt gttggattgt cccagtcctt gtatttaaca acatttgcag  37200
aaaatagtac cacattaaat caattataga ttatccctta tccaaaatgc ttaagaccag  37260
aatgtttgag atttaagaaa tttttcaggt tttggaatgt ctgcatatat ataatgagat  37320
atcttgggga tgggacccaa gtctaaacac aaaattcatt tatgtttcat aaatgaaact  37380
taatgcacat agcctgaagg aaattttatt tttcccttag ggatgttgaa tcaactgttg  37440
tgtgccagca tgttgacaat gacctgtcac atgaagtcgg gtgtggaatt ttccacttgt  37500
gcgttcatgg cggtgctcag aaagtttggg attttgaagc attttatatt tcagattttc  37560
acattagaaa tactcaagct gtccttgctc acagtggcca aaaaaaaaga aagaaagaaa  37620
agaaatactc aaccagtagt ccagtagtag ttatcactag aaatgaatga aaatctattg  37680
cagtattatt gagtttttcc taattattcc agtgcagata aaaagaaaag aataaaaagg  37740
aagagaataa aaacagagag gcaactctga tattttagta aattctattt atagaaggtc  37800
ttgagtattt cttctgcttc ctcccttact ttaaggatga acattgttaa gacaactgct  37860
tcatttctct atactgtttt tctaagtttc tggaagtggt tgactactgc agggccagaa  37920
tgggccagag aaatgacttg acacttgaag gccacttcct tccctttga gttcccaatg  37980
aagctgtcac atacaaggct cttggcttca gagttgctct cctgagtttt tgattctcac  38040
ccctactctc taacacatca aataggaaag aaagaacagg agaactgaca atgaaaagga  38100
aggaaaattt tcacacttct ctgaccagtt ctaatttacc atagtcctgt ttttacttga  38160
ttattgctca tgcatgtgtc ctgtatgctc aggttccagg tgcggctacc tgtcctgtaa  38220
tggcagagat agtgatggct agtagctgac taaagggctt ttaaatgtct caaaatgaag  38280
cagctagaga ttctatttct agttagaaaa gaagtctgta tcattaactg aatcacccag  38340
ctttctcagt gtgacaccta caaaatgggc atttgacaag aaaaaaaccc tcagtccagt  38400
tatggtaaag cagtaaagat cagagccatc agtatggatg taaaatagtg tatgttttag  38460
acaatcagac atctattgag tacccaccta ttaactataa ggctctggga agaagagaga  38520
aaactaccct ggaggacaaa ctatttgatg ctatttaggt gttacataat gaatgaatga  38580
ctcagttcct atctttatat atgtacaaaa tatatcctac ttctcaacca gattacacat  38640
```

gttttgagtg gatggtttat atttctttat attcttcatg ttgcctagta gaaggacttg 38700
aatttaatag aagtcctagg gccaggcatg gtggctcctt cctgtaattc cagcactctg 38760
aaaggcccag gcaggaggat catttgagcc caggagtttg agaccaacct gggcaaaagg 38820
gcaagactca gtctctgcca aaaaaaaaaa aattagttgg gcatggtgct gcacacttac 38880
attcccagct actcaggagg ctaaggcagg agaatccctt gagccctgga atttgaggca 38940
gcagtgagct atgattgcaa cactgcactc cagcctgggc aacaaagcga gtccctgtct 39000
cttaaaaaaa taataacaga agtcctagaa aagtttgtgt gttgatttac ttttacatta 39060
aaagtatatg gcatgttgag cagcgtaaat atagaaaagt gtagggaaga ctgagcagga 39120
agtactcctt tgggactgaa agacctcagg aagtcttatt cctttgatgg cacaaaattc 39180
tccaagtatg gaattattag ctatgataaa aatgttttgc cgctagtttg gggggactca 39240
tggtagcagt ttcattacct tgtaatgcat gaacagaaca gatggacatc cattcctggc 39300
tgtattcatg tgttgttgtt gttattgttt taattgttct tatttacatg caggttattg 39360
gttgaattcc cagcaacagg tggtgtgatt ccatcttggc aatttcagcc tttaaagctg 39420
atccgatatg tcacaacttt tgatttcttc ctggcagcct gtgagattat cttttgtttc 39480
tttatctttt actatgtggt ggaagagata ttggaaattc gcattcacaa actacactat 39540
ttcaggagtt tctggaattg tctggatgtt gtgatcgttg tggtaggttt gagaacaaca 39600
ccaaatttcc tattctattc tacaagcatg ttaactagag tctttgatct cctcagcatt 39660
gtggatcttg atattcccaa aaaagaatct aaaagtcccc ctcaattata tcaacttctg 39720
ttactaatta ttttctcatt ttgcatgagt aactttgctg agtatgaagt ggagaggtat 39780
ttacagtatg ctctcagcca cgctaataac aagagtatct cagtaattca tatttggctt 39840
tagtatgccg tatgagatgt ggaggagaaa acagtttttt ttctttgttt ttttttccac 39900
taatgatatt tttcttcaac tgctggtaaa aatcaattta tattttcctg cacatgtgtg 39960
aagttacagc aataaaaaaa cttgtcggcc aggtgtggta gctcatgcct gtaatcccag 40020
cacttgggga ggccaaggca ggaggatcac ttaagcccca gagttcaagc ccagccaggg 40080
taacatagtg agaccctgtc tttacaaaaa aaaaaaaatt taattagtca ggcatggtgg 40140
cacacacctg tagtctcagc tattccagag gccgaagtgg gaggatcatt tgagcccagg 40200
aggctgaggc tgcagtgagc tataaatgca ccactgcact gcagcctggg tgacagagtg 40260
agaccttgcc tcaaaaagaa aagaaaaaag aaaaatcatc ctgaaaatat tttgtgcggc 40320
agagaaaact ttctgcagtt taaaattttc tgcaaatagt ctgcagagta caaatgtaag 40380
ttatattcat caaagttttc tgtatgaggt ataagaaatc aaaggcaggc catgcacagt 40440
ggctcatacc tataatccct gcactttagg gaactgaggt gggaggatca cttgagatca 40500
ggagtttgat accagcctgg gcaacatagt gagaccccat ctctaaaaaa taaaaataaa 40560
aaataaatca aaggcagagt cataatcaag accatgacac catgtaaatt ctgtgtctgc 40620
tcttgactct attataactt ctaagatttt tttcaagatg ttttcccttc atccttatca 40680
cttaattaag catccgtcac ttccttcctg tggtttcagt gtataaaaga atttttacaa 40740
gcttttctcc cttcagcaat aacaggtaac atttcgctaa gtccagttgt acatttaagc 40800
atataacaac atgcttaatt attagatgct tacaagcttt gcttggcata ggtgtaccat 40860
gtattattct atgtctttcc ttcccactgt cctatgatag ccattacctt ctgaaatctc 40920
agtaaatgat gcactaccct attagcattc tctcttctgt tagccctcct tatgagagtt 40980

-continued

```
attctttccc tcatcccact cctaaaaatt catttggcct ttgtggagta tttagatcaa  41040
gtcattatta aactattccc cactagaatt attaatagtt gataaaatat ggaaaatata  41100
ttattcatat gtgagtgaaa gaacacttaa agcataaaaa agaactacat ggccatatat  41160
tgcatggcaa taactatatt agcagcaata ataattgtaa tagtaataat aataatggct  41220
aacactttag aagcttctgt gttaggcatt tccgggtgct tttcatggta cagaagctca  41280
tttgttcctc atactaaccc tcttcactac tctgccactg cctctcaagc catggatatg  41340
tgcactttag agtttttact taaagtaaaa attcctgtag aatagatggt gttgacccca  41400
tcagaccgtg atgcagttag aagtgcatcc cgtcttttac gatggccata caacatcaca  41460
caaatcaagg taaacccttg atccccaaat tctcaatgta ttaataatga acagagttac  41520
acaagaattt tagcatttaa ggaaacagga gagacgataa tactggaaat aatttttcag  41580
aatatttctg ttcggattga tggcagagtg caggccatat acattgacaa ttattccaga  41640
acacaattat tgtttggagc taaaaggatg caaaccctgc ctcttggctt atatggattt  41700
atttatgttt aggccattga aataatggta gaaaggtaag tatgatatgc taattaagaa  41760
cagacttcct ttttatattt taaccaaaga actcaatatc aacaaaagac tagtcagtgg  41820
tattcaccct ttttgatcat acacacctat cagtgaaagc tttgactact acacacccta  41880
atttattatc tttatttgta aattgtgtgc ctactttggt gtaacaggta catccgtaaa  41940
acatacacat acatagaatt ttaaagattg gaataaaagt taatacaaat agaattccaa  42000
aactttctta ccacctacct agaagttgta acattttctt cccatagccc agtgaattgc  42060
cttgcacctg ctttggcgac caataggaag aaaggcaatg atatcatgga aattgtctct  42120
ttggctcaac agccacagca ttttgcaagt gtttctttga aaacttgctt cactgtgttt  42180
ttcaattttt tttttaaaca acacttaata ctgccagaca acaattcaga cagtgtgctt  42240
tttgtttata aagaacaagg aagggctact ggaatctcac ttgtcctttg aaacttttgc  42300
tgaccaagtg tagaagtgag ggcatgcctt ctgctcaccc acaaaacaca ccctgtgctc  42360
cactggacct tcaaaccagt ggaaagaccc aacgcttttt gttttatcta gccaaaattt  42420
gcttatgctt acccaaaacc tgaaaagaaa ttatattctt aatataaata caatcacatc  42480
ttgaaatcac tttgaaattt tctttatttt cctttttttct ttccccaaca tatgttctga  42540
agtacacagg ctgcatcagt cagccatttg tcctgagcaa tagtctttca aaactagaag  42600
aattacttga aaaaaagaag actattaagg aatttaaact caaataattt attgaccact  42660
tgctaggttg tacagggtaa attttttttt tttttttttt ttttgagatg gagtcttgct  42720
ctgtcaccca gactggagta cagtggcacc atctcggctc actgcaagct ctgcctcccg  42780
ggttcacgcc attctccctc ctcagcctcc tgagtagctg ggactacagg tgcctgccac  42840
catgcccagc taatttttttg tatttttagt agagacaggg tttcaccgag ttagccagga  42900
tggtctcgat ctcctgacct cgtgatccgc ccacctcagc ctcccaaagt gctgggatta  42960
caggcgtgaa ccaccgcgcc tggcccgact aattcattta ttcagcgagt gttttctgag  43020
cacctactat gtacttgcca ctgttctagg cactggggat acaggaatga acaaaatcac  43080
ccaaatctct gccctcccaa ttttctggta tggagagaaa gttcttttgt agatagggat  43140
gagaatccca cagaaaactc aggagtgatg taacaatgca aatgctcaca aaatctcttt  43200
cctcatcttt cattccctat ttggaaggaa aggtttcaaa gacattgatg ttgtataaat  43260
gaccatcttc ttcattattt tataaacatt tgtcctgtgc agagtaaaaa caactggact  43320
gcataacaaa ttatacctat tgagagttgg gtaaagagtt accattggat ccagtccacc  43380
```

```
aacccaaatg tttttctaca tgtattagct gagatgagct cctcatctca ggagaagcct 43440
attcccactg caggccttct tgagtctgct gtgttcatca ttcccaccac caacacaaaa 43500
atacaagatt ggctctggaa atccttcaca gagaaggaag gaaaggaaga tggtgaggtt 43560
ggctttttag ctgtgatcag caaccaagct ggtctttgct atgagaatca gtgggaccat 43620
gatctctatg gtcatctcag gaagggaggg ctaatgaagt ggtctctggc catgattcct 43680
aagaagagag aatggacagc aaagatcgca gcacctgcca cagcccacct gctgcagatt 43740
cagacccccct ggtggggcca ggttgttatg actaacccct agcactgtct acatttagtg 43800
gtgatggatg ccaaggaggg ggcagtgtcc ccttggatct gattgtaaag cttagaacca 43860
aagcatatgt ggaaagttgt agggtcatga gttaagggac agaaatgagc aagagagaag 43920
cccttggctc atatattccc actgcaggcc ttcttgagcc ctctgtattc atcattccca 43980
ctgtctttca agcccaagct catgctttgt tctcatgggc actcattttt aggatatctt 44040
ttgtccctct tgactttatg ttgtgtgata ccaactcttt agtagttttt tgtattattt 44100
aacttcatgt gtttatctgc tcttgagtct cgagggcagg atttatgcag tttacttctg 44160
tttattcctc ttagcccttg cacagtgctg tatacataga catctactat atttttgtta 44220
aacagagcaa agaatggctg gcaattggag aatgcagaga aaccgaaaaa ttttaaattt 44280
aaaaatcaca aataaaaaca gcaggatgaa ggcaagaaag caaaagggtg gaaagtgatt 44340
aaaatgaagg tggcagaaaa aacagaaagc attcctcttt gagtttgagt ctgttatagt 44400
gtgatctctt ctgtgtatgc atgtatgtgt gtgtaatgta tatgtgcaca cacatgcatg 44460
catgccttcg ttgagtttct attccgaact aaggaaatgc aagcaatata ctgttttact 44520
tattttatgg cagggcttaa cactttccat ttgagtgagt gacttttaag aatgacatcg 44580
ggtaagtata atggtgagcc cttataatta atacattggt gaagaaaaat atactagtca 44640
tattaaggta agtttcatat ttctaaaaca ctgtaataaa atataaatat tttgcttttc 44700
agctgtcagt ggtagctata ggaattaaca tatacagaac atcaaatgtg gaggtgctac 44760
tacagtttct ggaagatcaa aatactttcc ccaactttga gcatctggca tattggcaga 44820
tacagttcaa caatatagct gctgtcacag tattttttgt ctggattaag gtaatttata 44880
aatttcatgt tctacatttt aaataatatt ttctttaaaa aaaatgagtt ccacaaaatc 44940
atggaatact tgaatttgaa attcaagtga ccagccaaag ctgctcaata tttactttga 45000
gacagggtct cactctgtca cccaggctgg agtgcagtgg tatgattaca gctcattgca 45060
gcctcgactt cccaggccca agcgatcctc ccaccttatc ctccgaagtc actgggacta 45120
caggcatgtg ccaccatacc cggctaattt ttaaattttt tcgtagagac aaggtctcat 45180
tatgttgccc aggctggttt tgaactcctg ggttcaagca atcctcccac ctcagcctcc 45240
caaagtgctg ggattacagg catgagccac cgtgccaggc ctcatatttt acatataaag 45300
taaactattg agactcatgt gatcattcct ctcactgtca atgacatact tctgctatct 45360
gaattagtgc aagatcagtc cctataggtt ttgtttaaca aatgcagtaa gaggcctttc 45420
agtgtgttag ctgggcctgg ggccccaggc tgctaacaga tgagatgaac aggtgaagga 45480
aaaggaactt agagaaagag agggaaggag caggtggagg gaaggggaga gttgctgcac 45540
ttggaaatgc ttgctagaag ggatcgcctc ttttccaggt agaggctgta agggaagctt 45600
tacctagaat taaggttgga acagacactg cttccaaata gttccttgct cactattttc 45660
cttattgtcc caagatataa tgtgcatttc catgtgtgtg aaaggttatg acatttcata 45720
```

-continued

```
tacaacaagc ctcaattctg gagatgcagg aaatttcaat aattctcagg cagcagctgc  45780
cattcggtca ccagcacagg ctctgattgt gctgtccaga cagtaagtac tagccacatg  45840
tgcctattta aattcaaatt taaattagtt aagcttaaat acaattaaaa acgcagttcc  45900
ttggtcctac tggccacaca ttaagtgttc aatggctact gtctaggaca gtggaaatgt  45960
agaacatttc catcatcaca gaacgttctc ttgaaaagca ctgttctgga aggtacttac  46020
ccgttatgta cttttctgag ttggtattca tacctagaag acctgaggtt tatcacaaga  46080
catagacttg gaccaggcgc agtggctcat gcctgtaatt ccagcatttt gggaggccga  46140
gataggtccc ctgagcccag gagtctgata ccagcctggg caacatggca aaacctcatc  46200
tctactaaaa atacaaaaat tagctggggg tggtggcacg tgcctgtagt cctagctact  46260
taggaggctt aggcgggagg attgcttgaa tccagaaggc ggagggtgca gtgagccaag  46320
atcgcaccgc tgcactccag cctgggcaac agagtgagac cctgtctcaa aaaaaaaaaa  46380
aaaatgcata gactttatcc tgtatttctc atgctattta tttattgaca tgcttgttca  46440
agagaaacca tcactaaagc acaaaacctt gatcataaca tagtaataat aatcaaacag  46500
caaaaataat aatagtaata agaatgttct gtggtgatgg aaatgttcta tattttcatt  46560
gtcctagaca gtagccacta accatgtata ggcatggaac acttaacatg tggctagtag  46620
gaccaaggga ctgaattttt aattgtattt aatcttactt aatttaaatt tgaatttaga  46680
tatccacaca tgtttggata gcacagtcag agcctgtgct ggtgaaagga tggcaggtgc  46740
tgcctgagaa ttactgaagt ttccttgatt attattagtt taataataat aatcaagata  46800
gtaataataa tcaagatagt aataataatc aagatctcag ctgggcacag tggctcacgc  46860
actttgggag gctgaggcgg gcagatcacc tgacgtcggg tttgagacca gcctggccaa  46920
catggtgaaa ccctgtccct actaaaaata caaaaaaaaa aaattagctg ggtgtggtgg  46980
cacgtgccta tgatcccagc tacttgggaa tctgaggcag gagaattgct tgaacccagg  47040
aagcagaggt tgcggtgagc tgaatcatgc cactgcactc cagcctgggc aacagagcag  47100
cacttcgtct caaaaaaaaa aaaaaaagat ctcaaatgaa ttgggattgt attaagtaat  47160
gattaagtaa tgtgattaca gcaatcctca agaaatattt cactgtggcc agtaacaatg  47220
tgtaacagac ctttaaactt ctagagattt tcctacaaca tgtgtctcag gctgatgtgt  47280
tttatttagt gcttctcttg gaaatgtctt gcccctcgat actttatcat taaggtcttt  47340
aaggcaggga tcatgactct actttttttt tttttttttt ttttgggacg gagtcttgct  47400
ctgtcgccca ggctggagtg cagtggcaca atcttagctc actgcaacct ccgtctcctg  47460
ggttcacgcc attctcctgc ctcagcctcc cgagtagctg ggactacagg cggctgccac  47520
cacgcccggc taattttta tatttttagt agagacgggg tttcaccgtg ttagccagga  47580
tggtctcgat ctcctgacct cgtgatccac ccacctcggc ctcccaaagt gctgggatta  47640
caggcttgag ccaccacgcc cggcctcatg actctacttc taatatctca tcatgtgctc  47700
ttccactgag gcttctactt agagctacac aatctgggca gccatcctca gtgccttatc  47760
taccaacatg ctcaatatgg ctttgcaggg ttcactgtct accagcaggg ttcactatct  47820
accaacatgc tcaatatttc tttgcagtca ggcagagcag gctttgcagt tcaggcaggg  47880
cagctggctg caggccccag ctgactcctg ggatagaat gccaatattt cagacattgc  47940
agagatttga ggcaatgtac ataaagccct ccacatataa ctgatgcaca ataaatgaca  48000
gttaatatta tgcaacaaga atttcctggg gggttttata attaattttt atttgtgtga  48060
agtttttcc ctccctttta ctttaatcct tttgggggg aaagcatcac tagtcacagt  48120
```

tcacggcagc ctcgacctcc caggctcaag caaccctccc acctcagcct cctgagtagc 48180
tgaaaccaca ggtgtgtgcc accacacctg actaatttat ttttattttc taatgaaaca 48240
gaatcttgcc atattgccca ggctgatctt aaactcatgg gctcaagcga tcctcctgcc 48300
tcagtcttcc aaagtgccgg gattatagat gtgagccact gcactcagcc tttttttttt 48360
ttttttaat tgtagatagc ataaaaccta ctgttttaac catgcttaag tgtacaattc 48420
agtggcatta agtacattca cagtgttgtg cagccatcgc cattatgctg cattattttc 48480
agaacttttt cattattcta aactgaaact ttgtatccat tgaacactaa ctcccaattc 48540
ccccagtccc tggtaacctc cattctactt tctgtcactg tgagtttgac tattctaagt 48600
acctaattta agtggaatca tacagtattt gtccttttgt gtcaggctta tttcactttg 48660
catgatgttt tcaaggttca tccatgttgt aacctgtcag aatttaattt cttttcagga 48720
tgaaataatg ttttattata tacagtcaca ccattttgtt tatccattca tctattgatg 48780
tcttctctct cttacagctc ttcaaattca tcaattttaa caggaccatg agccagctct 48840
cgacaaccat gtctcgatgt gccaaagacc tgtttggctt tgctattatg ttcttcatta 48900
ttttcctagc gtatgctcag ttggcatacc ttgtctttgg cactcaggtc gatgacttca 48960
gtactttcca agagtgtatg taagtatata tgaaattaag aagaaaaatt taatcagagt 49020
tgtcactgct tctcaagaat aaatcttcat atgaggttgc tatatgacca ccaattattt 49080
aaaaccagtt attttaagta agaattaatt accttttccc aaaacattga tctacccatg 49140
caaagaagac aatgcatcct gaaatgctga tgcttaagat agcagcccaa agtagtaaaa 49200
tacagttaac agacatagga aaccaacact gttctgaaga ctgagttttt ctttgcacca 49260
aatgcagatg gtagcttcta gaaggctgtt tgcctatatt cttactcctg ttgaatattg 49320
ttgccatata tttagaactt caagttattt tctaaggaaa aaaacaagat atttctaata 49380
ttctaaggta aactcagacc agtacaagaa ttttcagttt ttttttccaa agatcccaaa 49440
tgtgaaataa aacaacaaaa agcagccagt gtcagatttc tatgccattt agaaaggagt 49500
tagtttaaaa aggaatggaa gtaatagggt tttgtgcata gatatctcga attaatattg 49560
ctgttgataa aagtgatttt gctaagaccc agcactgaca acacttggcc actttgatcc 49620
cattttaagt acttgtcaga atattggatc tttgaactca aaccattttg ggtttttggg 49680
gtttttttgt tttgtttttt tttgttttgt tttgtttttg aggcacggtc ttgctctgtt 49740
gcccaggctg gagtgcagtg gtgcaatcat agctcactgc agccttgaac tcctaggctc 49800
aagcaatcct gctgcctcag cctgctgagt agctgggact acaagtgtat gccaccatgc 49860
ctggccaatt tttaactttt tttatgagaa gggatctcac tgtgtagccc agggtggtat 49920
tgaactccag ggcctcacac tgtcctctca cctcagcttc caaaagtact gggattacag 49980
gcatgagcca ccacaccagg ccctgttgtt ttttttttaa agaaattttt aactttagac 50040
cgagggtgac tgttgtcaag gtttagggtt aagatgtttt acctagatta tgtgttgaaa 50100
tgttatagcc aattgcttta taagttattg aataataatt gtattttctt tttttttttt 50160
tttttgagat ggagtctcgt tccatcgccc aagctagagt gcagcggtgt aatctcagct 50220
cactgcaacc tctgcctccc gggttcaagc gattctcctg cctcagcctc ccgaatagct 50280
gagattatgg gcgcacgcca ccaagcccag ctaatttttg tatttttagt agagacgggg 50340
tttcactata ttggccaggc tgttctcgaa ctcctgacct cgtgatccgc ccgcctcggc 50400
ctcccaaagt gctgggatta cagacgtgat ccaccgtgcc cagcttgtgt tttcttttta 50460
accaaatgga aataacctct gtagcatgaa agcattttat tattattgca gaaggcttta 50520
attgctgata caagtagcaa gactttgtaa atgggattga caattttctg ttattcggca 50580
gctacctata ctgctaaaag gtccaaaaat aatgaaatca tctttaagaa atgttgcatc 50640
aactagtgga cattctttgt ttttgtattg tggtgttttg ttttattttt atagcttcac 50700
tcaattccgt atcattttgg gcgatatcaa ctttgcagag attgaggaag ctaatcgagt 50760
tttgggacca atttatttca ctacatttgt gttctttatg ttcttcattc ttttggtatg 50820
tacattttta tttatagtga ggttcaattt aaacttcgta aatccttgtc ttctcttttc 50880
tctcacactt tatgtcctat caattttaaa taaagaccca ggaagtagaa aaaagtgtgg 50940
atgttggaaa acttattttc cttttattaa ttcacagttt tgagactcat atcaaatgtc 51000
ttttctgtgg tctttcattg atccatgtat atgtgtctat tcaatgcaaa aaaaattaga 51060
tctcttccat ggtctttcat ttctctctct atatatgtat ctattccatg caaaaaagaa 51120
attagatcaa gtacaaattt ataaagatac ctaaaatagt gctttgccta aaaagtagaa 51180
tatgcttaca tgctttttaa actcatatgt cagcactttc gtagtcactt gctagcatga 51240
cttttctctc tttcttcttt tctttttaaa aaataagaac ggaaaagcaa gctagatcta 51300
agatgtcgag taatagttga gtgaatcatt gcatgtcaaa attaggatat tctgttttaa 51360
attatttata tcccattcat ctagagactg cctacagaga atattcaaat aattaagttt 51420
aaaactaaat gtaacaatga atggaaattg cattaaaatt attttcaaaa ataatttttt 51480
tattctcttg atttggtaca aatgaacatt tttaatgttt ttgccctaag tcaattaagt 51540
tttttaagg tgttttgttc tttttcttaa catttatata ttcaattgtc tactgagaag 51600
gtgttaagcc agcttaattt aggcaatatt tttcatctaa acactaacag tcatcttaag 51660
aacaattttc ttaagaaaat aacatttttt ccatttcagt aaattgtgta aagatccctt 51720
gaggaaggtt aagtgatcac attttcagta attcagtgta ataactctaa agtcagtcca 51780
ggtattactg gttaagtata tggtatttat tgattgggta ttagatgtac tgtattaatt 51840
tcctgtttaa aaaaaatttt ttttccgggg agacacagcc tctggtgtaa aacaaaggtg 51900
tgttccctag ctgtacttta acaggactga aaaggtcagg aatatcattc aagttcatat 51960
gtatcttgct gtatgcatgg tttatggctc atttttaaac ttacacctct taagcttctt 52020
cttcctatca tatattaaaa caatggagag aagaataagc ctctgttact ctaccattga 52080
tagtacttcg gattctagag tacctgaatc tctactaaga aggcaaaaac caggaattga 52140
gagtcctgca cctgaccctt cagttgatct caggccacct agttttctcc gtttatcaat 52200
ctgccaaaca aggatggata gagtcgtggc aactggaaag gctcaaatgt ggaattgttt 52260
gaatgtggtc ctttagtagg cagccatctt accagatcta gagtattcag tcatcttacc 52320
agatcagtca ccagaacatg aaaagaagct cttagtttct atctttatac taaaattgtt 52380
tttttgtacg actgcacaaa aaagaattgc tctccttgca cctcccagag atataggtgg 52440
atagatacat acatacgtac atacatacat acatacatac atacatacat acatagacac 52500
atacatagat agaagtctac tttcaataca aacctgtctt ttaaggaaat gacaagctga 52560
gcatagggtt ggccaccttt ctgagccgat tgcctggtat tagtttattg cccctgttta 52620
gcaagaaggc acagtgttaa gaagtggctc agctgaacca ggataacccc actcttcccc 52680
cacatcaaca ggaaagacat cctggtgcag atgtccatct gataattcag ggaacctcgg 52740
gagacaggat ggagaggagg gtgagctagc ttcctcttcc cacaccttca agagcctttc 52800
tcaagcactt tctatttttt gaaatctctt tagaggtccc agactttgat ctgtttcaat 52860
taaggtattg gcaggcatta gttaacagcc acttggaagc aaaaatagaa cattagatcc 52920
ctgagttgga agagagaagg tagaaggtgt tacttggact gcaattatct gcacttggaa 52980
ttgagcattt agtcaaaaac ttatatgtat tctatattct attctcattt ctgctacaga 53040
attgtaaaca atattcttcc ttaatacaga aattcatagc ccactaaaat aagagcgttc 53100
tcatttgttc atttctcaat catttaataa gtatttacta agccactata tccatatata 53160
tatatatatc atatatactg tataatacac actgtagtgt tttttgtgga ttgtgtacta 53220
tgaggtagta tgttagatac tgccagtact ggggtaagga aaacagcctg attaggccct 53280
tacgaagatt cctcagactt gtggggaaaa cagacattat caaatagaaa tacttgcaaa 53340
ccacagttat gtgttaaaaa ggaaaaacaa agtaaaaaaa aagttggtgg gggggaacct 53400
gatctcctgg atacagtgct tcgagaaagt ttgttgttgg aaatgcaaac cattactact 53460
gtggaaggga aaggtcagaa aaatgaactc accattactg aatagtaata gtagctatca 53520
attaggtggc acttacctgc atcaggacct gtcctgagca ctttacatag attgtctcac 53580
taaccagccc aacaaatatg taagggagat actattattt ttcccatttt attaatgtaa 53640
aacaattaaa taattcttta aaattagact tagaaaagtg gagcaacaat cttagcagtg 53700
ctaggactga aatccaagtt tgcttgactc caaagtctat ctctcttcca gaaacttttt 53760
ctttactatc tgcctagtag gcctgctgta ttcctatttg caacagcctt ttaaactctt 53820
taaaaatgtg tcctgtaaat ttcatatatg attatacaaa aaaacttgga ataagcatac 53880
aattctactt atctgtgtta actgttgaaa tttgaagagc tttttggaat tctataccct 53940
tcagtagtgt atgtaaaagt ttctaaatat agagaacata gataagcaaa aataatatta 54000
aataaaataa tcgcaccatt agtaggtaaa tatactaata ttttgttgta ttttattctt 54060
gtatgttttc acaaagtata tcataaaatt tttcctgtgg catgacttaa cggagaaaat 54120
aatcttccca aaacatgtgg cagcaaaact gttaatttat tacatcaggc tgggcacagt 54180
ggctcacgct tgcaatccca gcactttggg aagccgaggc gggcagatca cttgaggcca 54240
ggagttcgag accagcctgg ccaacgtggt gaaacactgt ctctactaaa aatacaacag 54300
ttagccaggt gtagtggcac atgcctgtaa tcccagctac tcaggaggct gagactcaag 54360
aattgcttga acccaggagg cagaggttgc agtaagctga ggtcgcgccc ctgcactcca 54420
gcctgggcaa cacagtgaga ctctgtctca aaaaaaaaaa ttttttttta aataaataaa 54480
taataaattt atgtcttcat aaagcactca gattaggaaa aaaaggataa acaaaaaggc 54540
atgtgtcatt tttttgattg ataattccaa attatgtttc ttcctttaat ttttgccctc 54600
ctttcattta caaacagaat atgtttttgg ctatcatcaa tgatacttac tctgaagtga 54660
aatctgactt ggcacagcag aaagctgaaa tggaactctc agatcttatc agaaaggtag 54720
gaaaaacctt aattctcaga attcttctgt ttctgacata aaatgagcat tgtttcaccc 54780
agattttcaa atcaacattg atccattgaa attgtttgaa ataaagaata cattgctata 54840
tttcaggaat aatttaaatg ttccctatct tggagtcttg atggatatac tgctatcttg 54900
aattttaatt ctgggaatcc ttttatgccc tggaattaaa ttctcaacaa tcttttgaca 54960
ctttaagagc tgagctgaag gttcatcacc ttcattattt tgacatctcc tgtagctggc 55020
tctcacttca ggatcctgag ttgagaataa actagaaggg aagattatat aaagggattt 55080
ccacctcttc tgtctcaatt accattttaa aaaaataaaa agttttagag gaaaacactt 55140
agtagttcac cctttaccct tgaccttcca cggcagtttt aaaataagca aaggaaaaga 55200

```
ttcatgaatt caggccatag cctggggcct gagaactttt acttatgcac cttctcagga  55260
agggtttcat tgttaaatag aagggcagga caggaaagtt gggcctcttt gttcttctca  55320
atgtaacttc tttatttggt ttaaagtata aaatgtatac aacaacaaat aaccacattt  55380
aaaatacaca gtttgtttcc caacatcatt ttgctaagtc atagtggctc cttaactgta  55440
attttttttt ttattagtcc aagccttagg attatgttat ctgtgatata tgttataata  55500
gaaaacttaa gcctcttaaa acaaagtcct tgggatggga cctaagattc acattatctt  55560
gattccgcat aacagttgct tacattttag caaatctcca gtgtgtatgc aagcactcct  55620
cacttggcac aattctgata cacacaaact ttggttaccc cagttttgtt atgtaacacc  55680
accttcaaca acacagttca aatttcagtt atcatagtat attaactctg agtaacagca  55740
caaagtacaa actccactgc tagctcttca gtgtatagat cagttacctg agtaacagat  55800
gtgcaggctg agcaggctca ctggtcagtc atgacactat tttcagtctg ttactaattg  55860
gtcactgagc atctgctatc caattcacaa acaaagaaag catgtagtgt tgcttccttg  55920
tgttccagta ataagcccat gtgacatttt acaaaaatgg ataattgaaa aagagaatgg  55980
gtgcagtggc tcacgcatgt tgggaggcca aggcggatgg atcacctgag gtcaggagtt  56040
cgaaaccagc ctggccaaca tggtgaaacc ccatctctac taaaaataca aaattagctg  56100
agtgtggcga cagatgcctg taatcccagc tactggggag gctgaggcag gagaatcgct  56160
tgcacctagg aggcggaggt tgcagtgagc cgagatcgtg ccattgcact ccagcctggg  56220
taacaagagc gaaactccgt ctcaaaaaaa aaaaagaaaa gaaaagaaaa gaaaaagaga  56280
atgggctagc aaagaaatga aaaatggtaa cactggaagt gaaaatcaaa acagagtaat  56340
ggatttatag aagaaatagc tgagtgaaga agaaatagga gtgttgacac tgcgatcatt  56400
caagagatcc agatatggag ccagaagaac ttagggcagg tctatcaact taaatgagga  56460
aaatagctgt gataaaacag atgaagatgt cttgaggaaa tgatgcctgc aaaaaacttc  56520
acattaaggg aagtcttatt agagatattt cacaataatg aaagtacaaa agaaaaaatg  56580
ttggggctgg acatggtggc ttactcctgt aatcccagca ctttgagagg ccaaggtggg  56640
tggatcactt gaggccagga agtcgagaca agcctgatca acatgatgaa accccgtctc  56700
tattaaaaat acaaaaatta gccagacatg atggtgcaca cctgtaattc cagctactca  56760
agtggctgag gcacgagaat tgcttgaacc agggaggcgg aggttgcagt aagctgagat  56820
tgcaccactg caatccagcc aggtgacagg gtaagactgt gtctcaaaaa taaataaaag  56880
aaaaatatgt tggaagctca tccacattta agaaggaata tgacaattca ctaatgcata  56940
gaaaagaagt tcactccaca ttgtaaagtg tacagtgtaa tattatacaa tgaaaacaag  57000
gcaagtgctg tttaaactac tctggataca ttttttacaa agaaataaaa cactttagtt  57060
tttaatgttt ctaatgtttt acattttagt gtattaaatc aatattagtt ttcttctttt  57120
ttaagctccc tatacattta taactgacac taagggagtg tttaatgttt tgattaaaag  57180
ttgtaaagat cacagaacaa ttgtaattct tcccactgat tattcagatc attttgcaca  57240
atttcagctt gcatggtcac ttacagtgcc gcactatgtg caaagcaagg tcaggtctaa  57300
agttcgctaa tgaaaaatcc tcggccaggg gcagtggctc acccctgtaa tcctagcact  57360
ttggaaggcg aggcaggcag atcgcttgag ctcaggagtt caacaccagc ctgggcaaca  57420
tggtgagacc ctgtctctac aaaaaaaaaa aaatagcaag gcgtggtgac tcacacctgt  57480
agtcccagct acttgttggg ggctgagttg ggaaaatcac ttgagctcag gaggtcgagg  57540
ctgcagtgag ccagaatcac gccactgccc ttctgcctgg gtgacagagt aagatcctgt  57600
```

```
ctcaaaaaaa gggaaaatcc tcatctacat ttcactgggt tttttgtttg tttgtttgtt  57660
tgtttataca cacttaagga aattactgtc tagaagatag ataatataaa aaataaaaat  57720
gcaattcatg attcgggttt cttggtattc ctaagaactg ttgcacagta ctttatgctc  57780
tgaggcagac agctatagca tatatagtaa tttttgtttc tatcacataa acttgaatac  57840
acatatgagt aaaagacctt tagttcttca tgacttactg aaagaccctg actttttcca  57900
tgtaactgtt ccacaagtgt tttatggaaa actggataca ttaattcttc attcatccag  57960
cacgtacttg ttgaatggcc aatgtacacc aggtttgtag tagttactac tgtgaatgga  58020
aagtaaaaca gatgcaaaag gagaatacac taaaccaagt cttttatttt ttctctctct  58080
gatagggcta ccataaagct ttggtcaaac taaaactgaa aaaaaatacc gtggatgaca  58140
tttcagagag tctgcggcaa ggaggaggca agttaaactt tgacgaactt cgacaagatc  58200
tcaaagggtg agaatcatgc ttcctgaggt tctgaaaaat tcctgcttct aaagataaat  58260
tcctggtgat aagagtattt ctagcccaag ggctcataca gatacttttt tttttttttt  58320
ccagaggcag gtatctttct ggaacatgtt ataagaggaa aacttgcccc catttggtga  58380
tttctccttt cctcctgcat tttgatgtct ctgtgttgag ggtgaactgg gtacaaggaa  58440
tgatttttat ctgtatcctc tctctaattt caggaagggc catactgatg cagagattga  58500
ggcaatattc acaaagtacg accaagatgg agaccaagaa ctgaccgaac atgaacatca  58560
gcagatgaga gacgacttgg agaaagagag ggtgggtctg gtttaggaga accggatttg  58620
atttggtacc tacaacacca cagatgtatc aaacactata gaagtagtgg gttattgagt  58680
ctcttgccca ttccccacca cactctctct ctctctcagt cggtttatgt gttagtaccc  58740
tgtttattcc agaaagaata tataacacaa ttatgtataa aaatgggtgg ttagcatgat  58800
ataaaaacgt caaaatgaaa agcaagcaaa acaaaagtaa aaataatgga ttattaatga  58860
agcttaaaaa tgcattcata aaaacacata tgcttattaa gattgggcta caaattgggc  58920
cctaagcttg ctggtaatca gcttgaaaag agaagcctga ttagctgcag agtccacaat  58980
gtccgtgaga gtgaagaaaa caaaaaatga cttaccaaga gatgtgaaat tattctggtt  59040
agttagtggc tatttaaatt gttaactttt ttttcttttt tttttttttt tgagatggag  59100
tcttgctctg cctcccaggc tggagtgcag tggcacaatc gcgactcact gcaacctcca  59160
cctcccgggt tcaagcgatt ctcttgcctc agcctcccaa gtagctagga ctacaggcac  59220
atgccatcat gcccggctaa tttttgtatt tgtagtagat atggggtttc accatgttgg  59280
tctcaaactc ctgactgcaa gcaatctgcc caccttggcc tcccaaagtg gtgggattac  59340
aggcagtagc caccgtgcct ttcctaaatt attaacattt ataataaaat taacagccgc  59400
cttccatttg aatacttttt acaaaatagt taaaaataaa cataagtggg cttttatagt  59460
cagaaaaaaa aattcaaagc tttaccatta actttcaaaa ataaatggtt agacagcaac  59520
aacaaaaatc tgtggtaact gaggtacaga gaacacagat gaatgttatt acaaaagcca  59580
ctttcctatg agaagtctag gacagtggtt tctaaatgcc actccacaga cagtgctagt  59640
aggtgacaga cttctccagt cacagtgaaa tttaagcata aagaaaatga ggaaaatttt  59700
tacaaggctc tatttagaca aagttcttat tctgacatta catctttcct actttggagc  59760
tgttgaatgt attatctttt atgaaaagaa ggcgatccag gttgagcatc cctaacccaa  59820
atatgtgagt ctgaaatgct ccaaaaccta aaacttcttg agcacaaaca tgatagtcaa  59880
aggtcatgct taaaggaaat gctgtcattg gagcagtttg gattttgggt tttcagatta  59940
```

```
gggatgctga accagtaagt ataatgcaaa cattccaaaa tatttttgaa aatcccaaat  60000
ccaaaacact tctgatccca agtatttcaa ataagggata ctcaacctgt aatatatttc  60060
ttcatttctt tatttatttt attattattt taagatggct catggcccac tgcagcctca  60120
aactcctagg ctcaagtgat cttccgacct caacctccca ggtagctcag gtagctggga  60180
ctgcaggcat gcatcaccat gcctggctaa ttttttaaaa aattttttgt ggaggcagag  60240
tctcaccttg ctgcccaggc cagtctcaaa ctcctggctt caagcagtac tcctgcctca  60300
gcctcccaaa gtattaggat tacaggtgtg accactatgc ctggcccata tttcttcatt  60360
tagtttttc tttgcctgct gtgtttttaa tgttctttct tgttcaaaca aaaagttggc  60420
tattccttgc tgttagttaa atttgccaat ctatgaaact gaaaaatgca ggagtcccag  60480
cctggtgtta aatacaaaga aatcccaggt aaatggcatg cacccagttc ctgcttgccc  60540
aagtccttgg tgaggcttct gtggggtctc agtgttctgc tcctcactca gtgacccctt  60600
gttcttcagg aggacctgga tttggatcac agttctttac cacgtcccat gagcagccga  60660
agtttccctc gaagcctgga tgactctgag gaggatgacg atgaagatag cggacatagc  60720
tccagaagga ggggaagcat ttctagtggc gtttcttacg aagagtttca agtgtaagta  60780
taaaggaatt ggcagaattt gcgttgacaa gagtccacat gagaccaggc agttccctca  60840
tctctctgaa ttcactcctt tccattacta atcatccagc ttttaaaaat aacttatact  60900
ggccagacgc agtggctcat gcctgtaatc ccaccacttt gggaggccaa agcaggcagg  60960
tcatgaggtc agaagttcga gacgagcctg gccaacatag tgaaacccca tctctattaa  61020
aaatacaaaa aattagctgg gcatggtggt gggcacctgt aatcctagct acttgggagg  61080
ctgaggcaag agaattgctt gaacccggga ggcggaggtt acagagagcc gagatggctc  61140
cactgcacac cagcctgggc gacagtgcaa gactctgtct caaaaaaaaa aaaacttgtc  61200
aattggtgtt ttgtttctta cataatatgt ttactataaa aattagcaaa taagagcaaa  61260
agaaaacatt aacatttcac atatttctac caatgaaaaa tgtttattaa tatatcagtg  61320
tttgtgtctc tatttgcatg tgtttatcaa tgtttctata tatttttatg gcctaacata  61380
tggttcgtcc tgaagaatgt tccttgtgca tttgagaaga atgaatattc tgctgttcaa  61440
gtgttctgta gatgtttgtt aggtctagtt tgtttacagt tttattcagg tctcccattt  61500
cctggttgat cttagatgtg cctagatgtg gtattcacgt ttgaaagtgg ggtattaaag  61560
tctccaagta ttattagttg gagttcatcc cttcaattct gtaaggtttt gctttgtgta  61620
ttttggaact ctgttgttgg gtgcatacat atttataact agtatatttt cctaatatat  61680
tgaccctatt ttctctctca acttaatgag gctaaagaaa aaaaagaatt gaccctgttt  61740
tcattacaag atgttatcca ctttatctct agtaaaattc tttgttttaa gtatttttg  61800
tttgatatta ctgtaaccac tccagctttc ttttggttgc tgtttgcatg ataaatcttt  61860
ttccatcctt ttactttaaa cttatttata tctttcagtc tgaagtatgt ctctcctgta  61920
gacagcatat aattggatct tatcttttta tccagtttga caatttctgt ttttgattag  61980
attgcttaat ccattcattt aatgttatca ttgatgtagt tgatttctgt ctgctatttt  62040
attttttgtt ttctagctta cttttttttg ttcctctttc actgctttct tgtacattaa  62100
gtgaatattt tcaagtataa catttaaatt tttttaatga tttttcattt tttttagtca  62160
ggagttgctc taagacttag tttatacaat taagttatga aaaattactt cagatatata  62220
ttaactgaat ccagtgagat atagaaatca tttctattta gctttttttcc tcttccctct  62280
ttttgtgcta tatattcatc tatctatatg tatatatagt catctacata tgttgcaaat  62340
```

cacattgtta gaacaatgtt acatttttat aacacactgt gtaatatata gtatataatt 62400
ttatatctct taatgaagct gagagaagag gaagtatata tttataaatg tgtatattaa 62460
cctacttttt taccatttct aattctcttc ttttgctcct ctggattcaa gttatcatct 62520
gtcgtcattc tctttctccg atacagcttt gctactgcct acctcctatt attgtcaaat 62580
atattacatt tctattatag accttcagat ccaattatgt acatattttt acacaactgc 62640
tttttaaatc agttaaggaa caaaaggaga aatgtacata tatactatat tttataccta 62700
cacagttatc tttaccagtg ttctttgcct tttcatgtgg attctgatta ctatctggag 62760
tcacttgctt tcagcataaa gaatttcctt tagtattttt tgtaaagcag gtttgctagc 62820
aatgaattct ttcatttttt gtttatctga gaatgttttt ctttctcctt catttcctct 62880
ggcttgtatt gtttctgatg agaagacagg tgctaatttt actgtggtcc ccttgtacat 62940
gatgactcaa ttttctctca ccactttcaa gatttttttg cttttgtctt tcattatttt 63000
tactgtgata tgtctgggta taaatctctg agttcatcct acttagaaag tgtttttttct 63060 gcttctttca ctttctcttc tcctttggga cccgcattat gcatatgctt aggggtatca 63120
catatttctc ttaggctctg ttcgtcgtca tttttttttcc ctctctgttc ctcagagtgc 63180
atagtctgta ttgatgtatc ttcaagttca ctgacttgtt cttctgtcag cttgcttaaa 63240
tctctgttga gctcctctag ttatttattt atttatttat ttattttata tatatatata 63300
tatatatata tatagagaga gagagagaga gagagagaga aagagagaga gagagagaca 63360
gggagacagg gtctcactcc atcacccagg ctggagtaca gtggtgtaat catggctctc 63420
tacagcctga acacctgggc tcaaatgatc ctcctgcctc aacctcccaa gtagctagga 63480
ctatgggcac atgctgccat gcctggctaa tttttaaaaa aaaatttgta gagatggcat 63540
cttgttatgt tgcccaggtt ggtctcaaac tcccggcctc aagtgatcct tccgcctcgg 63600
cctcccaaag tgctggggtc acaggtatga gccaccgcac ttagcctgaa ttttttattt 63660
attatacttt tcaactccag aatttctatt tggttctttt tagcaatctc tgtctcttta 63720
ttctgtattt gatgatatcc tgtatttgat gagacaatgt catcataact tcctttttttt 63780 tttaagagat agggtctctc tctgtcaccc aggctagagt gcagtggcat gatcctagct 63840
cactgcagcc tcgaactcct gaactcaagc aatcctccca cctcagcctc ctaagtacct 63900
gacactacag gcatgagcca ctgtacccag ctaattttta tttttgtag agatggggtc 63960 taagttgccc aggctggtct caaactcctg ggctcaagtg atcctccctg ctcaggctcc 64020
caaagtgctg ggattacagg catgaaccac tggacccagc ctcctttatt tctttaacca 64080
tggtggggtt ttttattatt tgtttgtttg ttttaacctg tttgaatata tttataatag 64140
gtaccttcag gtctttgtct gctaagtctg acatctgggc cctctcaaag acagtttcag 64200
ttgtcttttt tttttcttc ttgtgtatgg gaacattttc ctgttttttt gttttgtttt 64260
ttgttgtttt gttttgttgt tgttgttgtt gttaaagatt ggacatgtta gataatatat 64320
tgtaggaact ctggctagtg attccctttc ctccccagga cttgttttta tttctctttg 64380
cttgtttact ttttcataca gtctgtttcc ccacagtgtc tgcctctgac tttattcctt 64440
agagggcgca gctgtggcca tgtacgtagt cactctggga agacagtggt tttagcagcg 64500
tgctcattaa ctttctctga cctctttgtt atacctcctg cctctgtgga tattagaccc 64560
agttattaca tttcattgtt tactgattgg tctattgttt tccagaatgc cttgggatgt 64620
aatttgctcc acagtctgat ccacttaaat tcaggcctct ttgcagggct agttttagag 64680

-continued

```
gccagtcttt tttttttttt tttttttttt ttgagacaga gtctcactct gttgcccagg  64740
ccggaatgta gtggtgcagt ctcagctcac tgcagcctca atctctcagg ctcaagcaat  64800
cttcccacct cagcttctca agtagctagg actacaggtg cacgccacca tgcctggtta  64860
atttttgcat tttttataga gatggggttt taccatgttg ccccggctgg tctcaaactc  64920
ctgagttcaa gcaatccacc cacctcagcc tcacaaaagg ccgggattac agatatgcac  64980
caccacgcct ggcccctgag gccagtcttt aactgtcttc ttagctgtct ctttccctgg  65040
ttctctctgg tgaactagct ggtaatttgt ttatctcata aggctaccag attccttgta  65100
aatgcttatc cccacaatct ccattgtttt caagagcatc gttagtcttt aatttcctca  65160
cgcttcattc caaataaagt ccattcactt gagaagagtt ctatattcct atgacctgtg  65220
tctccccatg agcaaaactg ctactgcttt acagagccag ggacagtggc ccacctctct  65280
gtggcatcct gctttatgaa caagtcactg ggctcagatg gcagtctctg attttctcac  65340
cttgcttctt ctggcatgga aactccaccc tacaagtggg aactgagtgg aagaagagag  65400
ccccattccc cttagccact cttaacagga ttagaacctc tgcaacatgc atttaagaat  65460
gggaacaggc tgggcacagt ggctcacgcc tgtaatccta gcactttggg aggtcaaggc  65520
aggaggattg cttgagccag gagttcagga ccagcctgtg caacatggtg agaccctcat  65580
ctctacaaga aatagaaaaa ttaactggtg ggttgtgtat acctgtaatc ccagctactc  65640
gggagcctga agtgggagga ttgcttgaac ctggaggcag aggttgcagt gagtcaagat  65700
tacaccattg cacgccagcc tgggcaacag agtgagactc tgtctcaaaa aaaaaaaaaa  65760
aaaaagagta ggaacattga ggctgggcat ggtggctcat gcctgtaatc ctagcactat  65820
gggaggccaa ggcaggagta tcacttgacg ctaggagttc aagaccaacc tgggtaacat  65880
agcgagactt tgtctctatt aaaaaaaaaa aaaaaaaagg tgtaaaaaac ttttgtaaca  65940
agagtgggaa agccgggcac agtggctcac acctgtaatc ccagcacttt ggaaggccaa  66000
ggcaggcagg cggatcacct gaggtcagga gtttgagacc agcctggcca acgtggtgaa  66060
accccatctc tactaaaaaa tagaaaaatt atctgggcat ggtggtgcac acctgtagtc  66120
ccagctactc gggaggctga ggcaggagaa tcacttgaac ctacgaggca gaagttgcag  66180
taagccaaga tcacgccact gcactccagc ctgggcgaca gagcaagact ctgtctcaaa  66240
aaaaaaaaaa gagtggaaat gttaggatga gaaatgctgg cagcctgccc ctccctggga  66300
gatactgtag ccctagactg gaagttgggg gaggagggag ccctgtgctc ttagctgcac  66360
ccatgtgaag ttgtgcttct atcacatgag ctggggacag gagagaaggc tcagattatg  66420
gcttcagtgc cacagaatct cttcatacta aaatttagta gattttcttg aataaatgct  66480
ttttcatttg ctgtacaccc ttaaaagttt ctagaaattt ttaatatttg agttttaaaa  66540
aataattttc aacagttaca gttatttcac taaagagaga gtctacagaa ccctcttgcc  66600
accattgcag aggttgtctt tggcttacga gtttttaaag tatttgtata catttttttaa  66660
gttcaaaata atagaattgt aagtgaacat gctgttttca tactgttttt caagctttat  66720
ttaatatatt gtaaatctaa ttctatttta ttaaatagtc tgccacagta taatgtctga  66780
tgtctcctta gaattttatt gtatggatga acaatgatta tttaatttcc taccaattgt  66840
tgggtgtttt ttgtttgttt gtttgttttt gagactgggt ctcactctgt cacccaggct  66900
ggagtgcagg agtgcggtgg aatgatcacg gctcactgca gcctcaacat cccaaggctc  66960
aggtgatcct tccacctcag cctcgcaagt agctgggagt acaggcacat gccaccatgc  67020
ccacctattt tttagagatg aagttttgcc atcctgccca ggctggctcg aactcctggc  67080
```

ctcaagcgat ctgcacactt ccgcctccca aaatgccagg attacaggcg tgagccatca 67140
tgccctaccc ccccatcaat tgtttgatgt agccattttt caatgatccg cgattaagaa 67200
gcagcactct tttatagcca aaaattacac atatataaaa ttttccttta gaaaatgttc 67260
taaaaatgga atgtctaact aaagggttag gcatacattc ttaagacttc tgatacgcgc 67320
tgacttgcag gaaagttgtt tcagttaaca ctcctaccag cggcatccga gagttaatct 67380
gtaaagcttg agacaactta gaaagtgttt caaatgattg tgttgcttaa gaaaaaaatc 67440
ttagcacttc cttttgaaaa gccagtgggg ctgaaaagac aatgacaagc actttgtccc 67500
tctgtactgt gttttccttg cagcctggtg agacgagtgg accggatgga gcattccatc 67560
ggcagcatag tgtccaagat tgacgccgtg atcgtgaagc tagagattat ggagcgagcc 67620
aaactgaaga ggagggaggt gctgggaagg ctgttggatg gggtggccga ggtcagtagt 67680
catgagctga aaacaccgct gctgagcatg gtgttattaa tgaaaatata tgttgctgac 67740
agttgtattt gaagtattga agaagagtaa aaaaaattta cgtttataga aattcacaat 67800
gatgtttcca tttactctca ttttcagatt tttttctctg aaacagaaac actctttcta 67860
taaaatctct tgctataaaa catcaatgta gtcatattgt ctaaccctta ggctgagatg 67920
tttatctttc tccataacta cagataaaat tataatctgg aggtgttact ttcttaatac 67980
tccatatgct aatggtcctg ccttcactgc agggtagaat taagtgaaaa attactccag 68040
caactctgag atttgctatt atatgctgta aatctccagc cttaccaaac tacagattat 68100
ttggtccctg gacttcctaa ggcatttcct tctactgccc ccaacaccag tttctttttc 68160
cctttttagg atgaaaggct gggtcgtgac agtgaaatcc atagggaaca gatggaacgg 68220
ctagtacgtg aagagttgga acgctgggaa tccgatgatg cagcttccca gatcagtcat 68280
ggtttaggca cgccagtggg actaaatggt caacctcgcc ccagaagctc ccgcccatct 68340
tcctcccaat ctacagaagg catggaaggt gcaggtggaa atgggagttc taatgtccac 68400
gtatgatatg tgtgtttcag tatgtgtgtt tctaataagt gaggaagtgg ctgtcctgaa 68460
ttgctgtaac aagcacacta tttatatgcc ctgaccacca taggatgcta gtctttgtga 68520
ccgattgcta atcttctgca ctttaattta ttttatataa actttaccca tggttcaaag 68580 atttttttt ctttttctca tataagaaat ctaggtgtaa atattgagta cagaaaaaaa 68640
atcttcatga tgtgtattga gcggtacgcc cagttgccac catgactgag tcttctcagt 68700
tgacaatgaa gtagcctttt aaagctagaa aactgtcaaa gggcttctga gtttcatttc 68760
cagtcacaaa aatcagtatt gttatttttt tccaagagtg tgaaggaaaa tggggcat 68818

<210> SEQ ID NO 39
<211> LENGTH: 120
<212> TYPE: DNA
<213> ORGANISM: Artificial Sequence
<220> FEATURE:
<223> OTHER INFORMATION: Synthetic nucleotide sequence

<400> SEQUENCE: 39
gcctgggcct gtggctcggg gcgctggcgg ggggccccgg gcgcggctgc gggccctgcg 60
agcccccctg cctctgcggc ccagcgcccg gcgccgcctg ccgcgtcaac tgctcgggcc 120

<210> SEQ ID NO 40
<211> LENGTH: 120
<212> TYPE: DNA
<213> ORGANISM: Artificial Sequence
<220> FEATURE:

<223> OTHER INFORMATION: Synthetic nucleotide sequence

<400> SEQUENCE: 40
gcctgggcct gtggctcggg gcgctggcgg ggggccccgg gcgcggctgc gggccttgcg 60
agcccccctg cctctgcggc ctagcgcccg gcgccgcctg ccgcgtcaac tgctcgggcc 120

<210> SEQ ID NO 41
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 41
cccaggcctg acactgctcc tgcgcctgca gccaggccgc cttctccacc accaggcggt 60

<210> SEQ ID NO 42
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 42
cccaggcccg acactgctcc tgcgcctgca gccaggccgc cttctccacc accaggcggt 60

<210> SEQ ID NO 43
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 43
gggcctcaag cccagcagca cggtgagctg ttccgtggct gcaagcagcc gcagggcaca 60

<210> SEQ ID NO 44
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 44
gggcctcagg cccagcagca cggtgagctg ttccgtggct gcaagcagcc gcagggcaca 60

<210> SEQ ID NO 45
<211> LENGTH: 57
<212> TYPE: DNA
<213> ORGANISM: Artificial Sequence
<220> FEATURE:
<223> OTHER INFORMATION: Synthetic nucleotide sequence

<400> SEQUENCE: 45
gtgctggcat ctaatgcctt cgagaacctg acgcagcagg tgcctgtgag cgtgcgc 57

<210> SEQ ID NO 46
<211> LENGTH: 57
<212> TYPE: DNA
<213> ORGANISM: Artificial Sequence
<220> FEATURE:
<223> OTHER INFORMATION: Synthetic nucleotide sequence

<400> SEQUENCE: 46
gtgctggcat ctaatgcctt cgagaaccgg acgcagcagg tgcctgtgag cgtgtgc 57

<210> SEQ ID NO 47
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 47
gtgctggcat ctaatgcctt cgagaaccgg acgcagcagg tgcctgtgag cgtgcgc 57

<210> SEQ ID NO 48
<211> LENGTH: 57
<212> TYPE: DNA
<213> ORGANISM: Artificial Sequence
<220> FEATURE:
<223> OTHER INFORMATION: Synthetic nucleotide sequence

<400> SEQUENCE: 48
gtgctggcat ctaatgcctt cgagaaccgg atgcagcagg tgcctgtgag cgtgcgc 57

<210> SEQ ID NO 49
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 49
agcacgagcg gcagcaccga gcccagatac gcaagaacat cacggagact ctggtgtccc 60

<210> SEQ ID NO 50
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 50
agcacgagcg gcagcgccga gcccagatac gcaagaacat cacggagact ctggtgtccc 60

<210> SEQ ID NO 51
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 51
gtcttgacga ggatctcgta cttgaagcgg ccccgctgcc cacagaaagg gatggcgcgg 60

<210> SEQ ID NO 52
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 52
gtcttgacga ggatctcgta cttgaagcgg ccccgctgcc cacagaaggg gatggcgcag 60

<210> SEQ ID NO 53
<211> LENGTH: 60
<212> TYPE: DNA
<213> ORGANISM: Artificial Sequence
<220> FEATURE:

-continued

```
<223> OTHER INFORMATION: Synthetic nucleotide sequence

<400> SEQUENCE: 53

gtcttgacga ggatctcgta cttgaagcgg ccccgctgcc cacagaaggg gatggcgcgg     60


<210> SEQ ID NO 54
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 54

tcccgtctac ctggccatcc tttttctctt ccggatgtcc cggagcaagg tgggctgggg     60


<210> SEQ ID NO 55
<211> LENGTH: 60
<212> TYPE: DNA
<213> ORGANISM: Artificial Sequence
<220> FEATURE:
<223> OTHER INFORMATION: Synthetic oligonucleotide sequence

<400> SEQUENCE: 55

tcccgtctac ctggccatcc tctttctctt ccggatgtcc cggagcaagg tgggctgggg     60


<210> SEQ ID NO 56
<211> LENGTH: 60
<212> TYPE: DNA
<213> ORGANISM: Artificial Sequence
<220> FEATURE:
<223> OTHER INFORMATION: Synthetic nucleotide sequence

<400> SEQUENCE: 56

tcccgtctac ctggccatcc tctttctctt ctggatgtcc cggagcaagg tgggctgggg     60
```